US012571029B1

(12) United States Patent
Galonska et al.

(10) Patent No.: US 12,571,029 B1
(45) Date of Patent: *Mar. 10, 2026

(54) METHODS, COMPOSITIONS, AND KITS FOR DETERMINING THE LOCATION OF MULTIPLE ANALYTES IN A BIOLOGICAL SAMPLE

(71) Applicant: 10x Genomics, Inc., Pleasanton, CA (US)

(72) Inventors: Christina Galonska, Stockholm (SE); Malte Kuhnemund, Stockholm (SE)

(73) Assignee: 10x Genomics, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/914,833

(22) Filed: Oct. 14, 2024

Related U.S. Application Data

(63) Continuation of application No. PCT/US2023/079071, filed on Nov. 8, 2023.

(60) Provisional application No. 63/424,056, filed on Nov. 9, 2022.

(51) Int. Cl.
C12Q 1/6841 (2018.01)
C12Q 1/682 (2018.01)

(52) U.S. Cl.
CPC ........... C12Q 1/6841 (2013.01); C12Q 1/682 (2013.01)

(58) Field of Classification Search
CPC .................................. C12Q 1/68; C07H 21/00
See application file for complete search history.

(56) References Cited

U.S. PATENT DOCUMENTS

| | | | |
|---|---|---|---|
| 4,683,195 A | 7/1987 | Mullis |
| 4,683,202 A | 7/1987 | Mullis |
| 4,800,159 A | 1/1989 | Mullis |
| 4,883,867 A | 11/1989 | Lee |
| 4,965,188 A | 10/1990 | Mullis |
| 4,988,617 A | 1/1991 | Landegren et al. |
| 5,002,882 A | 3/1991 | Lunnen |
| 5,130,238 A | 7/1992 | Malek |
| 5,308,751 A | 5/1994 | Ohkawa |
| 5,321,130 A | 6/1994 | Yue |
| 5,410,030 A | 4/1995 | Yue |
| 5,436,134 A | 7/1995 | Haugland |
| 5,455,166 A | 10/1995 | Walker |
| 5,494,810 A | 2/1996 | Barany et al. |
| 5,503,980 A | 4/1996 | Cantor |
| 5,512,439 A | 4/1996 | Hornes |
| 5,512,462 A | 4/1996 | Cheng |
| 5,582,977 A | 12/1996 | Yue |
| 5,599,675 A | 2/1997 | Brenner |
| 5,641,658 A | 6/1997 | Adams |
| 5,648,245 A | 7/1997 | Fire et al. |
| 5,658,751 A | 8/1997 | Yue |
| 5,695,940 A | 12/1997 | Drmanac et al. |

| | | | |
|---|---|---|---|
| 5,750,341 A | 5/1998 | Macevicz |
| 5,763,175 A | 6/1998 | Brenner |
| 5,830,711 A | 11/1998 | Barany et al. |
| 5,837,832 A | 11/1998 | Chee et al. |
| 5,854,033 A | 12/1998 | Lizardi |
| 5,863,753 A | 1/1999 | Haugland |
| 5,871,921 A | 2/1999 | Landegren et al. |
| 5,912,148 A | 6/1999 | Eggerding |
| 5,925,545 A | 7/1999 | Reznikoff et al. |
| 5,928,906 A | 7/1999 | Koester et al. |
| 5,958,775 A | 9/1999 | Wickstrrom |
| 5,962,271 A | 10/1999 | Chenchik et al. |
| 5,962,272 A | 10/1999 | Chenchik et al. |
| 5,965,443 A | 10/1999 | Reznikoff et al. |
| 6,013,440 A | 1/2000 | Lipshutz |
| 6,027,889 A | 2/2000 | Barany et al. |
| 6,054,274 A | 4/2000 | Sampson et al. |
| 6,060,240 A | 5/2000 | Kamb et al. |
| 6,130,073 A | 10/2000 | Eggerding |
| 6,143,496 A | 11/2000 | Brown |
| 6,153,389 A | 11/2000 | Haarer |
| 6,159,736 A | 12/2000 | Reznikoff et al. |
| 6,165,714 A | 12/2000 | Lane et al. |
| 6,210,891 B1 | 4/2001 | Nyren |
| 6,210,894 B1 | 4/2001 | Brennan |
| 6,214,587 B1 | 4/2001 | Dattagupta |
| 6,251,639 B1 | 6/2001 | Kurn |
| 6,258,568 B1 | 7/2001 | Nyren |
| 6,266,459 B1 | 7/2001 | Walt |
| 6,268,148 B1 | 7/2001 | Barany et al. |
| 6,274,320 B1 | 8/2001 | Rothberg |
| 6,291,180 B1 | 9/2001 | Chu |
| 6,291,187 B1 | 9/2001 | Kingsmore et al. |
| 6,300,063 B1 | 10/2001 | Lipshutz et al. |
| 6,309,824 B1 | 10/2001 | Drmanac |
| 6,323,009 B1 | 11/2001 | Lasken et al. |
| 6,344,316 B1 | 2/2002 | Lockhart |
| 6,344,329 B1 | 2/2002 | Lizardi et al. |
| 6,355,431 B1 | 3/2002 | Chee |
| 6,368,801 B1 | 4/2002 | Faruqi |
| 6,401,267 B1 | 6/2002 | Drmanac |
| 6,404,907 B1 | 6/2002 | Gilchrist |
| 6,432,360 B1 | 8/2002 | Church et al. |
| 6,503,713 B1 | 1/2003 | Rana |
| 6,506,561 B1 | 1/2003 | Cheval et al. |
| 6,534,266 B1 | 3/2003 | Singer |
| 6,544,732 B1 | 4/2003 | Chee |
| 6,573,043 B1 | 6/2003 | Cohen et al. |

(Continued)

FOREIGN PATENT DOCUMENTS

| | | |
|---|---|---|
| AU | 2003200718 | 10/2006 |
| CN | 1273609 | 11/2000 |

(Continued)

OTHER PUBLICATIONS

Wulf et al.Non-templated addition and template switching by Moloney murine leukemia virus (MMLV)-based reverse transcriptases co-occur and compete with each other. JBC294(48) : 18220-18231 (Year: 2019).*

(Continued)

*Primary Examiner* — Ethan C Whisenant
(74) *Attorney, Agent, or Firm* — Fish & Richardson P.C.

(57) ABSTRACT

Provided herein are methods, compositions, and kits for the spatial analysis of target nucleic acids, or complements thereof, by their 5' end.

24 Claims, 10 Drawing Sheets

Specification includes a Sequence Listing.

(56) References Cited

U.S. PATENT DOCUMENTS

| | | |
|---|---|---|
| 6,579,695 B1 | 6/2003 | Lambalot |
| 6,620,584 B1 | 9/2003 | Chee |
| 6,632,641 B1 | 10/2003 | Brennan |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,797,470 B2 | 9/2004 | Barany et al. |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,852,487 B1 | 2/2005 | Barany et al. |
| 6,859,570 B2 | 2/2005 | Walt |
| 6,864,052 B1 | 3/2005 | Drmanac |
| 6,867,028 B2 | 3/2005 | Janulaitis |
| 6,872,816 B1 | 3/2005 | Hall et al. |
| 6,875,572 B2 | 4/2005 | Prudent et al. |
| 6,890,741 B2 | 5/2005 | Fan et al. |
| 6,897,023 B2 | 5/2005 | Fu |
| 6,913,881 B1 | 7/2005 | Aizenstein et al. |
| 6,942,968 B1 | 9/2005 | Dickinson et al. |
| 7,011,944 B2 | 3/2006 | Prudent et al. |
| 7,057,026 B2 | 6/2006 | Barnes |
| 7,083,980 B2 | 8/2006 | Reznikoff et al. |
| 7,115,400 B1 | 10/2006 | Adessi |
| 7,118,883 B2 | 10/2006 | Inoue |
| 7,166,431 B2 | 1/2007 | Chee et al. |
| 7,192,735 B2 | 3/2007 | Lambalot |
| 7,211,414 B2 | 5/2007 | Hardin |
| 7,255,994 B2 | 8/2007 | Lao |
| 7,258,976 B2 | 8/2007 | Mitsuhashi |
| 7,282,328 B2 | 10/2007 | Kong et al. |
| 7,297,518 B2 | 11/2007 | Quake |
| 7,329,492 B2 | 2/2008 | Hardin |
| 7,358,047 B2 | 4/2008 | Hafner et al. |
| 7,361,488 B2 | 4/2008 | Fan et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,473,767 B2 | 1/2009 | Dimitrov |
| 7,499,806 B2 | 3/2009 | Kermani et al. |
| 7,537,897 B2 | 5/2009 | Brenner |
| 7,563,576 B2 | 7/2009 | Chee |
| 7,579,153 B2 | 8/2009 | Brenner |
| 7,582,420 B2 | 9/2009 | Oliphant et al. |
| 7,601,498 B2 | 10/2009 | Mao |
| 7,608,434 B2 | 10/2009 | Reznikoff et al. |
| 7,611,869 B2 | 11/2009 | Fan |
| 7,635,566 B2 | 12/2009 | Brenner |
| 7,666,612 B2 | 2/2010 | Johnsson |
| 7,674,752 B2 | 3/2010 | He |
| 7,709,198 B2 | 5/2010 | Luo et al. |
| 7,776,547 B2 | 8/2010 | Roth |
| 7,776,567 B2 | 8/2010 | Mao |
| 7,803,943 B2 | 9/2010 | Mao |
| 7,888,009 B2 | 2/2011 | Barany et al. |
| 7,892,747 B2 | 2/2011 | Barany et al. |
| 7,910,304 B2 | 3/2011 | Drmanac |
| 7,914,981 B2 | 3/2011 | Barany et al. |
| 7,955,794 B2 | 6/2011 | Shen et al. |
| 7,960,119 B2 | 6/2011 | Chee |
| 7,985,565 B2 | 7/2011 | Mayer et al. |
| 8,003,354 B2 | 8/2011 | Shen et al. |
| 8,076,063 B2 | 12/2011 | Fan |
| 8,092,784 B2 | 1/2012 | Mao |
| 8,148,068 B2 | 4/2012 | Brenner |
| 8,206,917 B2 | 6/2012 | Chee |
| 8,268,554 B2 | 9/2012 | Schallmeiner |
| 8,288,103 B2 | 10/2012 | Oliphant |
| 8,288,122 B2 | 10/2012 | O'Leary et al. |
| 8,383,338 B2 | 2/2013 | Kitzman |
| 8,431,691 B2 | 4/2013 | McKernan et al. |
| 8,460,865 B2 | 6/2013 | Chee |
| 8,481,257 B2 | 7/2013 | Van Eijk |
| 8,481,258 B2 | 7/2013 | Church et al. |
| 8,481,292 B2 | 7/2013 | Casbon |
| 8,481,698 B2 | 7/2013 | Lieberman et al. |
| 8,507,204 B2 | 8/2013 | Pierce et al. |
| 8,519,115 B2 | 8/2013 | Webster et al. |
| 8,551,710 B2 | 10/2013 | Bernitz et al. |
| 8,568,979 B2 | 10/2013 | Stuelpnagel et al. |
| 8,586,310 B2 | 11/2013 | Mitra |
| 8,597,891 B2 | 12/2013 | Barany et al. |
| 8,603,743 B2 | 12/2013 | Liu et al. |
| 8,604,182 B2 | 12/2013 | Luo et al. |
| 8,614,073 B2 | 12/2013 | Van Eijk |
| 8,624,016 B2 | 1/2014 | Barany et al. |
| 8,685,889 B2 | 4/2014 | Van Eijk |
| 8,741,564 B2 | 6/2014 | Seligmann |
| 8,741,606 B2 | 6/2014 | Casbon |
| 8,771,950 B2 | 7/2014 | Church et al. |
| 8,785,353 B2 | 7/2014 | Van Eijk |
| 8,790,873 B2 | 7/2014 | Namsaraev et al. |
| 8,809,238 B2 | 8/2014 | Livak et al. |
| 8,815,512 B2 | 8/2014 | Van Eijk |
| 8,835,358 B2 | 9/2014 | Fodor |
| 8,865,410 B2 | 10/2014 | Shendure |
| 8,906,626 B2 | 12/2014 | Oliphant et al. |
| 8,911,945 B2 | 12/2014 | Van Eijk |
| 8,936,912 B2 | 1/2015 | Mitra |
| 8,951,726 B2 | 2/2015 | Luo et al. |
| 8,951,728 B2 | 2/2015 | Rasmussen |
| 8,986,926 B2 | 3/2015 | Ferree et al. |
| 9,005,891 B2 | 4/2015 | Sinicropi et al. |
| 9,005,935 B2 | 4/2015 | Belyaev |
| 9,023,768 B2 | 5/2015 | Van Eijk |
| 9,062,348 B1 | 6/2015 | Van Eijk |
| 9,080,210 B2 | 7/2015 | Van Eijk |
| 9,194,001 B2 | 11/2015 | Brenner |
| 9,201,063 B2 | 12/2015 | Sood et al. |
| 9,273,349 B2 | 3/2016 | Nguyen et al. |
| 9,290,808 B2 | 3/2016 | Fodor |
| 9,290,809 B2 | 3/2016 | Fodor |
| 9,328,383 B2 | 5/2016 | Van Eijk |
| 9,330,295 B2 | 5/2016 | Dunn |
| 9,334,536 B2 | 5/2016 | Van Eijk |
| 9,371,563 B2 | 6/2016 | Geiss et al. |
| 9,371,598 B2 | 6/2016 | Chee |
| 9,376,716 B2 | 6/2016 | Van Eijk |
| 9,376,717 B2 | 6/2016 | Gao et al. |
| 9,376,719 B2 | 6/2016 | Eijk |
| 9,416,409 B2 | 8/2016 | Hayden |
| 9,447,459 B2 | 9/2016 | Van Eijk |
| 9,453,256 B2 | 9/2016 | Van Eijk |
| 9,493,820 B2 | 11/2016 | Van Eijk |
| 9,506,061 B2 | 11/2016 | Brown et al. |
| 9,512,422 B2 | 12/2016 | Barnard et al. |
| 9,574,230 B2 | 2/2017 | Van Eijk |
| 9,593,365 B2 | 3/2017 | Frisen et al. |
| 9,598,728 B2 | 3/2017 | Barany et al. |
| 9,624,538 B2 | 4/2017 | Church et al. |
| 9,644,204 B2 | 5/2017 | Hindson et al. |
| 9,657,335 B2 | 5/2017 | Van Eijk |
| 9,670,542 B2 | 6/2017 | Eijk |
| 9,694,361 B2 | 7/2017 | Bharadwaj |
| 9,702,004 B2 | 7/2017 | Van Eijk |
| 9,714,446 B2 | 7/2017 | Webster et al. |
| 9,714,937 B2 | 7/2017 | Dunaway |
| 9,727,810 B2 | 8/2017 | Fodor et al. |
| 9,745,627 B2 | 8/2017 | Van Eijk |
| 9,777,324 B2 | 10/2017 | Van Eijk |
| 9,783,841 B2 | 10/2017 | Nolan et al. |
| 9,790,476 B2 | 10/2017 | Gloeckner et al. |
| 9,816,134 B2 | 11/2017 | Namsaraev |
| 9,834,814 B2 | 12/2017 | Peter et al. |
| 9,850,536 B2 | 12/2017 | Oliphant et al. |
| 9,856,521 B2 | 1/2018 | Stevens et al. |
| 9,868,979 B2 | 1/2018 | Chee et al. |
| 9,879,313 B2 | 1/2018 | Chee et al. |
| 9,896,721 B2 | 2/2018 | Van Eijk |
| 9,898,576 B2 | 2/2018 | Van Eijk |
| 9,898,577 B2 | 2/2018 | Van Eijk |

(56) References Cited

U.S. PATENT DOCUMENTS

| | | | |
|---|---|---|---|
| 9,902,991 B2 | 2/2018 | Sinicropi et al. | |
| 9,909,167 B2 | 3/2018 | Samusik et al. | |
| 9,938,566 B2 | 4/2018 | Shepard et al. | |
| 9,957,550 B2 | 5/2018 | Yeakley et al. | |
| 10,002,316 B2 | 6/2018 | Fodor et al. | |
| 10,023,907 B2 | 7/2018 | Van Eijk | |
| 10,030,261 B2 | 7/2018 | Frisen et al. | |
| 10,035,992 B2 | 7/2018 | Gloeckner et al. | |
| 10,041,949 B2 | 8/2018 | Bendall et al. | |
| 10,059,989 B2 | 8/2018 | Giresi et al. | |
| 10,059,990 B2 | 8/2018 | Boyden et al. | |
| 10,095,832 B2 | 10/2018 | Van Eijk | |
| 10,101,336 B2 | 10/2018 | Bergo | |
| 10,144,966 B2 | 12/2018 | Cantor | |
| 10,227,639 B2 | 3/2019 | Levner et al. | |
| 10,273,541 B2 | 4/2019 | Hindson et al. | |
| 10,308,982 B2 | 6/2019 | Chee | |
| 10,357,771 B2 | 7/2019 | Bharadwaj | |
| 10,370,698 B2 | 8/2019 | Nolan et al. | |
| 10,415,080 B2 | 9/2019 | Dunaway et al. | |
| 10,465,235 B2 | 11/2019 | Gullberg et al. | |
| 10,472,669 B2 | 11/2019 | Chee | |
| 10,480,022 B2 | 11/2019 | Chee | |
| 10,480,029 B2 | 11/2019 | Bent et al. | |
| 10,494,667 B2 | 12/2019 | Chee | |
| 10,495,554 B2 | 12/2019 | Deisseroth et al. | |
| 10,501,777 B2 | 12/2019 | Beechem et al. | |
| 10,501,791 B2 | 12/2019 | Church et al. | |
| 10,510,435 B2 | 12/2019 | Cai et al. | |
| 10,544,403 B2 | 1/2020 | Gloeckner et al. | |
| 10,550,429 B2 | 2/2020 | Harada et al. | |
| 10,590,244 B2 | 3/2020 | Delaney et al. | |
| 10,633,648 B2 | 4/2020 | Seelig et al. | |
| 10,640,816 B2 | 5/2020 | Beechem et al. | |
| 10,640,826 B2 | 5/2020 | Church et al. | |
| 10,662,468 B2 | 5/2020 | Chee | |
| 10,669,569 B2 | 6/2020 | Gullberg et al. | |
| 10,724,078 B2 | 7/2020 | Van Driel et al. | |
| 10,725,027 B2 | 7/2020 | Bell | |
| 10,774,372 B2 | 9/2020 | Chee et al. | |
| 10,774,374 B2 | 9/2020 | Frisen et al. | |
| 10,787,701 B2 | 9/2020 | Chee | |
| 10,815,519 B2 | 10/2020 | Husain et al. | |
| 10,829,803 B2 | 11/2020 | Terbrueggen et al. | |
| 10,844,426 B2 | 11/2020 | Daugharthy et al. | |
| 10,858,698 B2 | 12/2020 | Church et al. | |
| 10,858,702 B2 | 12/2020 | Lucero et al. | |
| 10,913,975 B2 | 2/2021 | So et al. | |
| 10,914,730 B2 | 2/2021 | Chee et al. | |
| 10,927,403 B2 | 2/2021 | Chee et al. | |
| 10,961,566 B2 | 3/2021 | Chee | |
| 11,001,879 B1 | 5/2021 | Chee | |
| 11,008,607 B2 | 5/2021 | Chee | |
| 11,046,996 B1 | 6/2021 | Chee et al. | |
| 11,067,567 B2 | 7/2021 | Chee | |
| 11,104,936 B2 | 8/2021 | Zhang et al. | |
| 11,118,216 B2 | 9/2021 | Koshinsky et al. | |
| 11,156,603 B2 | 10/2021 | Chee | |
| 11,162,132 B2 | 11/2021 | Frisen et al. | |
| 11,208,684 B2 | 12/2021 | Chee | |
| 11,214,796 B2 | 1/2022 | Shirai et al. | |
| 11,286,515 B2 | 3/2022 | Chee et al. | |
| 11,293,917 B2 | 4/2022 | Chee | |
| 11,299,774 B2 | 4/2022 | Frisen et al. | |
| 11,313,856 B2 | 4/2022 | Chee | |
| 11,332,790 B2 * | 5/2022 | Chell | C12Q 1/6816 |
| 11,352,659 B2 | 6/2022 | Frisen et al. | |
| 11,352,667 B2 | 6/2022 | Hauling et al. | |
| 11,359,228 B2 | 6/2022 | Chee et al. | |
| 11,365,442 B2 | 6/2022 | Chee | |
| 11,371,086 B2 | 6/2022 | Chee | |
| 11,384,386 B2 | 7/2022 | Chee | |
| 11,390,912 B2 | 7/2022 | Frisen et al. | |
| 11,401,545 B2 | 8/2022 | Chee | |
| 11,407,992 B2 | 8/2022 | Dadhwal | |
| 11,408,029 B2 | 8/2022 | Katiraee et al. | |
| 11,434,524 B2 | 9/2022 | Ramachandran Iyer et al. | |
| 11,479,809 B2 | 10/2022 | Frisen et al. | |
| 11,479,810 B1 | 10/2022 | Chee | |
| 11,492,612 B1 | 11/2022 | Dadhwal | |
| 11,501,440 B2 | 11/2022 | Weisenfeld et al. | |
| 11,505,828 B2 | 11/2022 | Chell et al. | |
| 11,512,308 B2 | 11/2022 | Gallant et al. | |
| 11,519,022 B2 | 12/2022 | Chee | |
| 11,519,033 B2 | 12/2022 | Schnall-Levin et al. | |
| 11,530,438 B2 | 12/2022 | Persson et al. | |
| 11,535,887 B2 | 12/2022 | Gallant et al. | |
| 11,542,543 B2 | 1/2023 | Chee | |
| 11,549,138 B2 | 1/2023 | Chee | |
| 11,560,587 B2 | 1/2023 | Chee | |
| 11,560,592 B2 | 1/2023 | Chew et al. | |
| 11,560,593 B2 * | 1/2023 | Chell | C12Q 1/25 |
| 11,592,447 B2 | 2/2023 | Uytingco et al. | |
| 11,608,498 B2 | 3/2023 | Gallant et al. | |
| 11,608,520 B2 * | 3/2023 | Galonska | C12Q 1/6855 |
| 11,613,773 B2 | 3/2023 | Frisen et al. | |
| 11,618,897 B2 | 4/2023 | Kim et al. | |
| 11,618,918 B2 | 4/2023 | Chee et al. | |
| 11,624,063 B2 | 4/2023 | Dadhwal | |
| 11,624,086 B2 | 4/2023 | Uytingco et al. | |
| 11,634,756 B2 | 4/2023 | Chee | |
| 11,649,485 B2 | 5/2023 | Yin et al. | |
| 11,661,626 B2 | 5/2023 | Katiraee et al. | |
| 11,680,260 B2 | 6/2023 | Kim et al. | |
| 11,692,218 B2 | 7/2023 | Engblom et al. | |
| 11,702,693 B2 | 7/2023 | Bharadwaj | |
| 11,702,698 B2 | 7/2023 | Stoeckius | |
| 11,713,480 B2 | 8/2023 | Lee | |
| 11,732,292 B2 | 8/2023 | Chee | |
| 11,732,299 B2 | 8/2023 | Ramachandran Iyer | |
| 11,732,300 B2 | 8/2023 | Bava | |
| 11,733,238 B2 | 8/2023 | Chee | |
| 11,739,372 B2 | 8/2023 | Frisen et al. | |
| 11,739,381 B2 | 8/2023 | Chew et al. | |
| 11,753,673 B2 | 9/2023 | Chew et al. | |
| 11,753,674 B2 | 9/2023 | Chee et al. | |
| 11,753,675 B2 | 9/2023 | Ramachandran Iyer | |
| 11,761,030 B2 | 9/2023 | Chee | |
| 11,761,038 B1 | 9/2023 | Stoeckius | |
| 11,767,550 B2 | 9/2023 | Chee | |
| 11,768,175 B1 | 9/2023 | Kim et al. | |
| 11,773,433 B2 | 10/2023 | Gallant et al. | |
| 11,781,130 B2 | 10/2023 | Dadhwal | |
| 11,788,122 B2 | 10/2023 | Frisen et al. | |
| 11,795,498 B2 | 10/2023 | Frisen et al. | |
| 11,795,507 B2 | 10/2023 | Chell et al. | |
| 11,808,769 B2 | 11/2023 | Uytingco et al. | |
| 11,821,024 B2 | 11/2023 | Chee et al. | |
| 11,821,035 B1 | 11/2023 | Bent et al. | |
| 11,827,935 B1 | 11/2023 | Ramachandran Iyer et al. | |
| 11,835,462 B2 | 12/2023 | Bava | |
| 11,840,687 B2 | 12/2023 | Gallant et al. | |
| 11,840,724 B2 | 12/2023 | Chew et al. | |
| 11,845,979 B2 | 12/2023 | Engblom et al. | |
| 11,859,178 B2 | 1/2024 | Gallant et al. | |
| 11,866,767 B2 | 1/2024 | Uytingco et al. | |
| 11,866,770 B2 | 1/2024 | Chee | |
| 11,873,482 B2 | 1/2024 | Kim et al. | |
| 11,891,654 B2 | 2/2024 | Alvarado Martinez et al. | |
| 11,898,205 B2 | 2/2024 | Bava | |
| 11,926,822 B1 | 3/2024 | Gohil et al. | |
| 11,926,863 B1 | 3/2024 | Boutet | |
| 11,926,867 B2 | 3/2024 | Yin et al. | |
| 11,933,957 B1 | 3/2024 | Tentori et al. | |
| 11,952,627 B2 | 4/2024 | Stoeckius | |
| 11,959,076 B2 | 4/2024 | Kim et al. | |
| 11,959,130 B2 * | 4/2024 | Galonska | C12Q 1/6834 |
| 11,965,213 B2 | 4/2024 | Williams | |
| 11,970,739 B2 | 4/2024 | Chew et al. | |
| 11,981,958 B1 | 5/2024 | Galonska | |
| 11,981,960 B1 | 5/2024 | Lin et al. | |
| 11,981,965 B2 * | 5/2024 | Chell | C12Q 1/6841 |
| RE50,065 E | 7/2024 | Frisen et al. | |
| 12,024,741 B2 | 7/2024 | Tentori et al. | |

(56)        References Cited

U.S. PATENT DOCUMENTS

| | | |
|---|---|---|
| 12,031,177 B1 | 7/2024 | Tentori et al. |
| 12,060,604 B2 | 8/2024 | Katiraee et al. |
| 12,071,655 B2 | 8/2024 | Sukovich et al. |
| 12,076,701 B2 | 9/2024 | Bava |
| 12,098,417 B2 | 9/2024 | Engblom et al. |
| 12,098,985 B2 | 9/2024 | Cox et al. |
| 12,110,541 B2 | 10/2024 | Bava |
| 12,117,439 B2 | 10/2024 | Delaney et al. |
| 12,128,403 B2 | 10/2024 | Kim et al. |
| 12,129,516 B2 | 10/2024 | Tentori et al. |
| 12,157,124 B2 | 12/2024 | Cox et al. |
| 12,180,543 B2 | 12/2024 | Uytingco et al. |
| 12,195,790 B2 | 1/2025 | Sukovich et al. |
| 12,203,134 B2 | 1/2025 | Nagendran et al. |
| 12,209,280 B1 | 1/2025 | Mignardi et al. |
| 12,223,751 B2 | 2/2025 | Li et al. |
| 12,228,544 B2 | 2/2025 | Kim et al. |
| 12,234,505 B2 | 2/2025 | Chee |
| 12,241,060 B2 | 3/2025 | Kim et al. |
| 12,241,890 B2 | 3/2025 | Delaney et al. |
| 12,249,085 B2 | 3/2025 | Tentori et al. |
| 12,265,079 B1 | 4/2025 | Bent |
| 12,270,077 B2 | 4/2025 | Schnall-Levin et al. |
| 12,275,988 B2 | 4/2025 | Galonska et al. |
| 12,281,357 B1 | 4/2025 | Tentori et al. |
| 12,286,673 B2 | 4/2025 | Bava |
| 12,287,264 B2 | 4/2025 | Cox et al. |
| 12,297,486 B2 | 5/2025 | Patterson et al. |
| 12,297,487 B2 | 5/2025 | Chee |
| 12,297,488 B2 | 5/2025 | Chee |
| 12,344,892 B2 | 7/2025 | Schnall-Levin et al. |
| 12,365,935 B2 | 7/2025 | Chew et al. |
| 12,365,942 B2 | 7/2025 | Stoeckius |
| 12,371,688 B2 | 7/2025 | Kim et al. |
| 12,378,607 B2 | 8/2025 | Schnall-Levin et al. |
| 12,385,083 B2 | 8/2025 | Shah |
| 12,391,979 B2 | 8/2025 | Chee |
| 12,391,980 B2 | 8/2025 | Chee |
| 12,399,123 B1 | 8/2025 | Shah et al. |
| 12,404,544 B2 | 9/2025 | Tentori et al. |
| 12,405,264 B2 | 9/2025 | Stoeckius |
| 12,416,603 B2 | 9/2025 | Tentori et al. |
| 12,435,363 B1 | 10/2025 | Gallant et al. |
| 12,442,045 B2 | 10/2025 | Williams |
| 2001/0055764 A1 | 12/2001 | Empendocles et al. |
| 2002/0040275 A1 | 4/2002 | Cravatt |
| 2002/0051986 A1 | 5/2002 | Baez et al. |
| 2002/0055100 A1 | 5/2002 | Kawashima |
| 2002/0058250 A1 | 5/2002 | Firth |
| 2002/0086441 A1 | 7/2002 | Baranov et al. |
| 2002/0164611 A1 | 11/2002 | Bamdad |
| 2003/0017451 A1 | 1/2003 | Wang et al. |
| 2003/0022207 A1 | 1/2003 | Balasubramanian |
| 2003/0064398 A1 | 4/2003 | Barnes |
| 2003/0092624 A1 | 5/2003 | Wang et al. |
| 2003/0138879 A1 | 7/2003 | Lambalot |
| 2003/0148335 A1 | 8/2003 | Shen et al. |
| 2003/0162216 A1 | 8/2003 | Gold |
| 2003/0165948 A1 | 9/2003 | Alsmadi et al. |
| 2003/0211489 A1 | 11/2003 | Shen et al. |
| 2003/0224419 A1 | 12/2003 | Corcoran |
| 2003/0232348 A1 | 12/2003 | Jones et al. |
| 2003/0232382 A1 | 12/2003 | Brennan |
| 2003/0235854 A1 | 12/2003 | Chan et al. |
| 2004/0009487 A1 | 1/2004 | Kadushin et al. |
| 2004/0033499 A1 | 2/2004 | Ilsley et al. |
| 2004/0067492 A1 | 4/2004 | Peng et al. |
| 2004/0082059 A1 | 4/2004 | Webb et al. |
| 2004/0096853 A1 | 5/2004 | Mayer |
| 2004/0106110 A1 | 6/2004 | Balasubramanian |
| 2004/0235103 A1 | 11/2004 | Reznikoff et al. |
| 2004/0241660 A1 | 12/2004 | Wojtowicz et al. |
| 2004/0248325 A1 | 12/2004 | Bukusoglu et al. |
| 2004/0259105 A1 | 12/2004 | Fan et al. |
| 2005/0003431 A1 | 1/2005 | Wucherpfennig |
| 2005/0014203 A1 | 1/2005 | Darfler et al. |
| 2005/0037393 A1 | 2/2005 | Gunderson et al. |
| 2005/0048580 A1 | 3/2005 | Labaer |
| 2005/0064460 A1 | 3/2005 | Holliger et al. |
| 2005/0095627 A1 | 5/2005 | Kolman et al. |
| 2005/0100900 A1 | 5/2005 | Kawashima et al. |
| 2005/0130173 A1 | 6/2005 | Leamon et al. |
| 2005/0136414 A1 | 6/2005 | Gunderson et al. |
| 2005/0164292 A1 | 7/2005 | Farooqui |
| 2005/0170373 A1 | 8/2005 | Monforte |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0239119 A1 | 10/2005 | Tsukada et al. |
| 2005/0260653 A1 | 11/2005 | LaBaer |
| 2005/0266417 A1 | 12/2005 | Barany et al. |
| 2006/0041385 A1 | 2/2006 | Bauer et al. |
| 2006/0046313 A1 | 3/2006 | Roth |
| 2006/0084078 A1 | 4/2006 | Zhao |
| 2006/0105352 A1 | 5/2006 | Qiao et al. |
| 2006/0154286 A1 | 7/2006 | Kong et al. |
| 2006/0188901 A1 | 8/2006 | Barnes et al. |
| 2006/0199183 A1 | 9/2006 | Valat et al. |
| 2006/0211001 A1 | 9/2006 | Yu et al. |
| 2006/0216775 A1 | 9/2006 | Burkart et al. |
| 2006/0240439 A1 | 10/2006 | Smith et al. |
| 2006/0263789 A1 | 11/2006 | Kincaid |
| 2006/0275782 A1 | 12/2006 | Gunderson et al. |
| 2006/0281109 A1 | 12/2006 | Barr Ost et al. |
| 2007/0020640 A1 | 1/2007 | McCloskey et al. |
| 2007/0020669 A1 | 1/2007 | Ericsson |
| 2007/0026430 A1 | 2/2007 | Andersen et al. |
| 2007/0054288 A1 | 3/2007 | Su et al. |
| 2007/0087360 A1 | 4/2007 | Boyd |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0134723 A1 | 6/2007 | Kozlov et al. |
| 2007/0161020 A1 | 7/2007 | Luo et al. |
| 2007/0166705 A1 | 7/2007 | Milton et al. |
| 2007/0172873 A1 | 7/2007 | Brenner et al. |
| 2007/0207482 A1 | 9/2007 | Church et al. |
| 2007/0254305 A1 | 11/2007 | Paik et al. |
| 2007/0269805 A1 | 11/2007 | Hogers |
| 2008/0003586 A1 | 1/2008 | Hyde et al. |
| 2008/0009420 A1 | 1/2008 | Schroth et al. |
| 2008/0108082 A1 | 5/2008 | Rank et al. |
| 2008/0108804 A1 | 5/2008 | Hayashizaki et al. |
| 2008/0132429 A1 | 6/2008 | Perov et al. |
| 2008/0160580 A1 | 7/2008 | Adessi et al. |
| 2008/0220434 A1 | 9/2008 | Thomas |
| 2008/0261204 A1 | 10/2008 | Lexow |
| 2008/0286795 A1 | 11/2008 | Kawashima et al. |
| 2008/0293046 A1 | 11/2008 | Allawi et al. |
| 2009/0005252 A1 | 1/2009 | Drmanac et al. |
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0036323 A1 | 2/2009 | van Eijk et al. |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0170713 A1 | 7/2009 | van Eijk et al. |
| 2009/0202998 A1 | 8/2009 | Schlumpberger et al. |
| 2009/0233802 A1 | 9/2009 | Bignell et al. |
| 2009/0253581 A1 | 10/2009 | Van Eijk et al. |
| 2009/0270273 A1 | 10/2009 | Burns et al. |
| 2009/0283407 A1 | 11/2009 | Shah et al. |
| 2009/0286249 A1 | 11/2009 | Becker et al. |
| 2009/0291854 A1 | 11/2009 | Weisinger-Mayr et al. |
| 2009/0312193 A1 | 12/2009 | Kim et al. |
| 2010/0035249 A1 | 2/2010 | Hayashizaki et al. |
| 2010/0047790 A1 | 2/2010 | Southern et al. |
| 2010/0069263 A1 | 3/2010 | Shendure et al. |
| 2010/0105052 A1 | 4/2010 | Drmanac et al. |

(56) References Cited

U.S. PATENT DOCUMENTS

| | | | |
|---|---|---|---|
| 2010/0120097 A1 | 5/2010 | Matz et al. |
| 2010/0120098 A1 | 5/2010 | Grunenwald et al. |
| 2010/0129874 A1 | 5/2010 | Mitra et al. |
| 2010/0145037 A1 | 6/2010 | Brive et al. |
| 2010/0173384 A1 | 7/2010 | Johnsson et al. |
| 2010/0184618 A1 | 7/2010 | Namsaraev et al. |
| 2010/0210475 A1 | 8/2010 | Lee et al. |
| 2010/0227329 A1 | 9/2010 | Cuppens |
| 2010/0273219 A1 | 10/2010 | May et al. |
| 2011/0028685 A1 | 2/2011 | Purkayastha et al. |
| 2011/0031123 A1 | 2/2011 | Schulze et al. |
| 2011/0033854 A1 | 2/2011 | Drmanac et al. |
| 2011/0045462 A1 | 2/2011 | Fu et al. |
| 2011/0059436 A1 | 3/2011 | Hardin et al. |
| 2011/0111409 A1 | 5/2011 | Sinicropi et al. |
| 2011/0152111 A1 | 6/2011 | Fan et al. |
| 2011/0237449 A1 | 9/2011 | McMaster et al. |
| 2011/0245101 A1 | 10/2011 | Chee et al. |
| 2011/0245111 A1 | 10/2011 | Chee |
| 2011/0287435 A1 | 11/2011 | Grunenwald et al. |
| 2012/0021930 A1 | 1/2012 | Schoen et al. |
| 2012/0046175 A1 | 2/2012 | Rodesch et al. |
| 2012/0046178 A1 | 2/2012 | Van Den Boom et al. |
| 2012/0065081 A1 | 3/2012 | Chee |
| 2012/0135871 A1 | 5/2012 | Van Eijk et al. |
| 2012/0202698 A1 | 8/2012 | Van Eijk et al. |
| 2012/0202704 A1 | 8/2012 | Fan et al. |
| 2012/0220479 A1 | 8/2012 | Ericsson et al. |
| 2012/0245053 A1 | 9/2012 | Shirai et al. |
| 2012/0252702 A1 | 10/2012 | Muratani et al. |
| 2012/0258871 A1 | 10/2012 | Kozlov et al. |
| 2012/0289414 A1 | 11/2012 | Mitra et al. |
| 2012/0301925 A1 | 11/2012 | Belyaev |
| 2013/0005594 A1 | 1/2013 | Terbrueggen et al. |
| 2013/0005600 A1 | 1/2013 | Olek |
| 2013/0023433 A1 | 1/2013 | Luo et al. |
| 2013/0035239 A1 | 2/2013 | Kong et al. |
| 2013/0040842 A1 | 2/2013 | Lim et al. |
| 2013/0065768 A1 | 3/2013 | Zheng et al. |
| 2013/0079232 A1 | 3/2013 | Kain et al. |
| 2013/0171621 A1 | 7/2013 | Luo et al. |
| 2013/0244884 A1 | 9/2013 | Jacobson et al. |
| 2013/0261019 A1 | 10/2013 | Lin et al. |
| 2013/0302801 A1 | 11/2013 | Asbury et al. |
| 2013/0338042 A1 | 12/2013 | Shen et al. |
| 2014/0066318 A1 | 3/2014 | Frisen et al. |
| 2014/0121118 A1 | 5/2014 | Warner |
| 2014/0270435 A1 | 9/2014 | Dunn |
| 2014/0274731 A1 | 9/2014 | Raymond et al. |
| 2014/0323330 A1 | 10/2014 | Glezer et al. |
| 2014/0342921 A1 | 11/2014 | Weiner |
| 2014/0378350 A1 | 12/2014 | Hindson et al. |
| 2015/0292988 A1 | 10/2015 | Bharadwaj et al. |
| 2015/0344942 A1 | 12/2015 | Frisen et al. |
| 2016/0019337 A1 | 1/2016 | Roberts et al. |
| 2016/0024576 A1 | 1/2016 | Chee |
| 2016/0041159 A1 | 2/2016 | Labaer et al. |
| 2016/0060687 A1 | 3/2016 | Zhu et al. |
| 2016/0108458 A1 | 4/2016 | Frei et al. |
| 2016/0122817 A1 | 5/2016 | Jarosz et al. |
| 2016/0138091 A1 | 5/2016 | Chee et al. |
| 2016/0145677 A1 | 5/2016 | Chee et al. |
| 2016/0194692 A1 | 7/2016 | Gore et al. |
| 2016/0201125 A1 | 7/2016 | Samuels et al. |
| 2016/0253584 A1 | 9/2016 | Fodor et al. |
| 2016/0289740 A1 | 10/2016 | Fu et al. |
| 2016/0298180 A1 | 10/2016 | Chee |
| 2016/0305856 A1 | 10/2016 | Boyden et al. |
| 2016/0312276 A1 | 10/2016 | Fu et al. |
| 2016/0333403 A1 | 11/2016 | Chee |
| 2016/0376642 A1 | 12/2016 | Landegren et al. |
| 2017/0009278 A1 | 1/2017 | Söderberg et al. |
| 2017/0016053 A1 | 1/2017 | Beechem et al. |
| 2017/0029875 A1 | 2/2017 | Zhang et al. |
| 2017/0058339 A1 | 3/2017 | Chee |
| 2017/0058340 A1 | 3/2017 | Chee |
| 2017/0058345 A1 | 3/2017 | Chee |
| 2017/0067096 A1 | 3/2017 | Wassie et al. |
| 2017/0088881 A1 | 3/2017 | Chee |
| 2017/0089811 A1 | 3/2017 | Tillberg et al. |
| 2017/0159109 A1 | 6/2017 | Zheng et al. |
| 2017/0166962 A1 | 6/2017 | van Eijk et al. |
| 2017/0220733 A1 | 8/2017 | Zhuang et al. |
| 2017/0233722 A1 | 8/2017 | Seelig et al. |
| 2017/0241911 A1 | 8/2017 | Rockel et al. |
| 2017/0283860 A1 | 10/2017 | Kool et al. |
| 2017/0335297 A1 | 11/2017 | Ha et al. |
| 2017/0335410 A1 | 11/2017 | Driscoll et al. |
| 2017/0342405 A1 | 11/2017 | Fu et al. |
| 2017/0349940 A1 | 12/2017 | Morin et al. |
| 2018/0051322 A1 | 2/2018 | Church et al. |
| 2018/0057873 A1 | 3/2018 | Zhou et al. |
| 2018/0080019 A1 | 3/2018 | Blainey et al. |
| 2018/0088112 A1 | 3/2018 | Fan et al. |
| 2018/0094316 A1 | 4/2018 | Oliphant et al. |
| 2018/0112261 A1 | 4/2018 | Van Driel et al. |
| 2018/0127817 A1 | 5/2018 | Borchert et al. |
| 2018/0163265 A1 | 6/2018 | Zhang et al. |
| 2018/0179591 A1 | 6/2018 | van Eijk |
| 2018/0201925 A1 | 7/2018 | Steemers et al. |
| 2018/0201980 A1 | 7/2018 | Chee et al. |
| 2018/0208967 A1 | 7/2018 | Larman et al. |
| 2018/0216161 A1 | 8/2018 | Chen et al. |
| 2018/0216162 A1 | 8/2018 | Belhocine et al. |
| 2018/0237864 A1 | 8/2018 | Imler et al. |
| 2018/0245142 A1 | 8/2018 | So et al. |
| 2018/0247017 A1 | 8/2018 | van Eijk et al. |
| 2018/0291427 A1 | 10/2018 | Edelman |
| 2018/0291439 A1 | 10/2018 | van Eijk et al. |
| 2018/0305681 A1 | 10/2018 | Jovanovich et al. |
| 2018/0312822 A1 | 11/2018 | Lee et al. |
| 2018/0320226 A1 | 11/2018 | Church et al. |
| 2019/0055594 A1 | 2/2019 | Samusik et al. |
| 2019/0064173 A1 | 2/2019 | Bharadwaj et al. |
| 2019/0071656 A1 | 3/2019 | Chang et al. |
| 2019/0085383 A1 | 3/2019 | Church et al. |
| 2019/0119735 A1 | 4/2019 | Deisseroth et al. |
| 2019/0135774 A1 | 5/2019 | Orbai |
| 2019/0145982 A1 | 5/2019 | Chee et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0177800 A1 | 6/2019 | Boutet et al. |
| 2019/0194709 A1 | 6/2019 | Church et al. |
| 2019/0203275 A1 | 7/2019 | Frisen et al. |
| 2019/0218276 A1 | 7/2019 | Regev et al. |
| 2019/0218608 A1 | 7/2019 | Daugharthy et al. |
| 2019/0233878 A1 | 8/2019 | Delaney et al. |
| 2019/0233880 A1 | 8/2019 | Mir |
| 2019/0249226 A1 | 8/2019 | Bent et al. |
| 2019/0262831 A1 | 8/2019 | West et al. |
| 2019/0264268 A1 | 8/2019 | Frisen et al. |
| 2019/0271028 A1 | 9/2019 | Khafizov et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0323088 A1 | 10/2019 | Boutet et al. |
| 2019/0330617 A1 | 10/2019 | Church et al. |
| 2019/0338353 A1 | 11/2019 | Belgrader et al. |
| 2019/0360034 A1 | 11/2019 | Zhou et al. |
| 2019/0360043 A1 | 11/2019 | Pham et al. |
| 2019/0367969 A1 | 12/2019 | Belhocine et al. |
| 2019/0367982 A1 | 12/2019 | Belhocine et al. |
| 2019/0367997 A1 | 12/2019 | Bent et al. |
| 2020/0002763 A1 | 1/2020 | Belgrader et al. |
| 2020/0010891 A1 | 1/2020 | Beechem et al. |
| 2020/0024641 A1 | 1/2020 | Nolan et al. |

(56) References Cited

U.S. PATENT DOCUMENTS

| | | |
|---|---|---|
| 2020/0047010 A1 | 2/2020 | Lee et al. |
| 2020/0048690 A1 | 2/2020 | Chee |
| 2020/0063191 A1 | 2/2020 | Kennedy-Darling et al. |
| 2020/0063195 A1 | 2/2020 | Chee |
| 2020/0063196 A1 | 2/2020 | Chee |
| 2020/0071751 A1 | 3/2020 | Daugharthy et al. |
| 2020/0080136 A1 | 3/2020 | Zhang et al. |
| 2020/0109443 A1 | 4/2020 | Chee |
| 2020/0123597 A1 | 4/2020 | Daniel |
| 2020/0131570 A1 | 4/2020 | Berti et al. |
| 2020/0140920 A1 | 5/2020 | Pierce et al. |
| 2020/0173985 A1 | 6/2020 | Dong et al. |
| 2020/0199565 A1 | 6/2020 | Chen et al. |
| 2020/0199572 A1 | 6/2020 | Kuersten et al. |
| 2020/0224244 A1 | 7/2020 | Nilsson et al. |
| 2020/0239874 A1 | 7/2020 | Mikkelsen |
| 2020/0239946 A1 | 7/2020 | Dewal |
| 2020/0256867 A1 | 8/2020 | Hennek et al. |
| 2020/0277663 A1 | 9/2020 | Iyer |
| 2020/0277664 A1 | 9/2020 | Frenz |
| 2020/0283852 A1 | 9/2020 | Oliphant et al. |
| 2020/0299757 A1 | 9/2020 | Chee et al. |
| 2020/0325531 A1 | 10/2020 | Chee |
| 2020/0362398 A1 | 11/2020 | Kishi et al. |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0017587 A1 | 1/2021 | Cai et al. |
| 2021/0095331 A1 | 4/2021 | Fan et al. |
| 2021/0115504 A1 | 4/2021 | Cai et al. |
| 2021/0123040 A1 | 4/2021 | Macosko et al. |
| 2021/0130881 A1 | 5/2021 | Cox |
| 2021/0140982 A1 | 5/2021 | Uytingco et al. |
| 2021/0150707 A1 | 5/2021 | Weisenfeld et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0190770 A1 | 6/2021 | Delaney et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0237022 A1 | 8/2021 | Bava |
| 2021/0238581 A1 | 8/2021 | Mikkelsen et al. |
| 2021/0238664 A1 | 8/2021 | Bava et al. |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0277460 A1 | 9/2021 | Bava |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0106633 A1 | 4/2022 | Engblom et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1* | 4/2022 | Katiraee ............. C12Q 1/6876 |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0220544 A1 | 7/2022 | Ach et al. |
| 2022/0241780 A1 | 8/2022 | Tentori et al. |
| 2022/0267844 A1 | 8/2022 | Ramachandran Iyer et al. |
| 2022/0282329 A1 | 9/2022 | Chell et al. |
| 2022/0290217 A1 | 9/2022 | Frenz et al. |
| 2022/0290219 A1 | 9/2022 | Chee |
| 2022/0298560 A1 | 9/2022 | Frisen et al. |
| 2022/0325325 A1 | 10/2022 | Chee et al. |
| 2022/0326251 A1 | 10/2022 | Uytingco et al. |
| 2022/0333171 A1 | 10/2022 | Chee |
| 2022/0333191 A1 | 10/2022 | Mikkelsen et al. |
| 2022/0333192 A1 | 10/2022 | Uytingco |
| 2022/0333195 A1 | 10/2022 | Schnall-Levin et al. |
| 2022/0334031 A1 | 10/2022 | Delaney et al. |
| 2022/0348905 A1 | 11/2022 | Dadhwal |
| 2022/0348992 A1 | 11/2022 | Stoeckius et al. |
| 2022/0356464 A1 | 11/2022 | Kim et al. |
| 2022/0364163 A1 | 11/2022 | Stahl et al. |
| 2022/0389491 A1 | 12/2022 | Chee |
| 2022/0389503 A1 | 12/2022 | Mikkelsen et al. |
| 2022/0389504 A1 | 12/2022 | Chew et al. |
| 2022/0403455 A1 | 12/2022 | Ramachandran Iyer et al. |
| 2022/0404245 A1 | 12/2022 | Chell et al. |
| 2023/0002812 A1 | 1/2023 | Stoeckius et al. |
| 2023/0014008 A1 | 1/2023 | Shastry |
| 2023/0017773 A1 | 1/2023 | Kim et al. |
| 2023/0031305 A1 | 2/2023 | Neuta et al. |
| 2023/0033960 A1 | 2/2023 | Gallant et al. |
| 2023/0034039 A1 | 2/2023 | Shahjamali |
| 2023/0034216 A1 | 2/2023 | Bava |
| 2023/0040363 A1 | 2/2023 | Chee |
| 2023/0042088 A1 | 2/2023 | Chee |
| 2023/0042817 A1 | 2/2023 | Mignardi |
| 2023/0047782 A1 | 2/2023 | Tentori et al. |
| 2023/0056549 A1 | 2/2023 | Dadhwal |
| 2023/0064372 A1 | 3/2023 | Chell et al. |
| 2023/0069046 A1 | 3/2023 | Chew et al. |
| 2023/0077364 A1 | 3/2023 | Patterson et al. |
| 2023/0080543 A1 | 3/2023 | Katiraee et al. |
| 2023/0081381 A1 | 3/2023 | Chew et al. |
| 2023/0100497 A1 | 3/2023 | Frisen et al. |
| 2023/0107023 A1 | 4/2023 | Chee |
| 2023/0111225 A1 | 4/2023 | Chew et al. |
| 2023/0113230 A1 | 4/2023 | Kim et al. |
| 2023/0126825 A1 | 4/2023 | Nagendran et al. |
| 2023/0129552 A1 | 4/2023 | Ramachandran Iyer |
| 2023/0135010 A1 | 5/2023 | Tentori et al. |
| 2023/0143569 A1 | 5/2023 | Iyer et al. |
| 2023/0145575 A1 | 5/2023 | Gallant et al. |
| 2023/0147726 A1 | 5/2023 | Hadrup et al. |

(56) References Cited

U.S. PATENT DOCUMENTS

| 2023/0151412 A1 | 5/2023 | Chee |
| 2023/0159994 A1 | 5/2023 | Chee |
| 2023/0159995 A1 | 5/2023 | Iyer et al. |
| 2023/0160008 A1 | 5/2023 | Chell et al. |
| 2023/0175045 A1 | 6/2023 | Katsori et al. |
| 2023/0183684 A1 | 6/2023 | Gallant et al. |
| 2023/0183785 A1 | 6/2023 | Frisen et al. |
| 2023/0194469 A1 | 6/2023 | Tentori et al. |
| 2023/0194470 A1 | 6/2023 | Kim et al. |
| 2023/0203478 A1 | 6/2023 | Kim et al. |
| 2023/0212650 A1 | 7/2023 | Chew et al. |
| 2023/0212655 A1 | 7/2023 | Chee |
| 2023/0212656 A1 | 7/2023 | Chow et al. |
| 2023/0220368 A1 | 7/2023 | Kim |
| 2023/0220454 A1 | 7/2023 | Bent et al. |
| 2023/0220455 A1 | 7/2023 | Galonska et al. |
| 2023/0227811 A1 | 7/2023 | Dadhwal |
| 2023/0228762 A1 | 7/2023 | Uytingco et al. |
| 2023/0242973 A1 | 8/2023 | Frisen et al. |
| 2023/0242976 A1 | 8/2023 | Tentori et al. |
| 2023/0265488 A1 | 8/2023 | Gohil et al. |
| 2023/0265489 A1 | 8/2023 | Uytingco et al. |
| 2023/0265491 A1 | 8/2023 | Tentori et al. |
| 2023/0267625 A1 | 8/2023 | Tentori et al. |
| 2023/0279474 A1 | 9/2023 | Katiraee |
| 2023/0279477 A1 | 9/2023 | Kvastad et al. |
| 2023/0279481 A1 | 9/2023 | Marrache et al. |
| 2023/0287399 A1 | 9/2023 | Gallant et al. |
| 2023/0287475 A1 | 9/2023 | Chell et al. |
| 2023/0287481 A1 | 9/2023 | Katsori et al. |
| 2023/0295699 A1 | 9/2023 | Sukovich et al. |
| 2023/0295722 A1 | 9/2023 | Bharadwaj |
| 2023/0304072 A1 | 9/2023 | Gohil et al. |
| 2023/0304074 A1 | 9/2023 | Chee et al. |
| 2023/0304078 A1 | 9/2023 | Frisen et al. |
| 2023/0313279 A1 | 10/2023 | Giacomello et al. |
| 2023/0323340 A1 | 10/2023 | Dadhwal |
| 2023/0323434 A1 | 10/2023 | Yin et al. |
| 2023/0323436 A1 | 10/2023 | Chee |
| 2023/0323447 A1 | 10/2023 | Schnall-Levin et al. |
| 2023/0323453 A1 | 10/2023 | Stoeckius |
| 2023/0332138 A1 | 10/2023 | Kim et al. |
| 2023/0332211 A1 | 10/2023 | Chee |
| 2023/0332212 A1 | 10/2023 | Chew et al. |
| 2023/0332227 A1 | 10/2023 | Ramachandran Iyer |
| 2023/0332247 A1 | 10/2023 | Singh et al. |
| 2023/0351619 A1 | 11/2023 | Tentori et al. |
| 2023/0358733 A1 | 11/2023 | Chee |
| 2023/0366008 A1 | 11/2023 | Chew et al. |
| 2023/0383285 A1 | 11/2023 | Kim et al. |
| 2023/0383344 A1 | 11/2023 | Stoeckius |
| 2023/0392204 A1 | 12/2023 | Chell et al. |
| 2023/0393071 A1 | 12/2023 | Bava |
| 2023/0407404 A1 | 12/2023 | Baumgartner et al. |
| 2023/0416807 A1 | 12/2023 | Chee |
| 2023/0416808 A1 | 12/2023 | Sukovich et al. |
| 2023/0416850 A1 | 12/2023 | Singh et al. |
| 2024/0002931 A1 | 1/2024 | Bava |
| 2024/0011081 A1 | 1/2024 | Chee |
| 2024/0011090 A1 | 1/2024 | Chew et al. |
| 2024/0018572 A1 | 1/2024 | Mignardi |
| 2024/0018575 A1 | 1/2024 | Gallant et al. |
| 2024/0018589 A1 | 1/2024 | Schnall-Levin et al. |
| 2024/0026445 A1 | 1/2024 | Ramachandran Iyer et al. |
| 2024/0033743 A1 | 2/2024 | Tentori et al. |
| 2024/0035937 A1 | 2/2024 | Cox et al. |
| 2024/0043908 A1 | 2/2024 | Chew et al. |
| 2024/0043925 A1 | 2/2024 | Bent et al. |
| 2024/0052343 A1 | 2/2024 | Gallant et al. |
| 2024/0053351 A1 | 2/2024 | Uytingco et al. |
| 2024/0060115 A1 | 2/2024 | Chee et al. |
| 2024/0067953 A1 | 2/2024 | Mikkelsen et al. |
| 2024/0068016 A1 | 2/2024 | Frisen et al. |
| 2024/0068017 A1 | 2/2024 | Lundeberg et al. |
| 2024/0076723 A1 | 3/2024 | Mignardi |
| 2024/0080346 A1 | 3/2024 | Engblom et al. |
| 2024/0084365 A1 | 3/2024 | Frisen et al. |
| 2024/0084366 A1 | 3/2024 | Chee |
| 2024/0084383 A1 | 3/2024 | Ramachandran Iyer et al. |
| 2024/0093274 A1 | 3/2024 | Frisen et al. |
| 2024/0093290 A1 | 3/2024 | Stahl et al. |
| 2024/0110228 A1 | 4/2024 | Uytingco et al. |
| 2024/0124933 A1 | 4/2024 | Chell et al. |
| 2024/0125772 A1 | 4/2024 | Delaney et al. |
| 2024/0141327 A1 | 5/2024 | Kim et al. |
| 2024/0158838 A1 | 5/2024 | Alvarado Martinez et al. |
| 2024/0175080 A1 | 5/2024 | Galonska et al. |
| 2024/0182968 A1 | 6/2024 | Bava |
| 2024/0191286 A1 | 6/2024 | Boutet et al. |
| 2024/0200121 A1 | 6/2024 | Boutet |
| 2024/0209425 A1 | 6/2024 | Yin et al. |
| 2024/0218427 A1 | 7/2024 | Sukovich et al. |
| 2024/0218432 A1 | 7/2024 | Mielinis |
| 2024/0219701 A1 | 7/2024 | Tentori et al. |
| 2024/0253036 A1 | 8/2024 | Kim et al. |
| 2024/0263218 A1 | 8/2024 | Katiraee et al. |
| 2024/0271190 A1 | 8/2024 | Stoeckius et al. |
| 2024/0271195 A1 | 8/2024 | Mikhaiel et al. |
| 2024/0279747 A1 | 8/2024 | Williams |
| 2024/0287600 A1 | 8/2024 | Iyer et al. |
| 2024/0294971 A1 | 9/2024 | Galonska |
| 2024/0294974 A1 | 9/2024 | Galonska et al. |
| 2024/0294975 A1 | 9/2024 | Lin et al. |
| 2024/0301488 A1 | 9/2024 | Stoeckius |
| 2024/0301489 A1 | 9/2024 | Chew et al. |
| 2024/0360494 A1 | 10/2024 | Costa et al. |
| 2024/0368711 A1 | 11/2024 | Giacomello et al. |
| 2024/0377297 A1 | 11/2024 | Cox et al. |
| 2024/0385088 A1 | 11/2024 | Kim et al. |
| 2024/0392349 A1 | 11/2024 | Frisen et al. |
| 2024/0392351 A1 | 11/2024 | Chee |
| 2024/0392352 A1 | 11/2024 | Stahl et al. |
| 2024/0392353 A1 | 11/2024 | Engblom et al. |
| 2024/0401109 A1 | 12/2024 | Kim et al. |
| 2024/0401117 A1 | 12/2024 | Bava |
| 2024/0401118 A1 | 12/2024 | Tentori et al. |
| 2024/0404301 A1 | 12/2024 | Li et al. |
| 2024/0408593 A1 | 12/2024 | Kim et al. |
| 2024/0416315 A1 | 12/2024 | Bava |
| 2024/0417783 A1 | 12/2024 | Chew et al. |
| 2024/0417784 A1 | 12/2024 | Sukovich et al. |
| 2025/0002980 A1 | 1/2025 | Tentori et al. |
| 2025/0002982 A1 | 1/2025 | Stoeckius et al. |
| 2025/0003956 A1 | 1/2025 | Delaney et al. |
| 2025/0019689 A1 | 1/2025 | Galonska et al. |
| 2025/0019749 A1 | 1/2025 | Katiraee et al. |
| 2025/0066762 A1 | 2/2025 | Man et al. |
| 2025/0066770 A1 | 2/2025 | Costa |
| 2025/0073719 A1 | 3/2025 | Cox et al. |
| 2025/0075261 A1 | 3/2025 | Kim |
| 2025/0101501 A1 | 3/2025 | Chee |
| 2025/0101502 A1 | 3/2025 | Chee |
| 2025/0101504 A1 | 3/2025 | Nagendran et al. |
| 2025/0122564 A1 | 4/2025 | Mignardi et al. |
| 2025/0122565 A1 | 4/2025 | Schnall-Levin et al. |
| 2025/0129412 A1 | 4/2025 | Uytingco et al. |
| 2025/0129421 A1 | 4/2025 | Schnall-Levin et al. |
| 2025/0137043 A1 | 5/2025 | Tentori |
| 2025/0145984 A1 | 5/2025 | Ma et al. |
| 2025/0146057 A1 | 5/2025 | Schnall-Levin et al. |
| 2025/0146058 A1 | 5/2025 | Tentori |
| 2025/0146071 A1 | 5/2025 | Schnall-Levin et al. |
| 2025/0146072 A1 | 5/2025 | Schnall-Levin et al. |
| 2025/0154565 A1 | 5/2025 | Chee |
| 2025/0154566 A1 | 5/2025 | Chee |
| 2025/0154567 A1 | 5/2025 | Chee |
| 2025/0154568 A1 | 5/2025 | Frisen et al. |
| 2025/0154569 A1 | 5/2025 | Stoeckius et al. |
| 2025/0154571 A1 | 5/2025 | Ramachandran Iyer et al. |
| 2025/0154588 A1 | 5/2025 | Ramachandran Iyer et al. |
| 2025/0155446 A1 | 5/2025 | Uytingco et al. |
| 2025/0163501 A1 | 5/2025 | Singh et al. |
| 2025/0163509 A1 | 5/2025 | Daugharthy et al. |
| 2025/0171833 A1 | 5/2025 | Frisen et al. |

(56) References Cited

U.S. PATENT DOCUMENTS

| | | |
|---|---|---|
| 2025/0171848 A1 | 5/2025 | Chell et al. |
| 2025/0179475 A1 | 6/2025 | Borgstrom et al. |
| 2025/0182305 A1 | 6/2025 | Tentori et al. |
| 2025/0182503 A1 | 6/2025 | Li et al. |
| 2025/0188526 A1 | 6/2025 | Sukovich et al. |
| 2025/0189483 A1 | 6/2025 | Kim et al. |
| 2025/0197847 A1 | 6/2025 | Kim et al. |
| 2025/0197938 A1 | 6/2025 | Bjorninen |
| 2025/0207125 A1 | 6/2025 | Gupta et al. |
| 2025/0207182 A1 | 6/2025 | Chee |
| 2025/0207183 A1 | 6/2025 | Chee |
| 2025/0207195 A1 | 6/2025 | Chell et al. |
| 2025/0208115 A1 | 6/2025 | Bent |
| 2025/0215482 A1 | 7/2025 | Mignardi et al. |
| 2025/0215484 A1 | 7/2025 | Ramachandran Iyer et al. |
| 2025/0216300 A1 | 7/2025 | Delaney et al. |
| 2025/0216303 A1 | 7/2025 | Cox et al. |
| 2025/0223633 A1 | 7/2025 | Frenz et al. |
| 2025/0230487 A1 | 7/2025 | Chee et al. |
| 2025/0230498 A1 | 7/2025 | Katiraee |
| 2025/0250621 A1 | 8/2025 | Galonska et al. |
| 2025/0250632 A1 | 8/2025 | Mignardi et al. |
| 2025/0257393 A1 | 8/2025 | Katiraee et al. |
| 2025/0263791 A1 | 8/2025 | Bava |
| 2025/0264411 A1 | 8/2025 | Bava |
| 2025/0283154 A1 | 9/2025 | Ramachandran Iyer et al. |
| 2025/0283157 A1 | 9/2025 | Uytingco et al. |
| 2025/0297308 A1 | 9/2025 | Tentori |
| 2025/0313890 A1 | 10/2025 | Lundeberg et al. |
| 2025/0313892 A1 | 10/2025 | Stoeckius |
| 2025/0340932 A1 | 11/2025 | Chee |
| 2025/0340933 A1 | 11/2025 | Giacomello et al. |
| 2025/0354931 A1 | 11/2025 | Shah et al. |
| 2025/0369037 A1 | 12/2025 | Gupta |
| 2025/0376676 A1 | 12/2025 | Kim et al. |
| 2025/0376719 A1 | 12/2025 | Shah |

FOREIGN PATENT DOCUMENTS

| | | |
|---|---|---|
| CN | 1537953 | 10/2004 |
| CN | 1680604 | 10/2005 |
| CN | 1749752 | 3/2006 |
| CN | 1898398 | 1/2007 |
| CN | 101142325 | 3/2008 |
| CN | 101221182 | 7/2008 |
| CN | 101522915 | 9/2009 |
| CN | 107849606 | 3/2018 |
| CN | 108949924 | 12/2018 |
| EP | 1782737 | 5/2007 |
| EP | 1910562 | 4/2008 |
| EP | 1923471 | 5/2008 |
| EP | 1929039 | 6/2008 |
| EP | 2002017 | 12/2008 |
| EP | 2130913 | 12/2009 |
| EP | 2292788 | 3/2011 |
| EP | 2302070 | 3/2011 |
| EP | 2580351 | 4/2013 |
| EP | 2881465 | 6/2015 |
| EP | 3013984 | 5/2016 |
| EP | 3207134 | 7/2019 |
| EP | 3511423 | 7/2019 |
| EP | 3541956 | 9/2019 |
| GB | 2520765 | 6/2015 |
| JP | 2007-014297 | 1/2007 |
| JP | 2007-074967 | 3/2007 |
| JP | 2009-036694 | 2/2009 |
| WO | WO 1989/010977 | 11/1989 |
| WO | WO 1991/006678 | 5/1991 |
| WO | WO 1993/004199 | 3/1993 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 1998/044151 | 10/1998 |
| WO | WO 2000/017390 | 3/2000 |
| WO | WO 2000/063437 | 10/2000 |
| WO | WO 2001/006012 | 1/2001 |
| WO | WO 2001/009363 | 2/2001 |
| WO | WO 2001/012862 | 2/2001 |
| WO | WO 2001/042796 | 6/2001 |
| WO | WO 2001/046402 | 6/2001 |
| WO | WO 2001/059161 | 8/2001 |
| WO | WO 2001/090415 | 11/2001 |
| WO | WO 2001/096608 | 12/2001 |
| WO | WO 2002/040874 | 5/2002 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2004/015080 | 2/2004 |
| WO | WO 2004/067759 | 8/2004 |
| WO | WO 2004/081225 | 9/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/113804 | 12/2005 |
| WO | WO 2006/020515 | 2/2006 |
| WO | WO 2006/124771 | 11/2006 |
| WO | WO 2006/137733 | 12/2006 |
| WO | WO 2007/037678 | 4/2007 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/139766 | 12/2007 |
| WO | WO 2007/145612 | 12/2007 |
| WO | WO 2008/069906 | 6/2008 |
| WO | WO 2008/075086 | 6/2008 |
| WO | WO 2008/093098 | 8/2008 |
| WO | WO 2009/032167 | 3/2009 |
| WO | WO 2009/036525 | 3/2009 |
| WO | WO 2009/137521 | 11/2009 |
| WO | WO 2009/152928 | 12/2009 |
| WO | WO 2010/019826 | 2/2010 |
| WO | WO 2010/027870 | 3/2010 |
| WO | WO 2010/088517 | 8/2010 |
| WO | WO 2010/126614 | 11/2010 |
| WO | WO 2010/127186 | 11/2010 |
| WO | WO 2011/008502 | 1/2011 |
| WO | WO 2011/019964 | 2/2011 |
| WO | WO 2011/062933 | 5/2011 |
| WO | WO 2011/068088 | 6/2011 |
| WO | WO 2011/127006 | 10/2011 |
| WO | WO 2011/155833 | 12/2011 |
| WO | WO 2012/049316 | 4/2012 |
| WO | WO 2012/061832 | 5/2012 |
| WO | WO 2012/071428 | 5/2012 |
| WO | WO 2012/129242 | 9/2012 |
| WO | WO 2012/159089 | 11/2012 |
| WO | WO 2013/022807 | 2/2013 |
| WO | WO 2013/123442 | 8/2013 |
| WO | WO 2013/131962 | 9/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2013/192292 | 12/2013 |
| WO | WO 2014/044724 | 3/2014 |
| WO | WO 2014/060483 | 4/2014 |
| WO | WO 2014/071361 | 5/2014 |
| WO | WO 2014/130576 | 8/2014 |
| WO | WO 2014/144713 | 9/2014 |
| WO | WO 2014/152397 | 9/2014 |
| WO | WO 2014/210223 | 12/2014 |
| WO | WO 2014/210353 | 12/2014 |
| WO | WO 2015/031691 | 3/2015 |
| WO | WO 2015/069374 | 5/2015 |
| WO | WO 2015/161173 | 10/2015 |
| WO | WO 2016/077763 | 5/2016 |
| WO | WO 2016/100196 | 6/2016 |

(56)             References Cited

FOREIGN PATENT DOCUMENTS

| | | |
|---|---|---|
| WO | WO 2016/138496 | 9/2016 |
| WO | WO 2016/138500 | 9/2016 |
| WO | WO 2016/162309 | 10/2016 |
| WO | WO 2016/166128 | 10/2016 |
| WO | WO 2016/168825 | 10/2016 |
| WO | WO 2016/172362 | 10/2016 |
| WO | WO 2017/019456 | 2/2017 |
| WO | WO 2017/019481 | 2/2017 |
| WO | WO 2017/044993 | 3/2017 |
| WO | WO 2017/075293 | 5/2017 |
| WO | WO 2017/096158 | 7/2017 |
| WO | WO 2017/143155 | 8/2017 |
| WO | WO 2017/156336 | 9/2017 |
| WO | WO 2017/184984 | 10/2017 |
| WO | WO 2017/192633 | 11/2017 |
| WO | WO 2018/023068 | 2/2018 |
| WO | WO 2018/026873 | 2/2018 |
| WO | WO 2018/045181 | 3/2018 |
| WO | WO 2018/064640 | 4/2018 |
| WO | WO 2018/085599 | 5/2018 |
| WO | WO 2018/089550 | 5/2018 |
| WO | WO 2018/091676 | 5/2018 |
| WO | WO 2018/136397 | 7/2018 |
| WO | WO 2018/136856 | 7/2018 |
| WO | WO 2018/144582 | 8/2018 |
| WO | WO 2018/175779 | 9/2018 |
| WO | WO 2018/209398 | 11/2018 |
| WO | WO 2019/023214 | 1/2019 |
| WO | WO 2019/032760 | 2/2019 |
| WO | WO 2019/068880 | 4/2019 |
| WO | WO 2019/113457 | 6/2019 |
| WO | WO 2019/126313 | 6/2019 |
| WO | WO 2019/140201 | 7/2019 |
| WO | WO 2019/165318 | 8/2019 |
| WO | WO 2019/213254 | 11/2019 |
| WO | WO 2019/213294 | 11/2019 |
| WO | WO 2019/241290 | 12/2019 |
| WO | WO 2020/028194 | 2/2020 |
| WO | WO 2020/047002 | 3/2020 |
| WO | WO 2020/047010 | 3/2020 |
| WO | WO 2020/056381 | 3/2020 |
| WO | WO 2020/076979 | 4/2020 |
| WO | WO 2020/099640 | 5/2020 |
| WO | WO 2020/112604 | 6/2020 |
| WO | WO 2020/117914 | 6/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/240025 | 12/2020 |
| WO | WO 2020/243579 | 12/2020 |
| WO | WO 2020/254519 | 12/2020 |
| WO | WO 2021/041974 | 3/2021 |
| WO | WO 2021/067246 | 4/2021 |
| WO | WO 2021/067514 | 4/2021 |
| WO | WO 2021/091611 | 5/2021 |
| WO | WO 2021/092433 | 5/2021 |
| WO | WO 2021/097255 | 5/2021 |
| WO | WO 2021/102003 | 5/2021 |
| WO | WO 2021/102005 | 5/2021 |
| WO | WO 2021/102039 | 5/2021 |
| WO | WO 2021/116715 | 6/2021 |
| WO | WO 2021/119320 | 6/2021 |
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/247593 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/032195 | 2/2022 |
| WO | WO 2022/060798 | 3/2022 |
| WO | WO 2022/060953 | 3/2022 |
| WO | WO 2022/061150 | 3/2022 |
| WO | WO 2022/061152 | 3/2022 |
| WO | WO 2022/087273 | 4/2022 |
| WO | WO 2022/099037 | 5/2022 |
| WO | WO 2022/103712 | 5/2022 |
| WO | WO 2022/109181 | 5/2022 |
| WO | WO 2022/132645 | 6/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/212269 | 10/2022 |
| WO | WO 2022/221425 | 10/2022 |
| WO | WO 2022/226057 | 10/2022 |
| WO | WO 2022/236054 | 11/2022 |
| WO | WO 2022/243303 | 11/2022 |
| WO | WO 2022/226372 | 12/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/034739 | 3/2023 |
| WO | WO 2023/044071 | 3/2023 |
| WO | WO 2023/076345 | 5/2023 |
| WO | WO 2023/086880 | 5/2023 |
| WO | WO 2023/102118 | 6/2023 |
| WO | WO 2023/122033 | 6/2023 |
| WO | WO 2023/130019 | 7/2023 |
| WO | WO 2023/147355 | 8/2023 |
| WO | WO 2023/150098 | 8/2023 |
| WO | WO 2023/150163 | 8/2023 |
| WO | WO 2023/150171 | 8/2023 |
| WO | WO 2023/150763 | 8/2023 |
| WO | WO 2023/215552 | 11/2023 |
| WO | WO 2023/225519 | 11/2023 |
| WO | WO 2023/229988 | 11/2023 |
| WO | WO 2023/250077 | 12/2023 |
| WO | WO 2024/015578 | 1/2024 |
| WO | WO 2024/035844 | 2/2024 |
| WO | WO 2024/081212 | 4/2024 |
| WO | WO 2024/086167 | 4/2024 |
| WO | WO 2024/086776 | 4/2024 |
| WO | WO 2024/102809 | 5/2024 |
| WO | WO 2024/137826 | 6/2024 |
| WO | WO 2024/145224 | 7/2024 |
| WO | WO 2024/145441 | 7/2024 |
| WO | WO 2024/145445 | 7/2024 |
| WO | WO 2024/145491 | 7/2024 |
| WO | WO 2024/206603 | 10/2024 |
| WO | WO 2024/220882 | 10/2024 |

(56)      References Cited

FOREIGN PATENT DOCUMENTS

| WO | WO 2024/238900 | 11/2024 |
| WO | WO 2024/254316 | 12/2024 |
| WO | WO 2025/029605 | 2/2025 |
| WO | WO 2025/029627 | 2/2025 |
| WO | WO 2025/043076 | 2/2025 |
| WO | WO 2025/072119 | 4/2025 |
| WO | WO 2025/090912 | 5/2025 |
| WO | WO 2025/096581 | 5/2025 |
| WO | WO 2025/101864 | 5/2025 |

OTHER PUBLICATIONS

[No Author Listed], "Chromium Next GEM Single Cell 3' Reagent Kits v3.1—User Guide," 10x Genomics, Document No. CG000204, Nov. 2019, 58 pages.

[No Author Listed], "Chromium Next GEM Single Cell 3' Reagent Kits v3.1 (Dual Index)—User Guide," 10x Genomics, Mar. 2021, Document No. CG000315, 61 pages.

[No Author Listed], "HuSNP Mapping Assay User's Manual," Affymetrix Part No. 90094 (Affymetrix, Santa Clara, Calif.), GeneChip, 2000, 104 pages.

[No Author Listed], "Microarray technologies have excellent possibilities in genomics-related researches," Science Tools From Amersham Pharmacia Biotech, 1998, 3(4): 8 pages (with English Translation).

[No Author Listed], "Proseek® Multiplex 96×96 User Manual," Olink Proteomics, Olink Bioscience, Uppsala, Sweden, 2017, 20 pages.

10xGenomics.com, [online], "Visium Spatial Gene Expression Reagent Kits—Tissue Optimization—User Guide," Feb. 2022, retrieved on Mar. 29, 2024, retrieved from URL<https://cdn.10xgenomics.com/image/upload/v1660261286/support-documents/CG000238_Visium SpatialTissueOptimizationUserGuide_RevE.pdf>, 46 pages.

10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/32YzaiURFKI5Rn1fE9nIrp/188b0b5a436edfa9856072a929332a00/CG000238 VisiumSpatialTissueOptimizationUserGuide_RevC.pdf>, 42 pages.

10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw5lee9/6a2ac61cf6388a72564eeb96bc294967/CG000238 VisiumSpatialTissueOptimizationUserGuide_Rev_A.pdf>, 46 pages.

10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0CH17rEk0UXwd19It/e54d99fb08a8f1500aba503005a04a56/CG000238_VisiumSpatialTissueOptimizationUserGuide_RevD.pdf>, 43 pages.

10xGenomics.com, [online], "Visium Spatial Gene Expression Reagent Kits—User Guide," Jan. 2022, retrieved on Jun. 27, 2024, retrieved from URL<https://web.archive.org/web/20230326192142/https://www.10xgenomics.com/support/spatial-gene-expression-fresh-frozen/documentation/steps/library-construction/visium-spatial-gene-expression-reagent-kits-user-guide>, 71 pages.

10xGenomics.com, [online], "Visium Spatial Gene Expression Reagent Kits—User Guide," Jun. 2020, retrieved on May 25, 2021, retrieved from URL<https://assets.ctfassets.net/an68im79xiti/7AqbPw6d9eHXAba4eVJMSY/0c4fbd3957f50efd9c92d7cbf7d46ba5/CG000239_VisiumSpatialGeneExpression_UserGuide_RevC.pdf>, 69 pages.

10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 70 pages.

10xGenomics.com, [online], "Visium Spatial Gene Expression Reagent Kits—User Guide," Sep. 2023, retrieved on Mar. 29, 2024, retrieved from URL<https://cdn.10xgenomics.com/image/upload/v1695417753/support-documents/CG000239_VisiumSpatialGeneExpression_UserGuide_RevG.pdf>, 70 pages.

Adessi et al., "Solid phase DNA amplification: characterisation of primer attachment and amplification mechanisms," Nucl. Acids Res., 2000, 28(20):E87, 8 pages.

Adiconis et al., "Comparative analysis of RNA sequencing methods for degraded or low-input samples," Nat Methods, Jul. 2013, 10(7):623-9.

Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.

Affymetrix, "Human Genome U95Av2," Internet Citation, retrieved from the internet: on the World Wide Web affymetrix.com, retrieved on Oct. 2, 2002, 1 page.

Alam, "Proximity Ligation Assay (PLA)," Curr Protoc Immunol., Nov. 2018, 123(1):e58, 8 pages.

Albretsen et al., "Applications of magnetic beads with covalently attached oligonucleotides in hybridization: Isolation and detection of specific measles virus mRNA from a crude cell lysate," Anal. Biochem., 1990, 189(1):40-50.

Allawi et al., "Thermodynamics and NMR of Internal G.T Mismatches in DNA," Biochemistry, 1996, 36(34):10581-10594.

Amidzadeh et al., "Assessment of different permeabilization methods of minimizing damage to the adherent cells for detection of intracellular RNA by flow cytometry," Avicenna J Med Biotechnol., Jan. 2014, 6(1):38-46.

Andresen et al., "Helicase-dependent amplification: use in OnChip amplification and potential for point-of-care diagnostics," Expert Rev Mol Diagn., Oct. 2009, 9(7):645-650.

Appella, "Non-natural nucleic acids for synthetic biology," Current Opinion in Chemical Biology, Dec. 2009, 13(5-6): 687-696.

Aran et al., "xCell: digitally portraying the tissue cellular heterogeneity landscape," Genome Biol., Nov. 2017, 18(1):220, 14 pages.

Archer et al., "Selective and flexible depletion of problematic sequences from RNA-seq libraries at the cDNA stage," BMC Genomics, May 2014, 15(1):401, 9 pages.

Armani et al., "2D-PCR: a method of mapping DNA in tissue sections," Lab Chip, 2009, 9(24):3526-34.

Arslan et al., "Engineering of a superhelicase through conformational control (Supplementary Materials)," Science, Apr. 17, 2015, 348(6232):344-347, 18 pages.

Arslan et al., "Engineering of a superhelicase through conformational control," Science, Apr. 17, 2015, 348(6232):344-347.

Asp et al., "A spatiotemporal organ-wide gene expression and cell atlas of the developing human heart," Cell, Dec. 12, 2019, 179(7):1647-1660.

Asp et al., "Spatially Resolved Transcriptomes-Next Generation Tools for Tissue Exploration," Bioessays, Oct. 2020, 42(10):e1900221, 16 pages.

Atkinson et al., "An Updated Protocol for High Throughput Plant Tissue Sectioning," Front Plant Sci, 2017, 8:1721, 8 pages.

Atkinson, "Overview of Translation: Lecture Manuscript," U of Texas, 2000, DD, pp. 6.1-6.8.

Bains et al., "A novel method for nucleic acid sequence determination," Journal of Theoretical Biology, 1988, 135(3), 303-7.

Balakrishnan et al., "Flap endonuclease 1," Annu Rev Biochem., Jun. 2013, 82:119-138.

Baner et al., "Signal amplification of padlock probes by rolling circle replication," Nucleic Acids Res., 1998, 26(22):5073-5078.

Barnes, "PCR amplification of up to 35-kb DNA with high fidelity and high yield from lambda bacteriophage templates," Proc. Natl. Acad. Sci USA, 1994, 91(6):2216-2220.

Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.

Bartosovic et al., "Single-cell CUT&Tag profiles histone modifications and transcription factors in complex tissues," Nat Biotechnol., Jul. 2021, 39(7):825-835, Abstract.

(56) References Cited

OTHER PUBLICATIONS

Baugh et al., "Quantitative analysis of mRNA amplification by in vitro transcription," Nucleic Acids Res., 2001, 29(5):e29, 9 pages.

Beattie et al., "Advances in genosensor research," Clin Chem., May 1995, 41(5):700-6.

Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.

Belaghzal et al., "Hi-C 2.0: An Optimized Hi-C Procedure for High-Resolution Genome-Wide Mapping of Chromosome Conformation, " Methods, Jul. 1, 2017, 123:56-65, 20 pages.

Bell, "A simple way to treat PCR products prior to sequencing using ExoSAP-IT," Biotechniques, 2008, 44(6):834, 1 page.

Belton et al., "Hi-C: A comprehensive technique to capture the conformation of genomes," Methods, Nov. 2012, 58(3):268-276, 16 pages.

Bentley et al., "Accurate whole human genome sequencing using reversible terminator chemistry," Nature, 2008, 456(7218):53-59.

Bentzen et al., "Large-scale detection of antigen-specific T cells using peptide-MHC-I multimers labeled with DNA barcodes," Nat Biotechnol., Oct. 2016, 34(10):1037-1045, 12 pages.

Bergenstråhle et al., "Seamless integration of image and molecular analysis for spatial transcriptomics workflows," BMC Genomics, Jul. 2020, 21(1):482, 7 pages.

Berger et al., "Universal bases for hybridization, replication and chain termination," Nucleic Acid Res., Aug. 2000, 28(15):2911-2914.

Bibikova et al., "Quantitative gene expression profiling in formalin-fixed paraffin-embedded tissues using universal bead arrays," The American Journal of Pathology, Nov. 1, 2004, 165(5):1799- 1807.

Birney et al., "Identification and analysis of functional elements in 1% of the human genome by the ENCODE pilot project, " Nature, 2007, 447(7146):799-816.

Blair et al., "Microarray temperature optimization using hybridization kinetics," Methods Mol Biol., 2009, 529:171-96.

Blanchard et al., "High-density oligonucleotide arrays," Biosensors & Bioelectronics, 1996, 11(6-7):687-690.

Blanco et al., "A practical approach to FRET-based PNA fluorescence in situ hybridization," Methods, Dec. 2010, 52(4):343-51.

Blokzijl et al., "Profiling protein expression and interactions: proximity ligation as a tool for personalized medicine," J Intern. Med., 2010, 268(3):232-245.

Blow, "Tissue Issues," Nature, 2007, 448(7156):959-962.

Bolotin et al., "MiXCR: software for comprehensive adaptive immunity profiling," Nat Methods., May 2015, 12(5):380-1.

Borm et al., "High throughput human embryo spatial transcriptome mapping by surface transfer of tissue RNA," Abstracts Selected Talks, Single Cell Genomics mtg, (SCG2019), 2019, 1 pages (Abstract Only).

Boulé et al., "Terminal deoxynucleotidyl transferase indiscriminately incorporates ribonucleotides and deoxyribonucleotides," J Biol Chem., Aug. 2001, 276(33):31388-93.

Brandon et al., "Mitochondrial mutations in cancer," Oncogene, 2006, 25(34):4647-4662.

Brenner et al., "Gene expression analysis by massively parallel signature sequencing (MPSS) on microbead arrays," Nat. Biotech., 2000, 18(6):630-634.

Brenner et al., "In vitro cloning of complex mixtures of DNA on microbeads: physical separation of differentially expressed cDNAs," Proc. Natl. Acad. Sci. USA, 2000, 97(4):1665-1670.

Brow, "35—The Cleavase I enzyme for mutation and polymorphism scanning," PCR Applications Protocols for Functional Genomics, 1999, pp. 537-550.

Brown et al., "Retroviral integration: structure of the initial covalent product and its precursor, and a role for the viral IN protein," Proc Natl Acad Sci USA, Apr. 1989, 86(8):2525-9.

Buenrostro et al., "Transposition of native chromatin for multimodal regulatory analysis and personal epigenomics," Nat Methods, Dec. 2013, 10(12):1213-1218.

Bullard et al., "Direct comparison of nick-joining activity of the nucleic acid ligases from bacteriophage T4," Biochem. J. 2006, 398(1):135-144.

Bunt et al., "FRET from single to multiplexed signaling events," Biophys Rev. Apr. 2017, 9(2): 119-129.

Burgess, "A space for transcriptomics," Nature Reviews Genetics, 2016, 17(8):436-7.

Burgess, "Finding structure in gene expression," Nature Reviews Genetics, 2018, 19(5):249, 1 page.

Burgess, "Spatial transcriptomics coming of age," Nat Rev Genet., Jun. 2019, 20(6):317, 1 page.

Caliari et al., "A practical guide to hydrogels for cell culture," Nat Methods., Apr. 2016, 13(5):405-14.

Cha et al., "Specificity, efficiency, and fidelity of PCR," Genome Res., 1993, 3(3):S18-29.

Chandra et al., "Cell-free synthesis-based protein microarrays and their applications," Proteomics, 2009, 5(6):717-30.

Chatterjee et al., "Mitochondrial DNA mutations in human cancer. Oncogene," 2006, 25(34):4663-4674.

Chen et al. "Arrayed profiling of multiple glycans on whole living cell surfaces." Analytical chemistry, Oct. 15, 2013, 85(22):11153-11158.

Chen et al., "DNA hybridization detection in a microfluidic Channel using two fluorescently labelled nucleic acid probes," Biosensors and Bioelectronics, 2008, 23(12):1878-1882.

Chen et al., "Efficient in situ barcode sequencing using padlock probe-based BaristaSeq," Nucleic Acids Res., 2018, 46(4): e22, 11 pages.

Chen et al., "Expansion microscopy," Science, 2015, 347(6221):543-548.

Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.

Chen et al., "Nanoscale imaging of RNA with expansion microscopy," Nat Methods, Aug. 2016, 13(8):679-84.

Chen et al., "Parallel single nucleotide polymorphism genotyping by surface invasive cleavage with universal detection," Anal Chem., Apr. 2005, 77(8):2400-5.

Chen et al., "RNA imaging. Spatially resolved, highly multiplexed RNA profiling in single cells," Science, Apr. 2015, 348(6233):aaa6090, 21 pages.

Chen et al., "Spatial Transcriptomics and In Situ Sequencing to Study Alzheimer's Disease," Cell, Aug. 2020, 182(4):976-991.

Chen et al., "µCB-seq: microfluidic cell barcoding and sequencing for high-resolution imaging and sequencing of single cells," Lab Chip, Nov. 2020, 20(21):3899-3913.

Chester et al., "Dimethyl sulfoxide-mediated primer Tm reduction: a method for analyzing the role of renaturation temperature in the polymerase chain reaction," Anal Biochem, Mar. 1993, 209(2):284-90.

Cho et al., "Seq-Scope: Submicrometer-resolution spatial transcriptomics for single cell and subcellular studies," bioRxiv, Jan. 27, 2021, retrieved from URL <https://www.biorxiv.org/node/1754517.abstract>, 50 pages.

Choi et al., "Multiplexed detection of mRNA using porosity-tuned hydrogel microparticles," Analytical chemistry, Sep. 28, 2012, 84(21):9370-9378.

Chrisey et al., "Covalent attachment of synthetic DNA to self-assembled monolayer films," Nucleic Acids Res., Aug. 1996, 24(15):3031-9.

Ciaccio et al., "Systems analysis of EGF receptor signaling dynamics with microwestern arrays," Nat Methods, Feb. 2010, 7(2):148-55.

Codeluppi et al., "Spatial organization of the somatosensory cortex revealed by osmFISH," Nature Methods, Nov. 2018, 15:932-935.

Constantine et al., "Use of genechip high-density oligonucleotide arrays for gene expression monitoring," Life Science News, Amersham Life Science, 1998, pp. 11-14.

Corces et al., "An improved ATAC-seq protocol reduces background and enables interrogation of frozen tissues," Nat. Methods, 2017, 14(10):959-962.

(56)        References Cited

OTHER PUBLICATIONS

Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Cruz et al., "Methylation in cell-free DNA for early cancer detection," Ann Oncol., Jun. 2018, 29(6):1351-1353.
Cujec et al., "Selection of v-Abl tyrosine kinase substrate sequences from randomized peptide and cellular proteomic libraries using mRNA display," Chemistry and Biology, 2002, 9(2):253-264.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Dalma-Weiszhausz et al., "The affymetrix GeneChip platform: an overview," Methods Enzymol., 2006, 410:3-28.
Darmanis et al., "ProteinSeq: High-Performance Proteomic Analyses by Proximity, Ligation and Next Generation Sequencing," PLos One, 2011, 6(9):e25583, 10 pages.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Deamer et al., "Characterization of nucleic acids by Nanopore analysis," Acc Chem Res., Oct. 2002, 35(10):817-25.
Dean et al., "Comprehensive human genome amplification using multiple displacement amplification," Proc Natl. Acad. Sci. USA, 2002, 99(8):5261-66.
Dean et al., "Rapid Amplification Of Plasmid And Phage DNA Using Phi29 DNA Polymerase And Multiply-Primed Rolling Circle Amplification," Genome Research, Jun. 2001, 11:1095-1099.
Deng et al., "Spatial Epigenome Sequencing at Tissue Scale and Cellular Level," BioRxiv, Mar. 2021, 40 pages.
Dressman et al., "Transforming single DNA molecules into fluorescent magnetic particles for detection and enumeration of genetic variations," Proc. Natl. Acad. Sci. USA, 2003, 100(15):8817-8822.
Drmanac et al., "CoolMPS™: Advanced massively parallel sequencing using antibodies specific to each natural nucleobase," BioRxiv, 2020, 19 pages.
Druley et al., "Quantification of rare allelic variants from pooled genomic DNA," Nat. Methods, 2009, 6(4):263-65.
Duncan et al., "Affinity chromatography of a sequence-specific DNA binding protein using Teflon-linked oligonucleotides," Anal. Biochem., 1988, 169(1):104-108.
Eberwine, "Amplification of mRNA populations using aRNA generated from immobilized oligo(dT)-T7 primed cDNA," BioTechniques, 1996, 20(4):584-91.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Profiling the transcriptome with RNA SPOTs," Nat Methods., 2017, 14(12):1153-1155.
Eng et al., "Transcriptome-scale super-resolved imaging in tissues by RNA seqFISH+," Nature, Apr. 2019, 568(7751):235-239, 37 pages.
Ergin et al., "Proteomic Analysis of PAXgene-Fixed Tissues," J Proteome Res., 2010, 9(10):5188-96.
Ertsey et al., "Coverslip Mounted-Immersion Cycled in Situ RT-PCR for the Localization of mRNA in Tissue Sections," Biotechniques, 1998, 24(1):92-100.
Evers et al., "The effect of formaldehyde fixation on RNA: optimization of formaldehyde adduct removal," J Mol Diagn., May 2011, 13(3):282-8.

Fan et al., "A versatile assay for high-throughput gene expression profiling on universal array matrices," Genome Research, May 1, 2004, 14(5):878-885.
Fan et al., "Illumina Universal Bead Arrays," Methods in Enzymology, 2006, 410:57-73.
Faruqi et al., "High-throughput genotyping of single nucleotide polymorphisms with rolling circle amplification," BMC Genomics, Aug. 2001, 2:4, 10 pages.
Fire et al., "Rolling replication of short DNA circles," Proc. Natl. Acad. Sci., 1995, 92(10):4641-4645.
Flanigon et al., "Multiplex protein detection with DNA readout via mass spectrometry," N. Biotechnol., 2013, 30(2):153-158.
Fluidigm, "Equivalence of Imaging Mass Cytometry and Immunofluorescence on FFPE Tissue Sections," White Paper, 2017, 12 pages.
Fodor et al., "Light-directed, spatially addressable parallel chemical synthesis," Science, 1995, 251(4995):767-773.
Forster et al., "A human gut bacterial genome and culture collection for improved metagenomic analyses," Nature Biotechnology, 2019, 37(2):186-192.
Frese et al., "Formylglycine aldehyde Tag—protein engineering through a novel post-translational modification," ChemBioChem., 2009, 10(3):425-27.
Fu et al., "Continuous Polony Gels for Tissue Mapping with High Resolution and RNA Capture Efficiency," bioRxiv, 2021, 20 pages.
Fu et al., "Counting individual DNA molecules by the stochastic attachment of diverse labels," PNAS, 2011, 108(22):9026-9031.
Fu et al., "Repeat subtraction-mediated sequence capture from a complex genome," Plant J., Jun. 2010, 62(5):898-909.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gansauge et al., "Single-stranded DNA library preparation from highly degraded DNA using T4 DNA ligase," Nucleic Acids Res., Jun. 2017, 45(10):e79, 10 pages.
Gao et al., "A highly homogeneous expansion microscopy polymer composed of tetrahedron-like monomers," bioRxiv, Oct. 22, 2019, 23 pages (Preprint).
Gao et al., "Q&A: Expansion microscopy," BMC Biology, 15:50, 9 pages, 2017.
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Gerard et al., "Excess dNTPs minimize RNA hydrolysis during reverse transcription," Biotechniques, Nov. 2002, 33(5):984, 986, 988, 990.
Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.
Gill et al., "Nucleic acid isothermal amplification technologies: a review," Nucleosides Nucleotides Nucleic Acids, Mar. 2008, 27(3):224-43.
Glass et al., "SIMPLE: a sequential immunoperoxidase labeling and erasing method," J. Histochem. Cytochem., Oct. 2009, 57(10):899-905.
Gloor, "Gene targeting in *Drosophila*," Methods Mol Biol., 2004, 260:97-114.
Gnanapragasam, "Unlocking the molecular archive: the emerging use of formalin-fixed paraffin-embedded tissue for biomarker research in urological cancer," BJU International, 2009, 105(2):274-278.
Goh et al., "Highly Specific Multiplexed RNA Imaging In Tissues With Split-FISH," Nat Methods, Jun. 15, 2020, 17(7):689-693, 21 pages.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goldmeyer et al., "Development of a novel one-tube isothermal reverse transcription thermophilic helicase-dependent amplification

(56) References Cited

OTHER PUBLICATIONS platform for rapid RNA detection," Journal of Molecular Diagnostics, American Society for Investigative Pathology and the Association for Molecular Pathology, Nov. 1, 2007, 9(5):639-644.

Goransson et al., "A single molecule array for digital targeted molecular analyses," Nucleic Acids Res., Nov. 25, 2009, 37(1):e7, 9 pages.

Goryshin et al., "Tn5 in vitro transposition," J Biol Chem., Mar. 1998, 273(13):7367-74.

Gracia Villacampa et al., "Genome-wide Spatial Expression Profiling in FFPE Tissues," bioRxiv, Cell Genomics, posted Jul. 25, 2020, published Dec. 8, 2021, 1(3):100065, 38 pages.

Grokhovsky, "Specificity of DNA cleavage by ultrasound," Molecular Biology, 2006, 40(2):276-283.

Grünweller et al., "Locked Nucleic Acid Oligonucleotides," BioDrugs, Jul. 2007, 21(4): 235-243.

Gu et al., "Multiplex single-molecule interaction profiling of DNA-barcoded proteins," Nature, Sep. 21, 2014, 515:554-557.

Gu et al., "Protein tag-mediated conjugation of oligonucleotides to recombinant affinity binders for proximity ligation," N Biotechnol., 2013, 30(2):144-152.

Gunderson et al., "Decoding randomly ordered DNA arrays," Genome Research, 2004, 14(5):870-877.

Guo et al., "Direct fluorescence analysis of genetic polymorphisms by hybridization with oligonucleotide arrays on glass supports," Nucleic Acids Res., Dec. 1994, 22(24):5456-65.

Gupta et al., "Single-cell isoform RNA sequencing characterizes isoforms in thousands of cerebellar cells," Nature Biotechnol., Oct. 2018, 36:1197-1202.

Hadrup et al., "Parallel detection of antigen-specific T-cell responses by multidimensional encoding of MHC multimers," Nat. Methods., Jul. 2009, 6(7), 520-526.

Hafner et al., "Identification of microRNAs and other small regulatory RNAs using cDNA library sequencing," Methods, Jan. 2008, 44(1):3-12.

Hahnke et al., "Striptease on glass: validation of an improved stripping procedure for in situ microarrays," J Biotechnol., Jan. 2007, 128(1):1-13.

Hamaguchi et al., "Direct reverse transcription-PCR on oligo(dT)-immobilized polypropylene microplates after capturing total mRNA from crude cell lysates," Clin Chem., Nov. 1998, 44(11):2256-63.

Hanauer et al., "Separation of nanoparticles by gel electrophoresis according to size and shape," Nano Lett., Sep. 2007, 7(9):2881-5.

Hardenbol et al., "Highly multiplexed molecular inversion probe genotyping: over 10,000 targeted SNPs genotyped in a single tube assay," Genome Res., Feb. 2005, 15(2):269-75.

Hardenbol et al., "Multiplexed genotyping with sequence-tagged molecular inversion probes," Nature Biotechnol., Jun. 2003, 21(6):673-678.

Hayes et al., "Electrophoresis of proteins and nucleic acids: I-Theory," BMJ, Sep. 1989, 299(6703):843-6.

He et al., "In situ synthesis of protein arrays," Current Opinion in Biotechnology, 2008, 19(1):4-9.

He et al., "Printing protein arrays from DNA arrays," Nature Methods, 2008, 5(2):175-77.

He, "Cell-free protein synthesis: applications in proteomics and biotechnology," New Biotechnology, 2008, 25(2-3):126-132.

Healy, "Nanopore-based single-molecule DNA analysis," Nanomedicine (Lond), Aug. 2007, 2(4):459-81.

Hejatko et al., "In situ hybridization technique for mRNA detection in whole mount *Arabidopsis* samples," Nature Protocols, 2006, 1(4):1939-1946.

Hessner et al., "Genotyping of factor V G1691A (Leiden) without the use of PCR by invasive cleavage of oligonucleotide probes," Clin Chem., Aug. 2000, 46(8 Pt 1):1051-6.

Hiatt et al., "Parallel, tag-directed assembly of locally derived short sequence reads," Nature Methods, 2010, 7(2):119-25.

Ho et al., "Bacteriophage T4 RNA ligase 2 (gp24.1) exemplifies a family of RNA ligases found in all phylogenetic domains," PNAS, Oct. 2002, 99(20):12709-14.

Ho et al., "Characterization of an ATP-Dependent DNA Ligase Encoded by Chlorella Virus PBCV-1," Journal of Virology, Mar. 1997, 71(3):1931-1937.

Hobro et al, "An evaluation of fixation methods: Spatial and compositional cellular changes observed by Raman imaging," Vibrational Spectroscopy, Jul. 2017, 91:31-45.

Hoffman et al., "Formaldehyde crosslinking: a tool for the study of chromatin complexes," J Biol Chem., Oct. 2015, 290(44):26404-11.

Howell et al., "iFRET: An Improved Fluorescence System for DNA-Melting Analysis," Genome Research, 2002, 12:1401-1407.

Hsuih et al., "Novel, Ligation-Dependent PCR Assay for Detection of Hepatitis C Virus in Serum," Journal of Clinical Microbiology, Mar. 1996, 34(3):501-507.

Hu et al., "High reproducibility using sodium hydroxide-stripped long oligonucleotide DNA microarrays," Biotechniques, Jan. 2005, 38(1):121-4.

Hughes et al., "Microfluidic Western blotting," PNAS, Dec. 2012, 109(52):21450-21455.

Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.

Ichikawa et al., "In vitro transposition of transposon Tn3," J Biol. Chem., Nov. 1990, 265(31):18829-32, Abstract.

Illumina.com [online], "Ribo-Zero® rRNA Removal Kit Reference Guide," Aug. 2016, retrieved on Apr. 26, 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.

Jamur et al., "Permeabilization of cell membranes.," Method Mol. Biol., 2010, 588:63-66.

Jemt et al., "An automated approach to prepare tissue-derived spatially barcoded RNA-sequencing libraries," Scientific Reports, 2016, 6:37137, 10 pages.

Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.

Jucá et al., "Effect of dimethyl sulfoxide on reverse transcriptase activity," Braz. J. Med. Biol. Res., Mar. 1995, 28(3):285-90.

Kalantari et al., "Deparaffinization of formalin-fixed paraffin-embedded tissue blocks using hot water instead of xylene," Anal Biochem., Aug. 2016, 507:71-3.

Kap et al., "Histological assessment of PAXgene tissue fixation and stabilization reagents," PLoS One, 2011, 6:e27704, 10 pages.

Kapteyn et al., "Incorporation of non-natural nucleotides into template-switching oligonucleotides reduces background and improves cDNA synthesis from very small RNA samples," BMC Genomics, Jul. 2010, 11:413, 9 pages.

Karmakar et al., "Organocatalytic removal of formaldehyde adducts from RNA and DNA bases," Nature Chemistry, Aug. 3, 2015, 7(9):752-758.

Kaya-Okur et al., "CUT&Tag for efficient epigenomic profiling of small samples and single cells," Apr. 2019, 10(1):1930, 10 pages.

Ke et al., "In situ sequencing for RNA analysis in preserved tissue and cells," Nat Methods., Sep. 2013, Supplementary Materials, 29 pages.

Kennedy-Darling et al., "Measuring the Formaldehyde Protein-DNA Cross-Link Reversal Rate," Analytical Chemistry, 2014, 86(12):5678-5681.

Kent et al., "Polymerase θ is a robust terminal transferase that oscillates between three different mechanisms during end-joining" Elife, Jun. 2016, 5:e13740, 25 pages.

Kirby et al., "Cryptic plasmids of *Mycobacterium avium*: Tn552 to the rescue," Mol Microbiol., Jan. 2002, 43(1):173-86.

Kleckner et al., "Tn10 and IS10 transposition and chromosome rearrangements: mechanism and regulation in vivo and in vitro," Curr Top Microbiol Immunol., 1996, 204:49-82.

Korbel et al., "Paired-end mapping reveals extensive structural variation in the human genome," Science, 2007, 318(5849):420-426.

(56) References Cited

OTHER PUBLICATIONS

Kozlov et al., "A highly scalable peptide-based assay system for proteomics," PLoS ONE, 2012, 7(6):e37441, 10 pages.

Kozlov et al., "A method for rapid protease substrate evaluation and optimization," Comb Chem High Throughput Screen, 2006, 9(6):481-87.

Kristensen et al., "High-Throughput Methods for Detection of Genetic Variation," BioTechniques, Feb. 2001, 30(2):318-332.

Krzywkowski et al., "Chimeric padlock and iLock probes for increased efficiency of targeted RNA detection," RNA, Jan. 2019, 25(1):82-89.

Krzywkowski et al., "Fidelity of RNA templated end-joining by Chlorella virus DNA ligase and a novel iLock assay with improved direct RNA detection accuracy," Nucleic Acids Research, Oct. 2017, 45(18):e161, 9 pages.

Kuhn et al., "A novel, high-performance random array platform for quantitative gene expression profiling," Genome Res, 2004, 14:2347-2356.

Kumar et al., "Template-directed oligonucleotide strand ligation, covalent intramolecular DNA circularization and catenation using click chemistry," J Am Chem Soc., May 2007, 129(21):6859-64.

Kurz et al., "cDNA—protein fusions: covalent protein—gene conjugates for the in vitro selection of peptides and proteins," ChemBioChem., 2001, 2(9):666-72.

Kwok, "High-throughput genotyping assay approaches," Pharmacogenomics, Feb. 2000, 1(1):95-100.

Lage et al., "Whole genome analysis of genetic alterations in small DNA samples using hyperbranched strand displacement amplification and array-CGH," Genome Research, 2003, 13(2):294-307.

Lahiani et al., "Enabling Histopathological Annotations on Immunofluorescent Images through Virtualization of Hematoxylin and Eosin," J Pathol Inform., Feb. 2018, 9:1, 8 pages.

Lampe et al., "A purified mariner transposase is sufficient to mediate transposition in vitro," EMBO J., Oct. 1996, 15(19):5470-9.

Landegren et al., "A Ligase-Mediated Gene Detection Technique," Science, 1988, 241(4869):1077-1080.

Landegren et al., "Reading bits of genetic information: methods for single-nucleotide polymorphism analysis," Genome Res., Aug. 1998, 8(8):769-76.

Langdale et al., "A rapid method of gene detection using DNA bound to Sephacryl," Gene, 1985, 36(3):201-210.

Larman et al., "Sensitive, multiplex and direct quantification of RNA sequences using a modified RASL assay," Nucleic Acids Research, 2014, 42(14):9146-9157.

Lee et al., "Fluorescent in situ sequencing (FISSEQ) of RNA for gene expression profiling in intact cells and tissues," Nature Protocols, 2015, 10(3):442-458.

Lee et al., "Improving the efficiency of genomic loci capture using oligonucleotide arrays for high throughput resequencing," BMC Genomics, Dec. 2009, 10:646, 12 pages.

Leriche et al., "Cleavable linkers in chemical biology," Bioorganic & Medicinal Chemistry, 2012, 20:571-582.

Li et al., "A new GSH-responsive prodrug of 5-aminolevulinic acid for photodiagnosis and photodynamic therapy of tumors," European Journal of Medicinal Chemistry, Nov. 2019, 181:111583, 9 pages.

Li et al., "A photocleavable fluorescent nucleotide for DNA sequencing and analysis," Proc. Natl. Acad. Sci., 2003, 100(2):414-419.

Li et al., "An activity-dependent proximity ligation platform for spatially resolved quantification of active enzymes in single cells," Nat Commun, Nov. 2017, 8(1):1775, 12 pages.

Li et al., "RASL-seq for Massively Parallel and Quantitative Analysis of Gene Expression," Curr Protoc Mol Biol., Apr. 2012, 4(13):1-10.

Li et al., "Review: a comprehensive summary of a decade development of the recombinase polymerase amplification," Analyst, Dec. 2018, 144(1):31-67.

Lin et al., "Highly multiplexed imaging of single cells using a high-throughput cyclic immunofluorescence method," Nat Commun., Sep. 2015, 6:8390, 7 pages.

Linnarsson, "Recent advances in DNA sequencing methods—general principles of sample preparation," Experimental Cell Research, 2010, 316(8):1339-1343.

Liu et al., "High-Spatial-Resolution Multi-Omics Atlas Sequencing of Mouse Embryos via Deterministic Barcoding in Tissue," BioRxiv, 2019, 55 pages.

Liu et al., "High-Spatial-Resolution Multi-Omics Sequencing via Deterministic Barcoding in Tissue," Cell, Nov. 13, 2020, 183(6):1665-1681, 36 pages.

Liu et al., "Spatial transcriptome sequencing of FFPE tissues at cellular level," bioRxiv 788992, Oct. 14, 2020, 39 pages.

Lizardi et al., "Mutation detection and single-molecule counting using isothermal rolling-circle amplification," Nat. Genet., 1998, 19(3):225-232.

Lou et al., "A review of room temperature storage of biospecimen tissue and nucleic acids for anatomic pathology laboratories and biorepositories," Clin Biochem., Mar. 2014, 47(4-5):267-73.

Lovatt et al., "Transcriptome in vivo analysis (TIVA) of spatially defined single cells in live tissue," Nature Methods, 2013, 11(2):190-196.

Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.

Lundberg et al., "High-fidelity amplification using a thermostable DNA polymerase isolated from Pyrococcus furiosus," Gene, 1991, 108(1):1-6.

Lundberg et al., "Homogeneous antibody-based proximity extension assays provide sensitive and specific detection of low-abundant proteins in human blood," Nucleic Acids Res., 2011, 39(15):e102, 8 pages.

Lundberg et al., "Multiplexed homogeneous proximity ligation assays for high-throughput protein biomarker research in serological material," Mol Cell Proteomics, 2011, 10(4):M110.004978, 11 pages.

Lundin et al., "Increased throughput by parallelization of library preparation for massive sequencing," PLoS One, Apr. 2010, 5(4):e10029, 7 pages.

Lyamichev et al., "Invader assay for SNP genotyping," Methods Mol Biol., 2003, 212:229-40.

Lyamichev et al., "Polymorphism identification and quantitative detection of genomic DNA by invasive cleavage of oligonucleotide probes," Nat Biotechnol., Mar. 1999, 17(3):292-6.

Lyck et al., "Immunohistochemical markers for quantitative studies of neurons and glia in human neocortex," J Histochem Cytochem, 2008, 56(3):201-21.

Lykidis et al., "Novel zinc-based fixative for high quality DNA, RNA and protein analysis," Nucleic Acids Res., Jun. 2007, 35(12):e85, 10 pages.

Ma et al., "Isothermal amplification method for next-generation sequencing," PNAS, Aug. 12, 2013, 110(35):14320-14323.

MacBeath et al., "Printing proteins as microarrays for high-throughput function determination," Science, Sep. 2000, 289(5485):1760-1763.

MacIntyre, "Unmasking antigens for immunohistochemistry.," Br J Biomed Sci., 2001, 58(3):190-6.

Mamedov et al., "Preparing unbiased T-cell receptor and antibody cDNA libraries for the deep next generation sequencing profiling," Frontiers in Immunol., Dec. 23, 2013, 4(456):1-10.

Marx, "Method of the Year: spatially resolved transcriptomics," Nature Methods, 2021, 18(1): 9-14.

Mathieson et al., "A Critical Evaluation of the PAXgene Tissue Fixation System: Morphology, Immunohistochemistry, Molecular Biology, and Proteomics," Am J Clin Pathol., Jul. 8, 2016, 146(1):25-40.

McCloskey et al., "Encoding PCR products with batch-stamps and barcodes," Biochem. Genet., 2007, 45(11-12):761-767.

Meers et al., "Improved CUT&RUN chromatin profiling tools," Elife, Jun. 2019, 8:e46314, 16 pages.

Merritt et al., "Multiplex digital spatial profiling of proteins and RNA in fixed tissue," Nat Biotechnol, May 2020, 38(5):586-599.

Metzker, "Sequencing technologies—the next generation," Nature Reviews Genetics, 2010, 11(1):31-46.

(56) References Cited

OTHER PUBLICATIONS

Miele et al., "Mapping cis- and trans- chromatin interaction networks using chromosome conformation capture (3C)," Methods Mol Biol., 2009, 464:105-21.

Mignardi et al., "Oligonucleotide gap-fill ligation for mutation detection and sequencing in situ," Nucleic Acids Research, Aug. 3, 2015, 43(22):e151, 12 pages.

Miller et al., "Basic concepts of microarrays and potential applications in clinical microbiology," Clinical Microbiology Reviews, 2009, 22(4):611-633.

Miller et al., "Chapter 11—Solid and Suspension Microarrays for Microbial Diagnostics," Methods in Microbiology, 2015, 42:395-431.

Miner et al., "Molecular barcodes detect redundancy and contamination in hairpin-bisulfite PCR," Nucleic Acids Res., Sep. 2004, 32(17):e135, 4 pages.

Mishra et al., "Three-dimensional genome architecture and emerging technologies: looping in disease," Genome Medicine, 2017, 9(1):87, 14 pages.

Mitra et al., "Digital genotyping and haplotyping with polymerase colonies," Proc. Natl. Acad. Sci. USA, May 2003, 100(10):5926-5931.

Miura et al., "Highly efficient single-stranded DNA ligation technique improves low-input whole-genome bisulfite sequencing by post-bisulfite adaptor tagging," Nucleic Acids Res., Sep. 2019, 47(15):e85, 10 pages.

Mizusawa et al., "A bacteriophage lambda vector for cloning with BamHI and Sau3A," Gene, 1982, 20(3):317-322.

Mohsen et al., "The Discovery of Rolling Circle Amplification and Rolling Circle Transcription," Acc Chem Res., Nov. 15, 2016, 49(11):2540-2550, 25 pages.

Morlan et al., "Selective depletion of rRNA enables whole transcriptome profiling of archival fixed tissue," PLoS One, Aug. 2012, 7(8):e42882, 8 pages.

Motea et al., "Terminal deoxynucleotidyl transferase: the story of a misguided DNA polymerase," Biochim Biophys Acta., May 2010, 1804(5):1151-66.

Mulder et al., "CapTCR-seq: hybrid capture for T-cell receptor repertoire profiling," Blood Advances, Dec. 2018, 2(23):3506-3514.

Nadji et al., "Immunohistochemistry of tissue prepared by a molecular-friendly fixation and processing system," Appl Immunohistochem Mol Morphol., Sep. 2005, 13(3):277-82.

Nallur et al., "Signal amplification by rolling circle amplification on DNA microarrays," Nucleic Acids Res., Dec. 1, 2001, 29(23):e118, 9 pages.

Nam et al., "Nanoparticle-Based Bio-Bar Codes for the Ultrasensitive Detection of Proteins," Science, Sep. 26, 2003, 301(5641):1884-1886.

Nandakumar et al., "How an RNA Ligase Discriminates RNA versus DNA Damage," Molecular Cell, 2004, 16:211-221.

Nandakumar et al., "RNA Substrate Specificity and Structure-guided Mutational Analysis of Bacteriophage T4 RNA Ligase 2," Journal of Biological Chemistry, Jul. 2004, 279(30):31337-31347.

Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.

Ng et al., "Gene identification signature (GIS) analysis for transcriptome characterization and genome annotation," Nature Methods, 2005, 2(2):105-111.

Nichols et al., "RNA Ligases," Curr Protoc Mol Biol., Oct. 2008, 84(1):3.15.1-3.15.4.

Niedringhaus et al., "Landscape of next-generation sequencing technologies," Anal Chem., Jun. 2011, 83(12):4327-41.

Nikiforov et al., "The use of 96-well polystyrene plates for DNA hybridization-based assays: an evaluation of different approaches to oligonucleotide immobilization," Anal Biochem, May 1995, 227(1):201-9.

Niklas et al., "Selective permeabilization for the high-throughput measurement of compartmented enzyme activities in mammalian cells," Anal Biochem, Sep. 2011, 416(2):218-27.

Nilsson et al., "RNA-templated DNA ligation for transcript analysis," Nucleic Acids Res., Jan. 2001, 29(2):578-81.

Nowak, "Entering the Postgenome Era," Science, 1995, 270(5235):368-71.

Ohtsubo et al., "Bacterial insertion sequences," Curr Top Microbiol Immunol., 1996, 204:1-26.

Oksuz et al., "Systematic evaluation of chromosome conformation capture assays," Nature Methods, Sep. 2021, 18:1046-1055.

Olivier, "The Invader assay for SNP genotyping," Mutat. Res., Jun. 2005, 573(1-2):103-110.

Orenstein et al., "γPNA FRET Pair Miniprobes for Quantitative Fluorescent In Situ Hybridization to Telomeric DNA in Cells and Tissue," Molecules, Dec. 2, 2017, 22(12):2117, 15 pages.

Ozsolak et al., "Digital transcriptome profiling from attomole-level RNA samples," Genome Res., Apr. 2010, 20(4):519-25.

Pandey et al., "Inhibition of terminal deoxynucleotidyl transferase by adenine dinucleotides. Unique inhibitory action of Ap5A," FEBS Lett., Mar. 1987, 213(1):204-8.

Park et al., "Single cell trapping in larger microwells capable of supporting cell spreading and proliferation," Microfluid Nanofluid, 2010, 8:263-268.

Passow et al., "RNAlater and flash freezing storage methods nonrandomly influence observed gene expression in RNAseq experiments," bioRxiv, Jul. 2018, 28 pages.

PCT International Search Report and Written Opinion in International Appln. No. PCT/US2023/079071, dated Feb. 28, 2024, 15 pages.

Pellestor et al., "The peptide nucleic acids (PNAs), powerful tools for molecular genetics and cytogenetics," Eur J Hum Genet., Sep. 2004, 12(9):694-700.

Pemov et al., "DNA analysis with multiplex microarray-enhanced PCR," Nucl. Acids Res., Jan. 2005, 33(2):e11, 9 pages.

Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.

Perler et al., "Intervening sequences in an Archaea DNA polymerase gene," Proc Natl Acad Sci USA, Jun. 1992, 89(12):5577-5581.

Perocchi et al., "Antisense artifacts in transcriptome microarray experiments are resolved by actinomycin D," Nucleic Acids Res., 2007, 35(19):e128, 7 pages.

Petterson et al., "Generations of sequencing technologies," Genomics, 2009, 93(2):105-111.

Picelli et al., "Full-length RNA-seq from single cells using Smart-seq2," Nat Protoc., Jan. 2014, 9(1):171-81.

Picelli et al., "Tn5 transposase and tagmentation procedures for massively scaled sequencing projects," Genome Res., Dec. 2014, 24(12):2033-40.

Piepenburg et al., "DNA detection using recombination proteins," PLoS Biol., Jul. 2006, 4(7):e204, 7 pages.

Plasterk, "The Tcl/mariner transposon family," Curr Top Microbiol Immunol., 1996, 204:125-43.

Plongthongkum et al., "Advances in the profiling of DNA modifications: cytosine methylation and beyond," Nature Reviews Genetics, Aug. 2014, 15(10):647-661.

Polsky-Cynkin et al., "Use of DNA immobilized on plastic and agarose supports to detect DNA by sandwich hybridization," Clin. Chem., 1985, 31(9):1438-1443.

Porreca et al., "Polony DNA sequencing," Curr Protoc Mol Biol., Nov. 2006, Chapter 7, Unit 7.8, pp. 7.8.1-7.8.22.

U.S. Appl. No. 61/267,363, filed Dec. 7, 2009, 33 pages.

Qiu et al., "Combination probes with intercalating anchors and proximal fluorophores for DNA and RNA detection," Nucleic Acids Research, Sep. 2016, 44(17):e138, 12 pages.

Raab et al., "Human tRNA genes function as chromatin insulators," EMBO J., Jan. 2012, 31(2):330-50.

Raj et al., "Imaging individual mRNA molecules using multiple singly labeled probes," Nature Methods, Oct. 2008, 5(10):877-879, 9 pages.

(56) References Cited

OTHER PUBLICATIONS

Ranki et al., "Sandwich hybridization as a convenient method for the detection of nucleic acids in crude samples," Gene, 1983, 21(1-2):77-85.

Redmond et al., "Single-cell TCRseq: paired recovery of entire T-cell alpha and beta chain transcripts in T-cell receptors from single-cell RNAseq," Genome Med, 2016, 8:80, 12 pages.

Reinartz et al., "Massively parallel signature sequencing (MPSS) as a tool for in-depth quantitative gene expression profiling in all organisms," Brief Funct Genomic Proteomic, Feb. 2002, 1(1):95-104.

Reznikoff, "Tn5 as a model for understanding DNA transposition," Mol Microbiol., Mar. 2003, 47(5):1199-206.

Ristic et al., "Detection of Protein-Protein Interactions and Post-translational Modifications Using the Proximity Ligation Assay: Application to the Study of the SUMO Pathway," Methods Mol. Biol., 2016, 1449:279-90.

Rodriques et al., "Slide-seq: A scalable technology for measuring genome-wide expression at high spatial resolution," Science, 2019, 363(6434):1463-1467.

Rohland et al., "Partial uracil-DNA-glycosylase treatment for screening of ancient DNA," Phil. Trans. R. Soc. B, Jan. 19, 2015, 370(1660): 20130624, 11 pages.

Ronaghi et al., "A sequencing method based on real-time pyrophosphate," Science, Jul. 1998, 281(5375):363-365.

Ronaghi et al., "Real-time DNA sequencing using detection of pyrophosphate release," Analytical Biochemistry, Nov. 1996, 242(1):84-89.

Ronaghi, "Pyrosequencing sheds light on DNA sequencing," Genome Res, Jan. 2001, 11(1):3-11.

Roy et al., "Assessing long-distance RNA sequence connectivity via RNA-templated DNA-DNA ligation," eLife, 2015, 4:e03700, 21 pages.

Salmén et al., "Barcoded solid-phase RNA capture for Spatial Transcriptomics profiling in mammalian tissue sections," Nature Protocols, Oct. 2018, 13(11):2501-2534.

Saxonov et al., "10x Genomics, Mastering Biology to Advance Human Health," PowerPoint, 10x, 2020, 41 pages.

Schena et al., "Quantitative monitoring of gene expression patterns with a complementary DNA microarray," Science, Oct. 1995, 270(5235):467-470.

Schmidl et al., "ChIPmentation: fast, robust, low-input ChIP-seq for histones and transcription factors," Nature Methods, Oct. 2015, 12:963-965.

Schouten et al., "Relative quantification of 40 nucleic acid sequences by multiplex ligation-dependent probe amplification," Nucleic Acids Res., Jun. 2002, 30(12):e57, 13 pages.

Schweitzer et al., "Immunoassays with rolling circle DNA amplification: A versatile platform for ultrasensitive antigen detection," Proc. Natl Acad. Sci. USA, May 22, 2000, 97:10113-119.

Schweitzer et al., "Multiplexed protein profiling on microarrays by rolling-circle amplification," Nature Biotechnology, Apr. 2002, 20(4):359-365.

Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.

Shalon et al., "A DNA microarray system for analyzing complex DNA samples using two-color fluorescent probe hybridization," Genome Res., Jul. 1996, 6(7):639-45.

Shelbourne et al., "Fast copper-free click DNA ligation by the ring-strain promoted alkyne-azide cycloaddition reaction," Chem. Commun., 2011, 47(22):6257-6259.

Shendure et al., "Accurate multiplex polony sequencing of an evolved bacterial genome," Science, 2005, 309(5741):1728-1732.

Simonis et al., "Nuclear organization of active and inactive chromatin domains uncovered by chromosome conformation capture-on-chip (4C)," Nat Genet., Nov. 2006, 38(11):1348-54.

Singh et al., "High-throughput targeted long-read single cell sequencing reveals the clonal and transcriptional landscape of lymphocytes," Nat Commun., Jul. 2019, 10(1):3120, 13 pages.

Skene et al., "An efficient targeted nuclease strategy for high-resolution mapping of DNA binding sites," Elife, Jan. 2017, 6:e21856, 35 pages.

Slomovic et al., "Addition of poly(A) and poly(A)-rich tails during RNA degradation in the cytoplasm of human cells," Proc Natl Acad Sci USA, Apr. 2010, 107(16):7407-12.

Sountoulidis et al., "SCRINSHOT, a spatial method for single-cell resolution mapping of cell states in tissue sections," PLoS Biol., Nov. 2020, 18(11):e3000675, 32 pages.

Spiess et al., "A highly efficient method for long-chain cDNA synthesis using trehalose and betaine," Anal. Biochem., Feb. 2002, 301(2):168-74.

Spitale et al., "Structural imprints in vivo decode RNA regulatory mechanisms," Nature, 2015, 519(7544):486-90.

Stahl et al., "Visualization and analysis of gene expression in tissue sections by spatial transcriptomics," Science, Jul. 2016, 353(6294):78-82.

Stahl et al., "Visualization and analysis of gene expression in tissue sections by spatial transcriptomics," Supplementary Materials, Science, Jul. 2016, 353(6294):78-82, 41 pages.

Stimpson et al., "Real-time detection of DNA hybridization and melting on oligonucleotide arrays by using optical wave guides," Proc Natl Acad Sci USA, Jul. 1995, 92(14):6379-83.

Stoddart et al., "Single-nucleotide discrimination in immobilized DNA oligonucleotides with a biological nanopore," PNAS USA., May 2009, 106(19):7702-7707.

Strell et al., "Placing RNA in context and space—methods for spatially resolved transcriptomics," The FEBS Journal, 2019, 286(8):1468-1481.

Stroh et al., "Quantum dots spectrally distinguish multiple species within the tumor milieu in vivo," Nat Med., Jun. 2005, 11(6):678-82.

Su et al., "Restriction enzyme selection dictates detection range sensitivity in chromatin conformation capture-based variant-to-gene mapping approaches," bioRxiv, Dec. 15, 2020, 22 pages.

Sun et al., "Statistical Analysis of Spatial Expression Pattern for Spatially Resolved Transcriptomic Studies," Nature Methods, Jan. 27, 2020, 17(2): 193-200.

Sutherland et al., "Utility of formaldehyde cross-linking and mass spectrometry in the study of protein- protein interactions," J. Mass Spectrom., Jun. 2008, 43(6):699-715.

Svensson et al., "SpatialDE: identification of spatially variable genes," Nature Methods, May 2018, 15:343-346, 15 pages.

Takei et al., "Integrated Spatial Genomics Reveals Global Architecture Of Single Nuclei," Nature, Jan. 27, 2021, 590(7845):344-350, 53 pages.

Taylor et al., "Mitochondrial DNA mutations in human disease," Nature Reviews Genetics, May 2005, 6(5):389-402.

Tentori et al., "Detection of Isoforms Differing by a Single Charge Unit in Individual Cells," Chem. Int. Ed., 2016, 55(40):12431-5.

Tian et al., "Antigen peptide-based immunosensors for rapid detection of antibodies and antigens," Anal Chem, 2009, 81(13):5218-5225.

Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.

Tolbert et al., "New methods for proteomic research: preparation of proteins with N-terminal cysteines for labeling and conjugation," Angewandte Chemie International Edition, Jun. 2002, 41(12):2171-4.

Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.

Trejo et al., "Extraction-free whole transcriptome gene expression analysis of FFPE sections and histology-directed subareas of tissue," Plos One, Feb. 2019, 14(2):e0212031, 22 pages.

(56)        References Cited

OTHER PUBLICATIONS

Tu et al., "TCR sequencing paired with massively parallel 3' RNA-seq reveals clonotypic T cell signatures," Nature Immunology, Dec. 2019, 20(12):1692-1699.
Twyman et al., "Techniques Patents for SNP Genotyping," Pharmacogenomics, Jan. 2003, 4(1):67-79.
Ulery et al., "Biomedical Applications of Biodegradable Polymers," J Polym Sci B Polym Phys., Jun. 2011, 49(12):832-864.
U.S. Appl. No. 60/416,118 Fan et al., Multiplex Nucleic Acid Analysis Using Archived or Fixed Samples, filed Oct. 3, 2002, 22 pages.
Van Gelder et al., "Amplified RNA synthesized from limited quantities of heterogeneous cDNA," Proc. Natl. Acad. Sci. USA, 1990, 87(5):1663-1667.
Vandenbroucke et al., "Quantification of splice variants using real-time PCR," Nucleic Acids Research, 2001, 29(13):e68, 7 pages.
Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Vázquez Bernat et al., "High-Quality Library Preparation for NGS-Based Immunoglobulin Germline Gene Inference and Repertoire Expression Analysis," Front Immunol., Apr. 2019, 10:660, 12 pages.
Velculescu et al., "Serial analysis of gene expression," Science, Oct. 1995, 270(5235):484-7.
Vickovic et al., "High-definition spatial transcriptomics for in situ tissue profiling," Nat Methods, Oct. 2019, 16(10):987-990.
Vickovic et al., "SM-Omics: An automated Platform for High-Throughput Spatial Multi-Omics," bioRxiv, Oct. 2020, 40 pages.
Vincent et al., "Helicase-dependent isothermal DNA amplification," EMBO Rep., Aug. 2004, 5(8):795-800.
Viollet et al., "T4 RNA ligase 2 truncated active site mutants: improved tools for RNA analysis," BMC Biotechnol., Jul. 2011, 11:72, 14 pages.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.
Wang et al., "High-fidelity mRNA amplification for gene profiling," Nature Biotechnology, Apr. 2000, 18(4):457-459.
Wang et al., "Imaging-based pooled CRISPR screening reveals regulators of lncRNA localization," Proc Natl Acad Sci USA, May 2019, 116(22):10842-10851.
Wang et al., "Optimization of Process Conditions for Infected Animal Tissues by Alkaline Hydrolysis Technology," Procedia Environmental Sciences, 2016, 31:366-374.
Wang et al., "Tagmentation-based whole-genome bisulfite sequencing," Nature Protocols, Oct. 2013, 8(10):2022-2032.
Wang, "RNA amplification for successful gene profiling analysis," J Transl Med., Jul. 2005, 3:28, 11 pages.
Weinreich et al., "Evidence that the cis Preference of the Tn5 Transposase is Caused by Nonproductive Multimerization," Genes and Development, Oct. 1994, 8(19):2363-2374.
Wiedmann et al., "Ligase chain reaction (LCR)—overview and applications," PCR Methods Appl., Feb. 1994, 3(4):S51-64.
Wilson et al., "New transposon delivery plasmids for insertional mutagenesis in Bacillus anthracis," J Microbiol Methods, Dec. 2007, 71(3):332-5.

Wohnhaas et al., "DMSO cryopreservation is the method of choice to preserve cells for droplet-based single-cell RNA sequencing," Scientific Reports, Jul. 2019, 9(1):10699, 14 pages.
Wolf et al., "Rapid hybridization kinetics of DNA attached to submicron latex particles," Nucleic Acids Res, 1987, 15(7):2911-2926.
Wong et al., "Direct Site-Selective Covalent Protein Immobilization Catalyzed by a Phosphopantetheinyl Transferase," J. Am. Chem Soc., 2008, 130(37):12456-64.
Worthington et al., "Cloning of random oligonucleotides to create single-insert plasmid libraries," Anal Biochem, 2001, 294(2):169-175.
Wu et al., "Detection DNA Point Mutation with Rolling-Circle Amplification Chip," IEEE, 2010 4th International Conference on Bioinformatics and Biomedical Engineering, Jun. 2010, 4 pages.
Wu et al., "RollFISH achieves robust quantification of single-molecule RNA biomarkers in paraffin-embedded tumor tissue samples," Commun Biol., Nov. 2018, 1:209, 8 pages.
Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.
Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.
Yeakley et al., "A trichostatin A expression signature identified by TempO-Seq targeted whole transcriptome profiling," PLoS One, May 2017, 12(5):e0178302, 22 pages.
Yeakley et al., "Profiling alternative splicing on fiber-optic arrays," Nature biotechnology, 2002, 20:353-358.
Yershov et al., "DNA analysis and diagnostics on oligonucleotide microchips," Proc. Natl. Acad. Sci. USA, May 1996, 93(10):4913-4918.
Yin et al., "Genetically encoded short peptide tag for versatile protein labeling by Sfp phosphopantetheinyl transferase," PNAS, 2005, 102(44):15815-20.
Zahra et al., "Assessment of Different Permeabilization Methods of Minimizing Damage to the Adherent Cells for Detection of Intracellular RNA by Flow Cytometry," Avicenna Journal of Medical Biotechnology, Jan. 1, 2014, 6(1):38-46.
Zhang et al., "Archaeal RNA ligase from Thermoccocus kodakarensis for template dependent ligation," RNA Biol., Jan. 2017, 14(1):36-44.
Zhang et al., "Assembling DNA through Affinity Binding to Achieve Ultrasensitive Protein Detection," Angew Chem Int Ed Engl., 2013, 52(41):10698-705.
Zhang et al., "Binding-induced DNA assembly and its application to yoctomole detection of proteins," Anal Chem, 2012, 84(2):877-884.
Zhang et al., "Genome-wide open chromatin regions and their effects on the regulation of silk protein genes in Bombyx mori," Sci Rep., Oct. 2017, 7(1):12919, 9 pages.
Zhang et al., "Multiplex ligation-dependent probe amplification (MLPA) for ultrasensitive multiplexed microRNA detection using ribonucleotide-modified DNA probest," Chem. Commun., 2013, 49:10013-10015.
Zhao et al., "Isothermal Amplification of Nucleic Acids," Chemical Reviews, Nov. 2015, 115(22):12491-12545.
Zheng et al., "Origins of human mitochondrial point mutations as DNA polymerase gamma-mediated errors," Mutat. Res., 2006, 599(1-2):11-20.
Zhou et al., "Genetically encoded short peptide tags for orthogonal protein labeling by Sfp and AcpS phosphopantetheinyl transferases," ACS Chemical Biol., 2007, 2(5):337-346.
Zhu et al., "Reverse transcriptase template switching: a SMART approach for full-length cDNA library construction," Biotechniques, Apr. 2001, 30(4):892-897.
Kishi et al., "Light-Seq: light-directed in situ barcoding of biomolecules in fixed cells and tissues for spatially indexed sequencing," Nature Methods, Oct. 10, 2022, 19(11):1393-1402.
PCT International Preliminary Opinion on Patentability in International Appln. No. PCT/US2023/079071, dated May 22, 2025, 10 pages.

(56)                    References Cited

OTHER PUBLICATIONS

Stickels et al., "Highly sensitive spatial transcriptomics at near-cellular resolution with Slide-seqV2," Nat Biotechnol., Mar. 2021, 39(3):313-319, 28 pages (Author Manuscript).
Hong et al., "Cell Microarray Technologies for High-Throughput Cell-Based Biosensors," Sensors (Basel), Jun. 5, 2017, 17(6):1293.

* cited by examiner

800

803

802

810

Tissue

Reagent drop 805     806

810

804

Array Slide

825

803     850     802

810

810

Flow will deflect
diffusive transfer
of molecules

804

Array Slide 805     806

TCR mapping

BCR mapping

METHODS, COMPOSITIONS, AND KITS FOR DETERMINING THE LOCATION OF MULTIPLE ANALYTES IN A BIOLOGICAL SAMPLE

CROSS-REFERENCE TO RELATED APPLICATIONS

Pursuant to 35 U.S.C. § 119 (c), this application is a continuation of International Application PCT/US2023/079071, with an international filing date of Nov. 8, 2023, which claims the benefit of priority to U.S. Provisional Patent Application No. 63/424,056, filed on Nov. 9, 2022, the contents of which are incorporated herein by in its entirety.

SEQUENCE LISTING

This application contains a Sequence Listing that has been submitted electronically as an XML file named "47706-0333001_ST26_SL.XML." The XML file, created on Jan. 16, 2025, is 2,842 bytes in size. The material in the XML file is hereby incorporated by reference in its entirety.

BACKGROUND

Cells within a tissue of a subject have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, signaling and cross-talk with other cells in the tissue.

Spatial heterogeneity has been previously studied using techniques that only provide data for a small number of analytes in the context of an intact tissue or a portion of a tissue, or provide substantial analyte data for dissociated tissue (e.g., single cells), but fail to provide information regarding the position of the single cell in a parent biological sample (e.g., tissue sample).

Sequencing nucleic acid libraries generated from spatial array analysis generally biases capture to sequences from 3' end of the captured analytes. However, 5' end sequences can contain valuable information about the target analyte. Thus, strategies are needed to sequence regions more than about 1 kilobase away from 3' end of analytes, such as 5'ends, in nucleic acid libraries generated from spatial array analysis. Additionally, combining techniques to sequence regions more than about 1 kilobase away from 3' end of analytes with other capture techniques allows for multiplex capture of analytes from a biological sample.

SUMMARY

The present disclosure features methods of capturing analytes on a spatial array, where the spatial array includes a plurality of capture probes and a capture probe of the plurality of capture probes includes a spatial barcode and a capture domain. Since capture on a spatial array can be generally biased toward the capture 3' end sequences of nucleic acid analytes, methods are still needed to capture 5' ends of the nucleic acid analytes or complements thereof. For example, target RNA nucleic acid analytes can be reverse transcribed with a primer including a sequence complementary to a target nucleic acid and a functional domain (e.g., a sequencing adapter) to generate an RNA/DNA (e.g., cDNA duplex). The reverse transcriptase can incorporate a non-templated polynucleotide sequence to the end of the cDNA that hybridizes to the capture domain of the capture probe (e.g., a second capture probe). The target nucleic acid can also be digested resulting in a single-stranded cDNA product that is captured by a capture probe on the array. In addition, such methods for capturing 5' end of nucleic acid analytes can be combined with additional capture techniques that capture nucleic acids that serve as a proxy for a nucleic acid analyte. For example, pairs of probes specific to a target nucleic acid can hybridize to a nucleic acid target and subsequently be ligated (e.g., nucleic acid templated ligation). At least one probe of the pair of probes can include a nucleic acid sequence that hybridizes to the capture domain of a capture probe (e.g., a first capture probe). Thus, a proxy of a target nucleic acid can be captured (e.g., to permit general gene expression analysis) in conjunction with capture products that permit analysis of 5' proximal sequences of target nucleic acids (e.g., encoding for immune cell receptors).

Thus, provided herein are methods for determining a location of a first target nucleic acid and a second target nucleic acid in a biological sample, the method including: (a) contacting the biological sample with: (i) a first probe and a second probe, where the first probe and the second probe each include sequences that are substantially complementary to sequences of the first target nucleic acid, and where the second probe includes a first capture sequence that is complementary to all or a portion of a first capture domain; and (ii) a first primer including a sequence that hybridizes to a complementary sequence in the second target nucleic acid, and a functional domain; (b) hybridizing the first probe and the second probe to the first target nucleic acid; (c) generating a ligation product by ligating the first probe to the second probe; (d) hybridizing the first capture sequence of the ligation product to the first capture domain on an array, where the array includes a first plurality of capture probes, where a first capture probe of the first plurality of capture probes includes: a first spatial barcode and the first capture domain; (c) hybridizing the first primer to the second target nucleic acid and extending the first primer using the second target nucleic acid as a template to generate an extension product; (f) incorporating a polynucleotide sequence including at least three nucleotides to the 3' end of the extension product; (g) hybridizing a second primer to the polynucleotide sequence of the extension product of step (f), where the second primer includes a second capture sequence; (h) extending the extension product of step (g) using the second primer as a template, thereby incorporating a complement of the second capture sequence into the extension product; (i) hybridizing the complement of the second capture sequence of the extension product of (h) to a second capture domain on the array, where the array includes a second plurality of capture probes, where a second capture probe of the second plurality of capture probes includes: a second spatial barcode and the second capture domain; (j) determining (i) the sequence of the first spatial barcode, or a complement thereof, and (ii) all or a portion of the sequence of the ligation product (corresponding to a sequence of the first target nucleic acid) hybridized to the first capture domain, or a complement thereof, and using the determined sequences of (i) and (ii) to determine the location of the first target nucleic acid in the biological sample; and (k) determining (iii) the sequence of the second spatial barcode, or a complement thereof, and (iv) all or a portion of the sequence of the extension product corresponding to a sequence of the second target nucleic acid, or a complement thereof, and using the determined sequences of (iii) and (iv) to determine the location of the second target nucleic acid in the biological sample.

In some embodiments, the biological sample is disposed on the array including the first plurality and the second plurality of capture probes. In some embodiments, the biological sample is disposed on a first substrate, and where the array including the first and second plurality of capture probes is disposed on a second substrate. In some embodiments, the method includes aligning the first substrate with the second substrate, such that at least a portion of the biological sample is aligned with at least a portion of the second substrate, e.g., the array on the second substrate.

In some embodiments, the hybridizing in steps (d) and/or (i) include passive migration of the ligation product and/or the extension product from the biological sample to the array. In some embodiments, the hybridizing in steps (d) and/or (i) include active migration of the ligation product and/or the extension product from the biological sample to the array, and, optionally, where the active migration includes electrophoresis.

In some embodiments, the polynucleotide sequence in step (f) includes a homopolynucleotide sequence, optionally 5'-CCC-3'. In some embodiments, the polynucleotide sequence in step (f) includes a heteropolynucleotide sequence, optionally 5'-CGC-3'.

In some embodiments, the first capture domain includes a first fixed sequence. In some embodiments, the second capture domain includes a second fixed sequence. In some embodiments, the first capture domain and the second capture domain have the same sequence. In some embodiments, the first capture domain and the second capture domain have a different sequence.

In some embodiments, the first primer includes a random sequence. In some embodiments, the random sequence includes a random hexamer. In some embodiments, the random sequence includes a random decamer. In some embodiments, the first primer includes a homopolymer sequence. In some embodiments, the homopolymer sequence includes a poly(T) sequence.

In some embodiments, the first primer includes a sequence substantially complementary to a sequence in the second target nucleic acid encoding a constant region of an antibody. In some embodiments, the first primer includes a sequence substantially complementary to a sequence in the second target nucleic acid encoding a constant region of a B cell receptor. In some embodiments, the first primer includes a sequence substantially complementary to a sequence in the second target nucleic acid encoding a constant region of a T cell receptor. In some embodiments, the functional domain includes a primer binding site or a sequencing specific site.

In some embodiments, the first target nucleic acid is RNA. In some embodiments, the RNA is mRNA. In some embodiments, the first target nucleic acid is DNA. In some embodiments, the second target nucleic acid is RNA. In some embodiments, the RNA is mRNA. In some embodiments, the mRNA includes a sequence encoding a B cell receptor or a fragment thereof. In some embodiments, the mRNA includes a sequence encoding a T cell receptor or a fragment thereof. In some embodiments, the mRNA includes a sequence that does not encode a B cell receptor or a fragment thereof or a T cell receptor or a fragment thereof.

In some embodiments, the extending in step (e) includes the use of a reverse transcriptase.

In some embodiments, incorporating the polynucleotide sequence to the 3' end of the extension product in step (f)

includes the use of a terminal deoxynucleotidyl transferase. In some embodiments, incorporating the polynucleotide sequence to the 3' end of the extension product in step (f) includes the use of a reverse transcriptase.

In some embodiments, the second primer includes RNA.

In some embodiments, the method includes removing the second target nucleic acid or any other nucleic acid hybridized to the extension product before the complement of the second capture sequence of the extension product hybridizes to the second capture domain of the second capture probe. In some embodiments, the method includes removing the first target nucleic acid, or any other nucleic acid hybridized to the ligation product, before the first capture sequence of the ligation product hybridizes to the first capture domain of the first capture probe. In some embodiments, the removing includes the use of an RNase. In some embodiments, the RNase is RNase H. In some embodiments, the removing includes use of heat.

In some embodiments, the method includes a step of extending 3' end of the extension product of step (i) using the second capture probe as a template, thereby generating an extended capture product; and/or extending the second capture probe using the extension product of step (i) as a template, thereby generating a second extended capture probe; and/or a step of extending 3' end of the ligation product using the first capture probe as a template, thereby generating an extended ligation product; and/or extending the first capture probe using the ligation product as a template, thereby generating a first extended capture probe.

In some embodiments, the extended capture product is removed from the second capture probe on the array and/or the extended ligation product is removed from the first capture probe on the array. In some embodiments, the removing includes use of heat. In some embodiments, the removing includes use of potassium hydroxide (KOH).

In some embodiments, the first spatial barcode and the second spatial barcode have the same sequence. In some embodiments, the first spatial barcode and the second spatial barcode have a different sequence.

In some embodiments, the determining in step (j) includes sequencing. In some embodiments, the determining in step (k) includes sequencing. In some embodiments, the sequencing includes high-throughput sequencing.

In some embodiments, step (e) is performed after step (c). In some embodiments, step (c) is performed before step (c).

In some embodiments, the first capture sequence and the second capture sequence include the same sequence. In some embodiments, the first capture sequence and the second capture sequence include different sequences.

Also provided herein are methods for determining a location of a first target nucleic acid and a second target nucleic acid in a biological sample, the method including: (a) contacting the biological sample with: (i) a first probe and a second probe, where the first probe and the second probe each include sequences that are substantially complementary to sequences of the first target nucleic acid, and where the second probe includes a first capture sequence that is complementary to all or a portion of a first capture domain; and (ii) a plurality of primers, where the plurality of primers includes nucleic acid sequences that hybridize to complementary sequences in the second target nucleic acid and a functional domain; (b) hybridizing the first probe and the second probe to the first target nucleic acid; (c) generating a ligation product by ligating the first probe to the second probe; (d) hybridizing the first capture sequence of the ligation product to a first capture domain on an array, where the array includes a first plurality of capture probes, where a first capture probe of the plurality of first capture probes includes: a first spatial barcode and the first capture domain; (c) hybridizing one or more of the plurality of primers to the second target nucleic acid and extending the one or more of the plurality of primers using the second target nucleic acid as a template to generate one or more extension products; (f) incorporating a polynucleotide sequence including at least three nucleotides to the 3' end of the one or more extension products; (g) hybridizing a second primer to the polynucleotide sequence of the one or more extension products of step (f), where the second primer includes a second capture sequence; (h) extending the one or more extension products of step (g) using the second primer as a template, thereby incorporating a complement of the second capture sequence into the one or more extension products; (i) hybridizing the complement of the second capture sequence of the one or more extension products of (h) to a second capture domain on the array, where the array includes a second plurality of capture probes, where a second capture probe of the second plurality of capture probes includes: a second spatial barcode and the second capture domain; (j) determining (i) the sequence of the first spatial barcode, or a complement thereof, and (ii) all or a portion of the sequence of the ligation product hybridized to the first capture domain, or a complement thereof, and using the determined sequences of (i) and (ii) to determine the location of the first target nucleic acid in the biological sample; and for an extension product in the one or more extension products (k) determining (iii) the sequence of the second spatial barcode, or a complement thereof, and (iv) all or a portion of the sequence of one of the one or more extension products corresponding to a sequence of the second target nucleic acid, or a complement thereof, and using the determined sequences of (iii) and (iv) to determine the location of the second target nucleic acid in the biological sample.

In some embodiments, the biological sample is disposed on the array including the first plurality and the second plurality of capture probes. In some embodiments, the biological sample is disposed on a first substrate, and where the array including the first and second plurality of capture probes is disposed on a second substrate. In some embodiments, the method includes aligning the first substrate with the second substrate, such that at least a portion of the biological sample is aligned with at least a portion of the second substrate.

In some embodiments, the hybridizing in steps (d) and/or (i) include passive migration of the ligation product and/or the one or more extension products from the biological sample to the array. In some embodiments, the hybridizing in steps (d) and/or (i) include active migration of the ligation product and/or the one or more extension products from the biological sample to the array, and optionally, where the active migration includes electrophoresis.

In some embodiments, incorporating the polynucleotide sequence in step (f) includes a homopolynucleotide sequence, optionally 5'-CCC-3'. In some embodiments, incorporating the polynucleotide sequence in step (f) includes a heteropolynucleotide sequence, optionally 5'-CGC-3'.

In some embodiments, the first capture domain includes a fixed sequence. In some embodiments, the second capture domain includes a fixed sequence. In some embodiments, the first capture domain and the second capture domain have the same sequence. In some embodiments, the first capture domain and the second capture domain have a different sequence. In some embodiments, one or more primers of the plurality of primers includes a random sequence. In some embodiments, the random sequence includes a random hexamer. In some embodiments, the random sequence includes a random decamer. In some embodiments, one or more primers of the plurality of primers includes a homopolymer sequence. In some embodiments, the homopolymer sequence includes a poly(T) sequence.

In some embodiments, one or more primers of the plurality of primers includes a sequence substantially complementary to a sequence in the second target nucleic acid encoding a constant region of an antibody. In some embodiments, one or more primers of the plurality of primers includes a sequence substantially complementary to a sequence in the second target nucleic acid encoding a B cell receptor. In some embodiments, one or more primers of the plurality of primers includes a sequence substantially complementary to a sequence in the second target nucleic acid encoding a T cell receptor.

In some embodiments, the functional domain includes a primer binding site or a sequencing specific site.

In some embodiments, the first target nucleic acid is RNA. In some embodiments, the RNA is mRNA. In some embodiments, the first target nucleic acid is DNA. In some embodiments, the second target nucleic acid is RNA. In some embodiments, the RNA is mRNA. In some embodiments, the mRNA includes a sequence encoding a B cell receptor or a fragment thereof. In some embodiments, the mRNA includes a sequence encoding a T cell receptor or a fragment thereof. In some embodiments, the mRNA includes a sequence that does not encode a B cell receptor or a fragment thereof or a T cell receptor or a fragment thereof.

In some embodiments, incorporating the polynucleotide sequence to the 3' end of the one or more extension products in step (f) includes the use of a terminal deoxynucleotidyl transferase. In some embodiments, incorporating the polynucleotide sequence to the 3' end of the one or more extension products in step (f) includes the use of a reverse transcriptase. In some embodiments, the second primer includes RNA.

In some embodiments, the method includes removing the second target nucleic acid, or any other nucleic acid hybridized, to the one or more extension products before the complement of the second capture sequence of the one or more extension products hybridizes to the second capture domain of the second capture probe. In some embodiments, the method includes removing the first target nucleic acid, or any other nucleic acid hybridized to the ligation product, before the first capture sequence of the ligation product hybridizes to the first capture domain of the first capture probe. In some embodiments, the removing includes the use of an RNase. In some embodiments, the RNase includes RNase H. In some embodiments, the removing includes use of heat.

In some embodiments, the method includes a step of extending 3' end of the one or more extensions product of step (i) using the second capture probe as a template, thereby generating one or more extended capture products; and/or extending the second capture probe using the extension product of step (i) as a template, thereby generating a second extended capture probe; and/or extending 3' end of the ligation product using the first capture probe as a template, thereby generating an extended ligation product; and/or extending the first capture probe using the ligation product as a template, thereby generating a first extended capture probe.

In some embodiments, the extended capture product is removed from the second capture probe; and/or the extended ligation product is removed from the first capture probe. In some embodiments, the removing includes use of heat. In some embodiments, the removing includes use of KOH.

In some embodiments, the first spatial barcode and the second spatial barcode have the same sequence. In some embodiments, the first spatial barcode and the second spatial barcode have a different sequence.

In some embodiments, the determining in step (j) includes sequencing. In some embodiments, the determining in step (k) includes sequencing. In some embodiments, the sequencing includes high-throughput sequencing.

In some embodiments, the extending in step (e) includes the use of a reverse transcriptase.

In some embodiments, the plurality of primers hybridize to different sequences in the second target nucleic acid. In some embodiments, two or more primers of the plurality of primers hybridize to different sequences in the second target nucleic acid. In some embodiments, ten or more primers of the plurality of primers hybridize to different sequences in the second target nucleic acid. In some embodiments, fifty or more primers of the plurality of primers hybridize to different sequences in the second target nucleic acid. In some embodiments, one hundred or more primers of the plurality of primers hybridize to different sequences in the second target nucleic acid.

In some embodiments, the reverse transcriptase has strand displacement activity. In some embodiments, the strand displacement activity of the reverse transcriptase displaces one or more primers of the plurality of primers from the second target nucleic acid. In some embodiments, the strand displacement activity of the reverse transcriptase displaces the one or more extension products from the second target nucleic acid.

In some embodiments, the extending in step (f) includes the use of a reverse transcriptase and a helicase. In some embodiments, the method includes use of one or more single-stranded DNA binding proteins. In some embodiments, the one or more single-stranded DNA binding proteins includes one or more of: Tth RecA, E. coli RecA, T4 gp32 and ET-SSB. In some embodiments, the helicase has strand displacement activity.

In some embodiments, the extending in step (f) includes the use of a superhelicase and a reverse transcriptase. In some embodiments, the superhelicase is selected from the group consisting of: Rep, PrcA, UvrB, RecBCD, and Tte-Uvrd.

In some embodiments, step (e) is performed after step (c). In some embodiments, step (c) is performed before step (c).

In some embodiments, the first capture sequence and the second capture sequence include the same sequence. In some embodiments, the first capture sequence and the second capture sequence include different sequences.

Also provided herein are methods for determining a location of a first target nucleic acid and a second target nucleic acid in a biological sample, the method including: (a) contacting the biological sample with: (i) a first probe and a second probe, where the first probe and the second probe each include sequences that are substantially complementary to sequences of the first target nucleic acid, and where the second probe includes a first capture sequence that is complementary to all or a portion of a first capture domain; and (ii) a primer including a sequence that hybridizes to a complementary sequence in the second target nucleic acid and a functional domain; (b) hybridizing the first probe and the second probe to the first target nucleic acid; (c) generating a ligation product by ligating the first probe to the second probe; (d) hybridizing the first capture sequence of the ligation product to the first capture domain on the array, where the array includes a first plurality of capture probes, where a first capture probe of the first plurality of capture probes includes: a first spatial barcode and the first capture domain; (e) hybridizing the primer to the second target nucleic acid and extending the primer using the second target nucleic acid as a template to generate an extension product; (f) incorporating a polynucleotide sequence including at least three nucleotides to the 3' end of the extension product; (g) hybridizing the polynucleotide sequence of the extension product to a second capture domain on an array, where the array includes a second plurality of capture probes, where a second capture probe of the second plurality of capture probes includes: a second spatial barcode and the second capture domain; (h) determining (i) the sequence of the first spatial barcode, or a complement thereof, and (ii) all or a portion of the sequence of the ligation product hybridized to the first capture domain, or a complement thereof, and using the determined sequences of (i) and (ii) to determine the location of the first target nucleic acid in the biological sample; and (i) determining (iii) the sequence of the second spatial barcode, or a complement thereof, and (iv) all or a portion of the sequence of the extension product corresponding to a sequence of the second target nucleic acid, or a complement thereof, and using the determined sequences of (iii) and (iv) to determine the location of the second target nucleic acid in the biological sample.

In some embodiments, the biological sample is disposed on the array including the first and the second plurality of capture probes. In some embodiments, the biological sample is disposed on a first substrate, and where the array including the first and second plurality of capture probes is disposed on a second substrate. In some embodiments, the method includes aligning the first substrate with the second substrate, such that at least a portion of the biological sample is aligned with at least a portion of the second substrate.

In some embodiments, the hybridizing in steps (d) and (g) include passive migration of the ligation product and/or the extension product from the biological sample to the array. In some embodiments, the hybridizing in steps (d) and (g) include active migration of the ligation product and/or the extension product from the biological sample to the array, and optionally, where the active migration includes electrophoresis.

In some embodiments, the polynucleotide sequence in step (f) includes a homopolynucleotide sequence, optionally 5'-CCC-3'. In some embodiments, the polynucleotide sequence in step (f) includes a heteropolynucleotide sequence, optionally 5'-CGC-3'.

In some embodiments, the first capture domain includes a fixed sequence. In some embodiments, the second capture domain includes a fixed sequence. In some embodiments, the first capture domain and the second capture domain have the same sequence. In some embodiments, the first capture domain and the second capture domain have a different sequence.

In some embodiments, the primer includes a random sequence. In some embodiments, the random sequence includes a random hexamer. In some embodiments, the random sequence includes a random decamer. In some embodiments, the primer includes a homopolymer sequence. In some embodiments, the homopolymer sequence includes a poly(T) sequence.

In some embodiments, the primer includes a sequence substantially complementary to a sequence in the second target nucleic acid encoding an antibody. In some embodiments, the primer includes a sequence substantially complementary to a sequence in the second target nucleic acid encoding a constant region of a B cell receptor. In some embodiments, the first primer includes a sequence substantially complementary to a sequence in the second target nucleic acid encoding a constant region of a T cell receptor.

In some embodiments, the functional domain includes a primer binding site or a sequencing specific site.

In some embodiments, the first target nucleic acid is RNA. In some embodiments, the RNA is mRNA. In some embodiments, the first target nucleic acid is DNA. In some embodiments, the second target nucleic acid is RNA. In some embodiments, the RNA is mRNA. In some embodiments, the mRNA includes a sequence encoding a B cell receptor or a fragment thereof. In some embodiments, the mRNA includes a sequence encoding a T cell receptor or a fragment thereof. In some embodiments, the mRNA includes a sequence that does not encode a B cell receptor or a fragment thereof or a T cell receptor or a fragment thereof.

In some embodiments, the extending in step (e) includes the use of a reverse transcriptase.

In some embodiments, incorporating the polynucleotide sequence to the 3' end of the extension product in step (f) includes the use of a terminal deoxynucleotidyl transferase. In some embodiments, incorporating the polynucleotide sequence to the 3' end of the extension product in step (f) includes the use of a reverse transcriptase.

In some embodiments, the method includes removing the first target nucleic acid, or any other nucleic acid hybridized to the ligation product, before the first capture sequence hybridizes to the first capture domain of the first capture probe; and/or removing the second target nucleic acid, or any other nucleic acid hybridized to the extension product, before the polynucleotide sequence hybridizes to the second capture domain of the second capture probe. In some embodiments, the removing includes the use of an RNase. In some embodiments, the RNase is RNase H. In some embodiments, the removing includes use of heat.

In some embodiments, the method includes a step of extending a 3' end of the extension product of step (g) using the second capture probe as a template, thereby generating an extended capture product; and/or extending the second capture probe using the extension product of step (g) as a template, thereby generating a second extended capture probe; and/or extending 3' end of the ligation product using the first capture probe as a template, thereby generating an extended ligation product; and/or extending the first capture probe using the ligation product as a template, thereby generating a first extended capture probe.

In some embodiments, the extended capture product is removed from the second capture probe; and/or the extended ligation product is removed from the first capture probe. In some embodiments, the removing includes use of heat. In some embodiments, the removing includes use of KOH.

In some embodiments, the first spatial barcode and the second spatial barcode have the same sequence. In some embodiments, the first spatial barcode and the second spatial barcode have a different sequence.

In some embodiments, the determining in step (h) includes sequencing. In some embodiments, the determining in step (i) includes sequencing. In some embodiments, the sequencing includes high-throughput sequencing.

In some embodiments, step (e) is performed after step (c). In some embodiments, step (c) is performed before step (c).

In some embodiments, the first capture sequence and the second capture sequence include the same sequence. In some embodiments, the first capture sequence and the second capture sequence include different sequences.

Also provided herein are method for determining a location of a first target nucleic acid and a second target nucleic acid in a biological sample, the method including: (a) contacting the biological sample with: (i) a first probe and a second probe, where the first probe and the second probe each include sequences that are substantially complementary to sequences of the first target nucleic acid, and where the second probe includes a first capture sequence that is complementary to all or a portion of a first capture domain; and (ii) a plurality of primers, where the plurality of primers include nucleic acid sequences that hybridize to complementary sequences in the second target nucleic acid and a functional domain; (b) hybridizing the first probe and the second probe to the first target nucleic acid; (c) generating a ligation product by ligating the first probe to the second probe; (d) hybridizing the ligation product to the first capture domain of the first capture probe; (c) hybridizing one or more of the plurality of primers to the second target nucleic acid and extending the one or more of the plurality of primers using the second target nucleic acid as a template to generate one or more extension products; (f) incorporating a polynucleotide sequence including at least three nucleotides to the 3' end of the one or more extension products; (g) hybridizing the polynucleotide sequence of the one or more extension products to the second capture domain of the second capture probe; (h) determining (i) the sequence of the first spatial barcode, or a complement thereof, and (ii) all or a portion of the sequence of the ligation product hybridized to the first capture domain, or a complement thereof, and using the determined sequences of (i) and (ii) to determine the location of the first target nucleic acid in the biological sample; and for an extension product in the one or more extension products (i) determining (iii) the sequence of the second spatial barcode, or a complement thereof, and (iv) all or a portion of the sequence of one of the one or more extension products corresponding to a sequence of the second target nucleic acid, or a complement thereof, and using the determined sequences of (iii) and (iv) to determine the location of the second target nucleic acid in the biological sample.

In some embodiments, the biological sample is disposed on the array including the first plurality and the second plurality of capture probes. In some embodiments, the biological sample is disposed on a first substrate, and where the array including the first and second plurality of capture probes is disposed on a second substrate. In some embodiments, the method includes aligning the first substrate with the second substrate, such that at least a portion of the biological sample is aligned with at least a portion of the second substrate.

In some embodiments, the hybridizing in steps (d) and/or (g) include passive migration of the ligation product and/or the one or more extension products from the biological sample to the array. In some embodiments, the hybridizing in steps (d) and/or (g) include active migration of the ligation product and/or the one or more extension products from the biological sample to the array, and optionally, where the active migration includes electrophoresis.

In some embodiments, incorporating the polynucleotide sequence in step (f) includes a homopolynucleotide sequence, optionally 5'-CCC-3'. In some embodiments, incorporating the polynucleotide sequence in step (f) includes a heteropolynucleotide sequence, optionally 5'-CGC-3'.

In some embodiments, the first capture domain includes a first fixed sequence. In some embodiments, the second capture domain includes a second fixed sequence.

In some embodiments, the first capture domain and the second capture domain have the same sequence. In some embodiments, the first capture domain and the second capture domain have different sequences. In some embodiments, the plurality of primers includes a random sequence. In some embodiments, the random sequence includes a random hexamer.

In some embodiments, the random sequence includes a random decamer. In some embodiments, the plurality of primers includes a homopolymer sequence. In some embodiments, the homopolymer sequence includes a poly (T) sequence.

In some embodiments, the plurality of primers includes a sequence substantially complementary to a sequence in the second target nucleic acid encoding a constant region of an antibody. In some embodiments, the plurality of primers includes a sequence substantially complementary to a sequence in the second target nucleic acid encoding a constant region of a B cell receptor or a fragment thereof. In some embodiments, the plurality of primers includes a sequence substantially complementary to a sequence in the second target nucleic acid encoding a constant region of a T cell receptor or a fragment thereof.

In some embodiments, the functional domain includes a primer binding site or a sequencing specific site.

In some embodiments, the first target nucleic acid is RNA. In some embodiments, the RNA is mRNA. In some embodiments, the first target nucleic acid is DNA. In some embodiments, the second target nucleic acid is RNA. In some embodiments, the RNA is mRNA. In some embodiments, the mRNA includes a sequence encoding a T cell receptor or a fragment thereof. In some embodiments, the mRNA includes a sequence encoding a B cell receptor or a fragment thereof. In some embodiments, the mRNA includes a sequence that does not encode a B cell receptor or a fragment thereof or a T cell receptor or a fragment thereof.

In some embodiments, the extending in step (c) includes the use of a reverse transcriptase.

In some embodiments, incorporating the polynucleotide sequence to the 3' end of the one or more extension products in step (f) includes the use of a terminal deoxynucleotidyl transferase. In some embodiments, incorporating the polynucleotide sequence to the 3' end of the one or more extension products in step (f) includes the use of a reverse transcriptase.

In some embodiments, the method includes removing the first target nucleic acid, or any other nucleic acid hybridized to the ligation product, before the first capture sequence of the ligation product hybridizes to the first capture domain of the first capture probe. In some embodiments, the method includes removing the second target nucleic acid, or any other nucleic acid hybridized to the one or more extension products, before the polynucleotide sequence hybridizes to the second capture domain of the second capture probe. In some embodiments, the removing includes the use of an RNase. In some embodiments, the RNase is RNase H. In some embodiments, the removing includes use of heat.

In some embodiments, the method includes a step of extending a 3' end of the one or more extension products of step (f) using the second capture probe as a template, thereby generating one or more extended capture products; and/or extending the second capture probe using the extension product of step (f) as a template, thereby generating a second extended capture probe; and/or a step of extending a 3' end of the ligation product using the first capture probe as a template, thereby generating an extended ligation product; and/or extending the first capture probe using the ligation product as a template, thereby generating a first extended capture probe.

In some embodiments, the extended ligation product is removed from the first capture probe and/or the one or more extended capture products are removed from the second capture probes on the array. In some embodiments, the removing includes use of heat. In some embodiments, the removing includes use of KOH.

In some embodiments, the first spatial barcode and the second spatial barcode have the same sequence. In some embodiments, the first spatial barcode and the second spatial barcode have a different sequence.

In some embodiments, the determining in step (h) includes sequencing. In some embodiments, the determining in step (i) includes sequencing. In some embodiments, the sequencing includes high-throughput sequencing.

In some embodiments, the plurality of primers hybridize to different sequences in the second target nucleic acid. In some embodiments, two or more primers of the plurality of primers hybridize to different sequences in the second target nucleic acid. In some embodiments, ten or more primers of the plurality of primers hybridize to different sequences in the second target nucleic acid. In some embodiments, fifty or more primers of the plurality of primers hybridize to different sequences in the second target nucleic acid. In some embodiments, 100 or more primers of the plurality of primers hybridize to different sequences in the second target nucleic acid.

In some embodiments, the reverse transcriptase has strand displacement activity. In some embodiments, the strand displacement activity of the reverse transcriptase displaces one or more primers of the plurality of primers from the second target nucleic acid. In some embodiments, the strand displacement activity of the reverse transcriptase displaces the one or more extension products from the second target nucleic acid.

In some embodiments, the extending in step (e) includes the use of a reverse transcriptase and a helicase. In some embodiments, the method includes one or more single-stranded DNA binding proteins. In some embodiments, the one or more single-stranded DNA binding proteins includes one or more of: Tth RecA, E. coli RecA, T4 gp32 and ET-SSB.

In some embodiments, the extending in step (e) includes the use of a superhelicase and a reverse transcriptase. In some embodiments, the superhelicase is selected from the group consisting of: Rep, PrcA, UvrB, RecBCD, and Tte-Uvrd. In some embodiments, the superhelicase has strand displacement activity.

In some embodiments, the method includes generating two or more extension products from a primer of the plurality of primers. In some embodiments, the one or more extension products include different sequence lengths.

In some embodiments, the first probe and the second probe are substantially complementary to adjacent sequences of the first target nucleic acid. In some embodiments, the first probe and the second probe hybridize to sequences that are not adjacent to each other on the first target nucleic acid. In some embodiments, the first probe is extended with a DNA polymerase, thereby (i) filling in a gap between the first probe and the second probe and (ii) generating an extended first probe.

In some embodiments, contacting the first probe and the second probe with the biological sample includes contacting the biological sample with 5000 or more probe pairs, where a probe pair of the 5000 or more probe pairs includes the first probe and the second probe.

In some embodiments, generating the ligation product includes ligating the first probe to the second probe using enzymatic ligation or chemical ligation. In some embodiments, the enzymatic ligation utilizes a ligase. In some embodiments, the ligase is one or more of a T4 RNA ligase (Rnl2), a SplintR ligase (e.g., a PBCV-1 DNA Ligase, a Chlorella virus DNA ligase), a single stranded DNA ligase, or a T4 DNA ligase.

In some embodiments, the first probe includes a primer sequence.

In some embodiments, the method includes providing a blocking moiety that interacts with the first capture domain of the first capture probe. In some embodiments, the method includes releasing the blocking moiety from the first capture domain of the first capture probe prior to hybridizing the first capture sequence of the ligation product to the first capture domain.

In some embodiments, the first capture sequence includes a poly-adenylated sequence. In some embodiments, the blocking moiety includes a poly-uridine sequence, a poly-thymidine sequence, or both.

In some embodiments, the first probe and/or the second probe is a DNA probe.

In some embodiments, the blocking moiety is a DNA probe. In some embodiments, the blocking moiety from the first capture domain of the first capture probe includes contacting the biological sample with an endoribonuclease.

Also provided herein are methods for determining a location of a target nucleic acid in a biological sample, the method including: (a) contacting the biological sample with a first probe and a second probe, where: (i) the first probe includes a sequence that is substantially complementary to a sequence of the target nucleic acid and a functional domain, and (ii) the second probe includes a sequence that is substantially complementary to a sequence of the target nucleic acid and a capture sequence that is complementary to all or a portion of a capture domain; (b) hybridizing the first probe and the second probe to the target nucleic acid, where the first probe and the second probe hybridize to non-adjacent sequences; (c) generating a sequence complementary to the target nucleic acid between the first probe and second probe using the target nucleic acid as a template by gap-filling, thereby by generating an extension product; (d) ligating the extension product to the first probe or the second probe, thereby generating a ligation product; (e) hybridizing the capture sequence of the ligation product to a capture domain on an array, where the array includes a plurality of capture probes, where a capture probe of the plurality of capture probes includes a spatial barcode and the capture domain; and (f) determining (i) the sequence of the spatial barcode, or a complement thereof, and (ii) all or a portion of the sequence of the ligation product hybridized to the capture domain, or a complement thereof, and using the determined sequences of (i) and (ii) to determine the location of the target nucleic acid in the biological sample.

In some embodiments, the biological sample is disposed on the array including the plurality of capture probes. In some embodiments, the biological sample is disposed on a first substrate, and where the array including the plurality of capture probes is disposed on a second substrate. In some embodiments, the method includes aligning the first substrate with the second substrate, such that at least a portion of the biological sample is aligned with at least a portion of the second substrate.

In some embodiments, the hybridizing in step (c) includes passive migration of the ligation product from the biological sample to the array. In some embodiments, the hybridizing in step (c) includes active migration of the ligation product from the biological sample to the array, and optionally, where the active migration includes electrophoresis.

In some embodiments, the gap-filling in step (b) includes the use of a DNA polymerase or a reverse transcriptase. In some embodiments, generating the sequence complementary to the target nucleic acid in step (c) includes extending the first probe. In some embodiments, generating the sequence complementary to the target nucleic acid in step (c) includes extending the second probe.

In some embodiments, contacting the first probe and the second probe with the biological sample includes contacting the biological sample with 5000 or more probe pairs, where a probe pair of the 5000 or more probe pairs includes the first probe and the second probe.

In some embodiments, generating the ligation product includes ligating the extension product to the first probe or the second probe using enzymatic ligation or chemical ligation. In some embodiments, the enzymatic ligation utilizes a ligase. In some embodiments, the ligase is one or more of a T4 RNA ligase (Rnl2), a SplintR ligase (e.g., a PBCV-1 DNA Ligase, a Chlorella virus DNA ligase), a single-stranded DNA ligase, or a T4 DNA ligase.

In some embodiments, the functional domain includes a primer binding sequence or a sequencing specific site.

In some embodiments, the method includes providing a blocking moiety that interacts with the capture domain of the capture probe. In some embodiments, the method includes releasing the blocking moiety from the capture domain of the capture probe.

In some embodiments, the capture sequence includes a poly-adenylated sequence. In some embodiments, the capture sequence includes a fixed sequence. In some embodiments, the fixed sequence is a homopolynucleotide sequence. In some embodiments, the fixed sequence is a heteropolynucleotide sequence.

In some embodiments, the blocking moiety includes a poly-uridine sequence, a poly-thymidine sequence, or both.

In some embodiments, the first probe and/or the second probe is a DNA probe. In some embodiments, the first probe and/or the second probe is an RNA probe. In some embodiments, the blocking moiety is a DNA probe. In some embodiments, releasing the blocking moiety from the capture domain of the capture probe includes contacting the biological sample with an endoribonuclease. In some embodiments, releasing the ligation product from the target nucleic acid includes contacting the biological sample with an endoribonuclease. In some embodiments, the endoribonuclease is RNase H.

In some embodiments, the second probe includes one or more locked nucleic acids, one or more RNA nucleotides, or both.

In some embodiments, the first probe includes a sequence complementary to a sequence in the target nucleic acid encoding a constant region of an antibody. In some embodiments, the first probe includes a sequence complementary to a sequence in the target nucleic acid encoding a constant region of a B cell receptor. In some embodiments, the first probe includes a sequence complementary to a sequence in the target nucleic acid encoding a constant region of a T cell receptor.

In some embodiments, the target nucleic acid is RNA or DNA. In some embodiments, the RNA is mRNA or the DNA is cDNA. In some embodiments, the mRNA includes a sequence encoding a B cell receptor or a fragment thereof. In some embodiments, the mRNA includes a sequence encoding a T cell receptor or a fragment thereof. In some embodiments, the mRNA includes a sequence that does not encode a B cell receptor or a fragment thereof or a T cell receptor or a fragment thereof.

In some embodiments, the second probe includes a sequence complementary to a sequence in the target nucleic acid encoding a variable region of a B cell receptor. In some embodiments, the second probe includes a sequence complementary to a sequence in the target nucleic acid encoding a variable region of a T cell receptor.

In some embodiments, the DNA polymerase or the reverse transcriptase lack strand displacement activity.

In some embodiments, the array includes one or more features.

In some embodiments, the method includes fixing the biological sample. In some embodiments, fixing the biological sample includes the use of a fixative selected from the group consisting of: ethanol, methanol, acetone, formaldehyde, paraformaldehyde-Triton, glutaraldehyde, and combinations thereof.

In some embodiments, the method includes staining the biological sample. In some embodiments, the staining includes use of eosin and/or hematoxylin. In some embodiments, the staining includes the use of a detectable label selected from the group consisting of a radioisotope, a fluorophore, a chemiluminescent compound, a bioluminescent compound, or a combination thereof.

In some embodiments, the method includes imaging the biological sample.

In some embodiments, the method includes a step of permeabilizing the biological sample. In some embodiments, the permeabilizing includes the use of an organic solvent, a detergent, an enzyme, or a combination thereof. In some embodiments, the permeabilizing includes the use of an endopeptidase, a protease, sodium dodecyl sulfate, polyethylene glycol tert-octylphenyl ether, polysorbate 80, and polysorbate 20, N-lauroylsarcosine sodium salt solution, saponin, Triton X-100™, Tween-20™, or combinations thereof. In some embodiments, the endopeptidase is pepsin or proteinase K.

In some embodiments, the capture probe, the first capture probe, and/or the second capture probe includes one or more functional domains, a unique molecular identifier, a cleavage domain, or combinations thereof.

In some embodiments, the biological sample is a tissue sample. In some embodiments, the tissue sample is a fixed tissue sample. In some embodiments, the fixed tissue sample is a formalin-fixed paraffin embedded tissue sample, a paraformaldehyde-fixed tissue sample, a methanol-fixed tissue sample, or an acetone-fixed tissue sample. In some embodiments, the tissue sample is a fresh frozen tissue sample. In some embodiments, the biological sample is a tissue section. In some embodiments, the tissue section is a fixed tissue section. In some embodiments, the fixed tissue section is a formalin-fixed paraffin embedded tissue section, a paraformaldehyde-fixed tissue section, a methanol-fixed tissue section, or an acetone-fixed tissue section. In some embodiments, the biological sample is a tissue microarray.

In some embodiments, the method includes contacting the biological sample with a third probe and a fourth probe, where: (i) the third probe includes a sequence that is substantially complementary to a sequence of a second target nucleic acid and a functional domain; (ii) the fourth probe includes a sequence that is substantially complementary to a sequence of the second target nucleic acid and a second capture sequence that is complementary to all or a portion of a second capture domain; hybridizing the third probe and the fourth probe to the second target nucleic acid; generating a second ligation product by ligating the third probe to the fourth probe; hybridizing the second capture sequence of the second ligation product to the second capture domain of a second capture probe on the array, where the second capture probe includes a second spatial barcode and the second capture domain; determining (i) the sequence of the second spatial barcode, or a complement thereof, and (ii) all or a portion of the ligation product, or a complement thereof, and using the determined sequences of (i) and (ii) to determine the location of the second target nucleic acid in the biological sample.

In some embodiments, the first capture domain and/or the second capture domain includes a fixed sequence. In some embodiments, the first capture domain and the second capture domain have the same sequence. In some embodiments, the first capture domain and the second capture domain have a different sequence.

In some embodiments, the second target nucleic acid is RNA or DNA. In some embodiments, the RNA is mRNA or the DNA is cDNA. In some embodiments, the mRNA includes a sequence encoding a B cell receptor or a fragment thereof. In some embodiments, the mRNA includes a sequence encoding a T cell receptor or a fragment thereof. In some embodiments, the mRNA includes a sequence that does not encode a B cell receptor or a fragment thereof or a T cell receptor or a fragment thereof.

In some embodiments, the method includes removing the second target nucleic acid, or any other nucleic acid hybridized to the second ligation product, before the second capture sequence hybridizes to the second capture domain of the second capture probe. In some embodiments, the removing includes the use of an RNase. In some embodiments, the RNase includes RNase H. In some embodiments, the removing includes the use of heat.

In some embodiments, the method includes a step of extending a 3' end of the second ligation product using the second capture probe as a template, thereby generating an extended ligation product; and/or extending the second capture probe using the second ligation product as a template, thereby generating a second extended capture probe.

Also provided herein are kits including: (a) an array including a plurality of first capture probes, where a first capture probe of the plurality of capture probes includes: (i) a first spatial barcode; and (ii) a first capture domain that binds a first capture sequence; and a second plurality of capture probes, where a second capture probe of the second plurality of capture probes includes: a second spatial barcode; and a second capture domain; (b) a first primer including a sequence complementary to a target nucleic acid, and a functional domain, where the functional domain includes a primer binding sequence or a sequencing specific sequence; (c) a second primer including a second capture sequence; (d) a plurality of probes including a first probe and a second probe, where the first probe and the second probe are substantially complementary to adjacent sequences of a target nucleic acid, where the second probe includes a first capture sequence that hybridizes the first capture domain; (c) a plurality of enzymes including a ribonuclease and a ligase; and (f) instructions for performing the methods described herein.

In some embodiments, the second primer includes RNA. In some embodiments, the kit includes a plurality of primers, where the first primer is included in the plurality of primers.

Also provided herein are kits including: (a) an array including a plurality of first capture probes, where a first capture probe of the plurality of capture probes includes: (i) a first spatial barcode; and (ii) a first capture domain that binds a first capture sequence; and a second plurality of capture probes, where a second capture probe of the second plurality of capture probes includes: a second spatial barcode; and a second capture domain; (b) a plurality of primers, where a primer of the plurality of primers includes a sequence complementary to a target nucleic acid and a functional domain, where the functional domain is a primer binding sequence or a sequencing specific site; (c) a plurality of probes including a first probe and a second probe, where the first probe and the second probe are substantially complementary to adjacent sequences of a target nucleic acid, where the second probe includes a first capture sequence that hybridizes to the first capture domain; (c) a plurality of enzymes including a ribonuclease and a ligase; and (f) instructions for performing the methods described herein.

In some embodiments, the first capture probe and/or the second capture probe include one or more additional functional domains, a unique molecular identifier, a cleavage domain, and combinations thereof.

In some embodiments, the kit includes a reverse transcriptase. In some embodiments, the kit includes a polymerase.

In some embodiments, the first capture domain and/or the second capture domain includes a fixed sequence.

In some embodiments, the kit includes a helicase. In some embodiments, the kit includes one or more single-stranded DNA binding proteins selected from the group consisting of: Tth RecA, *E. coli* RecA, T4 gp32 and ET-SSB.

In some embodiments, the kit includes a superhelicase, where the superhelicase is selected from the group consisting of: Rep, PrcA, UvrB, RecBCD, and Tte-Uvrd.

Also provided herein are compositions including: a) a first probe and a second probe hybridized to a first target nucleic acid and ligated together, where the first probe and the second probe each include a sequence that is substantially complementary to adjacent sequences of the first nucleic acid and where one of the first probe or the second probe includes a first capture sequence; and b) a plurality of primers hybridized to a second target nucleic acid.

Also provided herein are compositions including: a) a first probe and a second probe hybridized to a first target nucleic acid and ligated together, where the first probe and the second probe each include a sequence that is substantially complementary to adjacent sequences of the first nucleic acid and where one of the first probe or the second probe includes a first capture sequence; and b) a plurality of primers hybridized to a second target nucleic acid, where the plurality of primers are extended thereby generating one or more extension products hybridized to the second target nucleic acid.

Also provided herein are compositions including: a) an array including a first plurality of capture probes and a second plurality of capture probes, where a first capture probe of the first plurality of capture probes includes a first spatial barcode and a first capture domain and where a second capture probe of the second plurality of capture probes includes a second spatial barcode and a second capture domain; b) a ligation product hybridized to the first capture domain; and c) one or more extension products hybridized to the second capture domain.

In some embodiments, the composition includes an RNase H enzyme. In some embodiments, the composition includes a ligase.

In some embodiments, the first capture probe and/or the second capture probe include a cleavage domain, one or more functional domains, a unique molecular identifier, and combinations thereof.

All publications, patents, and patent applications mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

The term "substantially complementary" used herein means that a first sequence is at least 50%, 55%, 60%, 65%, 70%, 75%, 80%, 85%, 90%, 95%, 97%, 98% or 99% identical to the complement of a second sequence over a region of 2, 3, 4, 5, 6, 7, 8, 9, 10, 11, 12, 13, 14, 15, 16, 17, 18, 19, 20-40, 40-60, 60-100, or more nucleotides, or that the two sequences hybridize under stringent hybridization conditions. Substantially complementary also means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations known to those skilled in the art.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

FIG. 8A shows an exemplary sandwiching process where a first substrate including a biological sample and a second substrate are brought into proximity with one another and a liquid reagent drop is introduced on the second substrate in proximity to the capture probes.

FIG. 8B shows a fully formed sandwich configuration creating a chamber formed from one or more spacers, the first substrate, and the second substrate including spatially barcoded capture probes.

FIG. 10B is a schematic diagram showing capture and extension on an array of the ligation product shown in FIG. 10A and extension of the capture probe followed by release of the extended ligation product.

DETAILED DESCRIPTION

Figure 1:
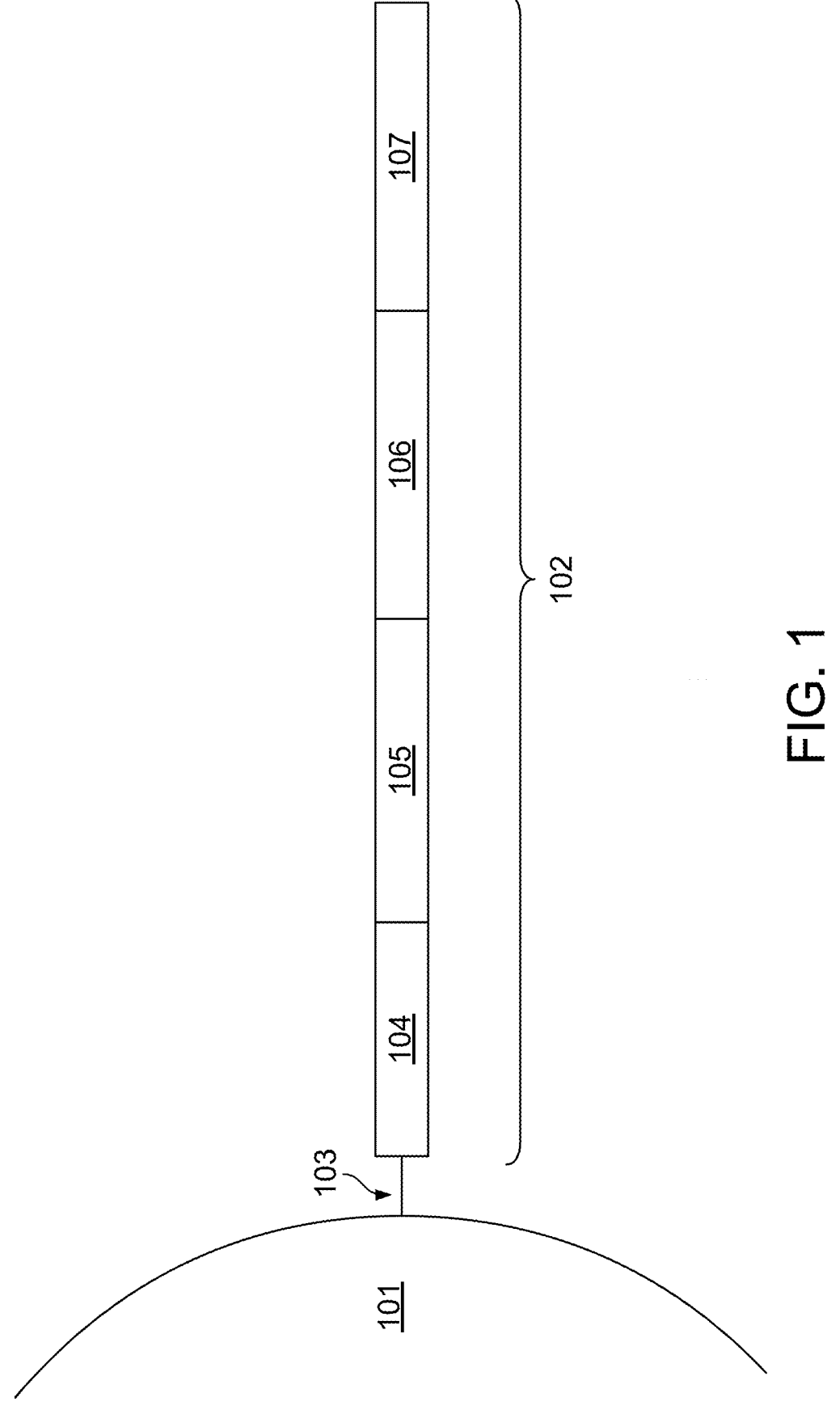
FIG. 1 is a schematic diagram showing an example of a barcoded capture probe, as described herein.

The present disclosure features methods of capturing analytes on a spatial array, where the spatial array includes a plurality of capture probes and a capture probe of the plurality of capture probes includes a spatial barcode and a capture domain. Sequences more than about 1 kilobase away from 3' end of nucleic acid analytes are generally not captured in nucleic acid sequencing libraries, however, some analytes, such as nucleic acid analytes encoding immune cell receptors (e.g., B cell receptors, T cell receptors) contain sequences of interest (e.g., VDJ sequences) more than 1 kilobase away from 3' end of the analyte. Since capture on a spatial array can be biased toward capture 3' end sequences of nucleic acid analytes (e.g., mRNA), methods are needed to capture 5' ends of the nucleic acid analytes, or complements thereof (e.g., a proxy of the analyte).

Analytes, such as mRNA, can be reverse transcribed by hybridizing to the target mRNA a primer that includes a sequence complementary to the target mRNA and a functional domain (e.g., a sequence domain for use in sequencing, a primer binding domain, etc.) to generate an RNA/DNA (e.g., RNA/cDNA) duplex. A polynucleotide sequence can be incorporated to the end of the cDNA. For example, a reverse transcriptase or a terminal transferase can add a polynucleotide sequence in a template-independent manner (e.g., at least three non-templated nucleotides). In some embodiments, the polynucleotide sequence is a heteropolynucleotide sequence (e.g., CGC). In some embodiments, the polynucleotide sequence is a homopolynucleotide sequence (e.g., CCC). In some embodiments, the polynucleotide sequence incorporated at the end of the cDNA is complementary to a capture domain of a capture probe. In some embodiments, the polynucleotide sequence incorporated at the end of the cDNA (e.g., a capture sequence) hybridizes to the capture domain of the capture probe. The target RNA can be removed (e.g., via digestion, denaturation, etc.) resulting in a single-stranded product that serves as a proxy of the target analyte which can be captured by a capture probe on a spatial array.

Spatial analysis methodologies and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 10,774,374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2013/171621, WO 2018/091676, WO 2020/176788, Rodriques et al., Science 363(6434):1463-1467, 2019; Lee et al., Nat. Protoc. 10(3): 442-458, 2015; Trejo et al., PLOS ONE 14(2): e0212031, 2019; Chen et al., Science 348(6233): aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10× Genomics Support Documentation website, and can be used herein in any combination, and each of which is incorporated herein by reference in their entireties. Further non-limiting aspects of spatial analysis methodologies and compositions are described herein.

Some general terminology that may be used in this disclosure can be found in Section (I)(b) of WO 2020/176788 and/or U.S. Patent Application Publication No. 2020/0277663. Typically, a "barcode" is a label, or identifier, which conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Examples of nucleic acid analytes include, but are not limited to, DNA (e.g., genomic DNA, cDNA) and RNA, including coding and non-coding RNA (e.g., mRNA, rRNA, tRNA, ncRNA). Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, a ligation product or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, the biological sample can be a tissue sample. In some embodiments, a biological sample can be a tissue section. In some embodiments, the biological sample (e.g., tissue sample) is a tissue microarray (TMA). A tissue microarray contains multiple representative tissue samples-which can be from different tissues or organisms-assembled on a single histologic slide. The TMA can therefore allow for high throughput analysis of multiple specimens at the same time. Tissue microarrays are paraffin blocks produced by extracting cylindrical tissue cores from different paraffin donor blocks and re-embedding these into a single recipient (microarray) block at defined array coordinates.

In some embodiments, a biological sample can be a fixed and/or stained biological sample (e.g., a fixed and/or stained tissue section). In some embodiments, the biological sample can be fixed using PAXgene. For example, the biological sample can be fixed using PAXgene in addition, or alternatively to, a fixative disclosed herein or known in the art (e.g., alcohol, acetone, acetone-alcohol, formalin, paraformaldehyde). PAXgene is a non-cross-linking mixture of different alcohols, acid and a soluble organic compound that preserves morphology and bio-molecules. It is a two-reagent fixative system in which tissue is firstly fixed in a solution containing methanol and acetic acid then stabilized in a solution containing ethanol. Sec, Ergin B. et al., J Proteome Res. 2010 Oct. 1;9(10):5188-96; Kap M. et al., PLOS One.; 6(11):e27704 (2011); and Mathieson W. et al., Am J Clin Pathol.; 146(1):25-40 (2016), each of which are hereby incorporated by reference in their entirety, for a description and evaluation of PAXgene for tissue fixation. Non-limiting examples of stains include histological stains (e.g., hematoxylin and/or cosin) and immunological stains (e.g., fluorescent stains). In some embodiments, a biological sample (e.g., a fixed and/or stained biological sample) can be imaged. Biological samples are also described in Section (I)(d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain). In some embodiments, a capture probe can include a cleavage domain and/or a functional domain (e.g., a primer-binding site, such as for next-generation sequencing (NGS)). See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

FIG. 1 is a schematic diagram showing an exemplary capture probe, as described herein. As shown, the capture probe 102 is optionally coupled to a feature 101 by a cleavage domain 103, such as a disulfide linker. The capture probe can include a functional sequence 104 that is useful for subsequent processing. The functional sequence 104 can include all or a part of sequencer specific flow cell attachment sequence (e.g., a P5 or P7 sequence), all or a part of a sequencing primer sequence, (e.g., a R1 primer binding site, a R2 primer binding site), or combinations thereof. The capture probe can also include a spatial barcode 105. The capture probe can also include a unique molecular identifier (UMI) sequence 106. While FIG. 1 shows the spatial barcode 105 as being located upstream (5') of UMI sequence 106, it is to be understood that capture probes wherein UMI sequence 106 is located upstream (5') of the spatial barcode 105 is also suitable for use in any of the methods described herein. The capture probe can also include a capture domain 107 to facilitate capture of a target analyte. In some embodiments, the capture probe comprises one or more additional functional sequences that can be located, for example between the spatial barcode 105 and the UMI sequence 106, between the UMI sequence 106 and the capture domain 107, or following the capture domain 107. The capture domain can have a sequence complementary to a sequence of a nucleic acid analyte. The capture domain can have a sequence complementary to an analyte capture sequence present in an analyte capture agent. The capture domain can have a sequence complementary to a splint oligonucleotide. Such splint oligonucleotide, in addition to having a sequence complementary to a capture domain of a capture probe, can have a sequence of a nucleic acid analyte, and/or an analyte capture sequence described herein.

The functional sequences can generally be selected for compatibility with any of a variety of different sequencing systems, e.g., Ion Torrent Proton or PGM, Illumina sequencing instruments, PacBio, Oxford Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, Illumina sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 105 and functional sequences 104 is common to all of the probes attached to a given feature (e.g., a bead, a well, a spot on an array). In some embodiments, the UMI sequence 106 of a capture probe attached to a given feature is different from the UMI sequence of a different capture probe attached to the given feature.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/or into or onto the biological sample.

In some cases, capture probes may be configured to prime, replicate, and consequently yield optionally barcoded extension products from a template (e.g., a DNA or RNA template, such as an analyte or an intermediate agent (e.g., an extension product, a ligation product or an analyte capture agent), or a portion thereof), or derivatives thereof (see, e.g., Section (II)(b) (vii) of WO 2020/176788 and/or U.S. Patent Application Publication No. 2020/0277663 regarding extended capture probes). In some cases, capture probes may be configured to form ligation products with a template (e.g., a DNA or RNA template, such as an analyte or an intermediate agent, or portion thereof), thereby creating ligations products that serve as proxies for a template.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes incorporating (e.g., adding) to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

As used herein, "an extension product" refers to an analyte, such as RNA (e.g., mRNA), that has been reverse transcribed (e.g., with a reverse transcriptase) to generate cDNA. In some embodiments, the cDNA is hybridized to the RNA (e.g., RNA/cDNA duplex). In some embodiments, the cDNA is hybridized to the mRNA. In some embodiments, the extension product is further extended by incorporating (e.g., adding) a polynucleotide sequence (e.g., a heteropolynucleotide sequence, a homopolynucleotide sequence) to the 3' end of the extension product (e.g., cDNA). For example, a reverse transcriptase or a terminal transferase can add at least three nucleotides (e.g., a polynucleotide sequence) to the 3' end of the extension product in a template-independent manner. In some embodiments, the polynucleotide sequence added to the 3' end of the extension product is complementary to a capture domain of a capture probe. In some embodiments, the polynucleotide sequence (e.g., a heteropolynucleotide sequence, a homopolynucleotide sequence) hybridizes to the capture domain of the capture probe. In some embodiments, the RNA (e.g., mRNA) is removed (e.g., by digestion) from the extension product. In such embodiments, the term extension product also refers to a single-stranded DNA (e.g., cDNA) product that includes a complement of the target nucleic acid (e.g., RNA, mRNA).

As used herein, "an extended capture product" refers to an extension product that has been captured on a spatial array and extended using the capture probe as a template. For example, an extension product, as described herein, after capture by a capture probe can be extended to include a capture sequence, or a complement thereof, that is capable of hybridizing to a capture domain of a capture probe. In some embodiments, when the extension product hybridizes to the capture domain of the capture probe, an end of the extension product (e.g., a 3' end) can be extended to generate the extended capture product. In such examples, the extended capture product includes the domains (e.g., a UMI, a spatial barcode, one or more functional domains, or combination thereof etc.) present in the capture probe on the spatial array. In some embodiments, the extended capture product is released from the capture probe and collected for downstream applications, such as amplification and sequencing.

Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe such as an extended capture product), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder. Exemplary methods for identifying spatial information of biological and/or medical importance can be found in U.S. Patent Application Publication No. 2021/0140982A1, U.S. Patent Application No. 2021/0198741A1, and/or U.S. Patent Application No. 2021/0199660.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in Section (II)(c) of WO 2020/176788 and/or U.S. Patent Application Publication No. 2020/0277663. Exemplary features and geometric attributes of an array can be found in Sections (II)(d)(i), (II)(d)(iii), and (II)(d)(iv) of WO 2020/176788 and/or U.S. Patent Application Publication No. 2020/0277663.

Generally, analytes and/or intermediate agents (or portions thereof), such as an extension product, can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(c) of WO 2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Suitable systems for performing spatial analysis can include components such as a chamber (e.g., a flow cell or scalable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in WO 2021/102003 and/or U.S. patent application Ser. No. 16/951,854, each of which is incorporated herein by reference in their entireties.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2021/102039 and/or U.S. patent application Ser. No. 16/951, 864, each of which is incorporated herein by reference in their entireties.

In some cases, a map of analyte presence and/or level can be aligned to an image of a biological sample using one or more fiducial markers, e.g., objects placed in the field of view of an imaging system which appear in the image produced, as described in the Substrate Attributes Section, Control Slide for Imaging Section of WO 2020/123320, WO 2021/102005, and/or U.S. patent application Ser. No. 16/951,843, each of which is incorporated herein by reference in their entireties. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

5' Capture of Target Nucleic Acids

The present disclosure features methods of capturing analytes on a spatial array, where the spatial array includes a plurality of capture probes and a capture probe of the plurality of capture probes includes a spatial barcode and a capture domain. In some embodiments, the analyte is a target nucleic acid. Since capture on a spatial array can generally be biased toward capture of 3' end of nucleic acid analytes, methods are needed to determine the sequence of 5' end of nucleic acid analytes (e.g., by capturing 5' end of the nucleic acid analyte), or a complement thereof (e.g., a proxy of the analyte). For example, target nucleic acid analytes (e.g., RNA) can be reverse transcribed with a primer including a sequence complementary to the target nucleic acid and a functional domain, such as a primer binding site or a sequencing specific site to generate an RNA/DNA (e.g., cDNA) duplex. An enzyme such as a reverse transcriptase or terminal transferase can add or incorporate non-templated nucleotides to the 3' end of the cDNA. For example, a reverse transcriptase or terminal transferase enzyme can add at least 3 nucleotides (e.g., a polynucleotide sequence (e.g., a heteropolynucleotide sequence (e.g., CGC), a homopolynucleotide sequence (e.g., CCC))) to the 3' end of the cDNA. In some embodiments, the polynucleotide sequence added to the end of the cDNA is complementary to a capture domain of a capture probe. In some embodiments, the polynucleotide sequence added to the end of the cDNA (e.g., a capture sequence) hybridizes to the capture domain of the capture probe. The target nucleic acid can be removed (e.g., digested, denatured, etc.) resulting in a single-stranded DNA product. The single-stranded DNA product can include the functional domain at its 5' end, a copy of the target analyte (e.g., cDNA), and the polynucleotide sequence at its 3' end that is capable of binding (e.g., hybridizing) to a capture domain of a capture probe on the array.

Alternatively, a second primer can hybridize to the polynucleotide sequence added to the 3' end of the cDNA (e.g., extension product). The second primer can function as an extension template to further extend the extension product (e.g., a template switching oligonucleotide (TSO)). In some embodiments, the second primer includes a second capture sequence and a complement of the second capture sequence is incorporated into the extension product. In some embodiments, the second primer includes RNA. The single-stranded DNA product can include the functional domain at its 5' end, a copy of the target analyte (e.g., cDNA), and a complement of the capture sequence that is capable of binding (e.g., hybridizing) to a capture domain of a capture probe on the array at its 3' end.

In preferred embodiments of the methods of the disclosure, the extension reaction (e.g., reverse transcription) is performed in situ. For example, the biological sample containing the target nucleic acid is contacted with the primer or plurality of primers, such that the extension product(s) (e.g., cDNA) is generated in the biological sample.

In some embodiments, the capture domain includes a fixed sequence. As used herein, a "fixed sequence" is a non-random sequence. A "fixed sequence" can be complementary to the complement of the capture sequence that is incorporated into the extension product(s) described herein. For example, the capture domain (e.g., the fixed sequence therein) can be complementary to the non-templated polynucleotide sequence added to the extension product(s). In some embodiments, the plurality of capture probes on an array includes the same fixed sequence. The methods described herein can use different capture sequences which are incorporated (e.g., a complement thereof) into the extension product(s). For example, it is only necessary for the complement of the capture sequence (e.g., the polynucleotide sequence added to the extension products) in the extension products and the capture domain to be substantially complementary to each other, such that the capture domain including a fixed sequence can hybridize to and/or capture the extension product(s).

Target nucleic acids can include a nucleic acid molecule with a nucleic acid sequence encoding at least a portion of a V-J sequence or a V(D)J sequence of an immune cell receptor (e.g., a T cell receptor or a B cell receptor). Target nucleic acids can include a nucleic acid molecule with a nucleic acid sequence encoding an antibody. In some embodiments, the target nucleic acid is RNA. In some embodiments, the RNA is mRNA. In some embodiments, the target nucleic acids are nucleic acids encoding immune cell receptors. In some embodiments, target nucleic acids encoding immune cell receptors identify clonotype populations from a biological sample. In some embodiments, target nucleic acids include a constant region, such as a sequence encoding a constant region of an immune cell receptor (e.g., an antibody). In some embodiments, target nucleic acids include a variable region, such as a sequence encoding a variable region of an immune cell receptor (e.g., antibody), for example, a sequence encoding CDR1, CD2, and/or CDR3 of an immune cell receptor.

In some embodiments, the target nucleic acid encodes an immune cell receptor. In some embodiments, the immune cell receptor is a B cell receptor. In some embodiments, the B cell receptor includes an immunoglobulin kappa light chain. In some embodiments, the target nucleic acid includes a sequence encoding a CDR3 region of the immunoglobulin kappa light chain. In some embodiments, the target nucleic acid includes a sequence encoding one or both of CDR1 and CDR2 of the immunoglobulin kappa light chain. In some embodiments, the target nucleic acid includes a sequence encoding a full-length variable domain of the immunoglobulin kappa light chain. In some embodiments, the mRNA includes a sequence that does not encode a B cell receptor or a fragment thereof or a T cell receptor or a fragment thereof.

In some embodiments, the B cell receptor includes an immunoglobulin lambda light chain. In some embodiments, the target nucleic acid includes a sequence encoding a CDR3 of the immunoglobulin lambda light chain. In some embodiments, the target nucleic acid includes a sequence encoding one or both of CDR1 and CDR2 of the immunoglobulin lambda light chain. In some embodiments, the target nucleic acid includes a sequence encoding a full-length variable domain of the immunoglobulin lambda light chain.

In some embodiments, the B cell receptor includes an immunoglobulin heavy chain. In some embodiments, the target nucleic acid includes a sequence encoding a CDR3 of the immunoglobulin heavy chain. In some embodiments, the target nucleic acid includes a sequence encoding one or both of CDR1 and CDR2 of the immunoglobulin heavy chain. In some embodiments, the target nucleic acid includes a sequence encoding a full-length variable domain of the immunoglobulin heavy chain.

In some embodiments, the immune cell receptor is a T cell receptor. In some embodiments, the T cell receptor includes a T cell receptor alpha chain. In some embodiments, the target nucleic acid includes a sequence encoding a CDR3 of the T cell receptor alpha chain. In some embodiments, the target nucleic acid includes a sequence encoding one or both of CDR1 and CDR2 of the T cell receptor alpha chain. In some embodiments, the target nucleic acid includes a sequence encoding a full-length variable domain of the T cell receptor alpha chain.

In some embodiments, the T cell receptor includes a T cell receptor beta chain. In some embodiments, the target nucleic acid includes a sequence encoding a CDR3 of the T cell receptor beta chain. In some embodiments, the target nucleic acid includes one or both of CDR1 and CDR2 of the T cell receptor beta chain. In some embodiments, the target nucleic acid further includes a full-length variable domain of the T cell receptor beta chain.

While useful for analysis of immune cell receptor analytes such as nucleic acids encoding immune cell receptors, the disclosed methods are not limited thereto. Thus, the disclosed methods can be useful for analysis of a nucleotide sequence at and/or proximal to the 5' end of any target nucleic acid, such as, genomic DNA, lncRNA, and the like.

In some embodiments, the methods included herein include determining the complementarity determining regions (CDRs) of a T cell receptor or a fragment thereof, and/or a B cell receptor or a fragment thereof (e.g., an antibody or fragment thereof).

Provided herein are methods for determining a location of a first target nucleic acid and a second target nucleic acid in a biological sample, the method including: (a) contacting the biological sample with: (i) a first probe and a second probe, where the first probe and the second probe each include sequences that are substantially complementary to sequences of the first target nucleic acid, and where the second probe includes a first capture sequence that is complementary to all or a portion of a first capture domain; and (ii) a first primer including a sequence that hybridizes to a complementary sequence in the second target nucleic acid, and a functional domain; (b) hybridizing the first probe and the second probe to the first target nucleic acid; (c) generating a ligation product by ligating the first probe to the second probe; (d) hybridizing the first capture sequence of the ligation product to the first capture domain on an array, where the array includes a first plurality of capture probes, where a first capture probe of the first plurality of capture probes includes: a first spatial barcode and the first capture domain; (e) hybridizing the first primer to the second target nucleic acid and extending the first primer using the second target nucleic acid as a template to generate an extension product; (f) incorporating a polynucleotide sequence including at least three nucleotides to the 3' end of the extension product; (g) hybridizing a second primer to the polynucleotide sequence of the extension product of step (f), where the second primer includes a second capture sequence; (h) extending the extension product of step (g) using the second primer as a template, thereby incorporating a complement of the second capture sequence into the extension product; (i) hybridizing the complement of the second capture sequence of the extension product of (h) to a second capture domain on the array, where the array includes a second plurality of capture probes, where a second capture probe of the second plurality of capture probes includes: a second spatial barcode and the second capture domain; (j) determining (i) the sequence of the first spatial barcode, or a complement thereof, and (ii) all or a portion of the sequence of the ligation product hybridized to the first capture domain, or a complement thereof, and using the determined sequences of (i) and (ii) to determine the location of the first target nucleic acid in the biological sample; and (k) determining (iii) the sequence of the second spatial barcode, or a complement thereof, and (iv) all or a portion of the sequence of the extension product corresponding to a sequence of the second target nucleic acid, or a complement thereof, and using the determined sequences of (iii) and (iv) to determine the location of the second target nucleic acid in the biological sample.

In some embodiments, the biological sample is disposed on the array including the first plurality and the second plurality of capture probes.

In some embodiments, the biological sample is disposed on the array including the first plurality and the second plurality of capture probes. In some embodiments, the biological sample is disposed on a first substrate, and where the array including the first and second plurality of capture probes is disposed on a second substrate. In some embodiments, the method includes aligning the first substrate with the second substrate, such that at least a portion of the biological sample is aligned with at least a portion of the second substrate.

In some embodiments, the hybridizing in steps (d) and/or (i) include passive migration of the ligation product and/or the extension product from the biological sample to the array. In some embodiments, the hybridizing in steps (d) and/or (i) include active migration of the ligation product and/or the extension product from the biological sample to the array, and optionally, where the active migration includes electrophoresis.

In some embodiments, the polynucleotide sequence in step (f) includes a homopolynucleotide sequence (e.g., CCC). In some embodiments, the polynucleotide sequence in step (f) includes a heteropolynucleotide sequence (e.g., CGC).

In some embodiments, the first capture domain includes a first fixed sequence. In some embodiments, the second capture domain includes a second fixed sequence. In some embodiments, the first capture domain and the second capture domain have the same sequence. In some embodiments, the first capture domain and the second capture domain have a different sequence.

In some embodiments, the first primer includes a random sequence. In some embodiments, the random sequence includes a random hexamer. In some embodiments, the random sequence includes a random decamer. In some embodiments, the first primer includes a homopolymer sequence. In some embodiments, the homopolymer sequence includes a poly(T) sequence. In some embodiments, the first primer includes a sequence substantially complementary to a nucleic acid sequence encoding a constant region of an antibody (e.g., the second target nucleic acid). In some embodiments, the first primer includes a sequence substantially complementary to a nucleic acid sequence encoding a constant region of a B cell receptor (e.g., the second target nucleic acid). In some embodiments, the first primer includes a sequence substantially complementary to a nucleic acid sequence encoding a constant region of a T cell receptor (e.g., the second target nucleic acid).

In some embodiments, the functional domain includes a primer binding site or a sequencing specific site.

In some embodiments, the method includes removing the first target nucleic acid, or any other nucleic acid hybridized to the ligation product, before the first capture sequence of the second probe hybridizes to the first capture domain of the first capture probe. In some embodiments, the method includes removing the second target nucleic acid, or any other nucleic acid hybridized to the extension product(s) (e.g., extended cDNA product) before the sequence added to the extension product via a second primer including a sequence complementary to the added polynucleotide sequence and a second capture sequence that hybridizes to the second capture domain of the second capture probe. In some embodiments, the removing includes the use of an RNase. In some embodiments, the RNase is RNase A.

In some embodiments, the RNase is RNase P. In some embodiments, the RNase is RNase T1. In some embodiments, the RNase is RNase H. In some embodiments, the removing includes heat.

In some embodiments, the extension product(s) (e.g., the single-stranded extension product(s)) hybridizes to the capture domain of the second capture probe on the substrate. In some embodiments, 3' end of the second capture probe is extended using the extension product as a template. In some examples, 3' end of the extension product (e.g., single-stranded cDNA product) is extended using the second capture probe as a template, thereby generating an extended capture product. In some embodiments, both the second capture probe, and the extension products hybridized thereto, are extended from their 3' ends.

In some embodiments, the ligation product (e.g., the single-stranded ligation product(s)) hybridize to the capture domain of the first capture probe on the substrate. In some embodiments, 3' end of the first capture probe is extended using the ligation product as a template. In some embodiments, 3' end of the ligation product is extended using the first capture probe as a template, thereby generating an extended ligation product. In some embodiments, both the first capture probe, and the extension products hybridized thereto, are extended from their 3' ends.

In some embodiments, step (e) is performed after step (c). In some embodiments, step (e) is performed before step (c).

Also provided herein are methods for determining a location of a first target nucleic acid and a second target nucleic acid in a biological sample, the method including: (a) contacting the biological sample with: (i) a first probe and a second probe, where the first probe and the second probe each include sequences that are substantially complementary to sequences of the first target nucleic acid, and where the second probe includes a first capture sequence that is complementary to all or a portion of a first capture domain; and (ii) a primer including a sequence that hybridizes to a complementary sequence in the second target nucleic acid and a functional domain; (b) hybridizing the first probe and the second probe to the first target nucleic acid; (c) generating a ligation product by ligating the first probe to the second probe; (d) hybridizing the first capture sequence of the ligation product to the first capture domain on the array, where the array includes a first plurality of capture probes, where a first capture probe of the first plurality of capture probes includes: a first spatial barcode and the first capture domain; (e) hybridizing the primer to the second target nucleic acid and extending the primer using the second target nucleic acid as a template to generate an extension product; (f) incorporating a polynucleotide sequence including at least three nucleotides to the 3' end of the extension product; (g) hybridizing the polynucleotide sequence of the extension product to a second capture domain on an array, where the array includes a second plurality of capture probes, where a second capture probe of the second plurality of capture probes includes: a second spatial barcode and the second capture domain; (h) determining (i) the sequence of the first spatial barcode, or a complement thereof, and (ii) all or a portion of the sequence of the ligation product hybridized to the first capture domain, or a complement thereof, and using the determined sequences of (i) and (ii) to determine the location of the first target nucleic acid in the biological sample; and (i) determining (iii) the sequence of the second spatial barcode, or a complement thereof, and (iv) all or a portion of the sequence of the extension product corresponding to a sequence of the second target nucleic acid, or a complement thereof, and using the determined sequences of (iii) and (iv) to determine the location of the second target nucleic acid in the biological sample.

In some embodiments, the biological sample is disposed on the array including the first and the second plurality of capture probes. In some embodiments, the biological sample is disposed on a first substrate, and where the array including the first and second plurality of capture probes is disposed on a second substrate. In some embodiments, the method includes aligning the first substrate with the second substrate, such that at least a portion of the biological sample is aligned with at least a portion of the second substrate.

In some embodiments, the hybridizing in steps (d) and (g) include passive migration of the ligation product and/or extension product from the biological sample to the array. In some embodiments, the hybridizing in steps (d) and (g) include active migration of the ligation product and/or the extension product from the biological sample to the array, and optionally, where the active migration includes electrophoresis.

In some embodiments, the polynucleotide sequence in step (f) includes a homopolynucleotide sequence (e.g., CCC). In some embodiments, the polynucleotide sequence in step (f) includes a heteropolynucleotide sequence (e.g., CGC).

In some embodiments, the first capture domain includes a fixed sequence, e.g., poly(T). In some embodiments, the second capture domain includes a fixed sequence. In some embodiments, the first capture domain and the second capture domain have the same sequence, e.g., poly(T). In some embodiments, the first capture domain and the second capture domain have a different sequence. In some embodiments, the primer includes a random sequence. In some embodiments, the random sequence includes a random hexamer. In some embodiments, the random sequence includes a random decamer. In some embodiments, the primer includes a homopolymer sequence. In some embodiments, the homopolymer sequence includes a poly(T) sequence. In some embodiments, the primer includes a sequence substantially complementary to a nucleic acid sequence encoding an antibody (e.g., a second target nucleic acid). In some embodiments, first primer includes a sequence substantially complementary to a nucleic acid sequence encoding a constant region of a B cell receptor (e.g., a second target nucleic acid). In some embodiments, the first primer includes a sequence substantially complementary to a nucleic acid sequence encoding a constant region of a T cell receptor (e.g., a second target nucleic acid).

In some embodiments, the functional domain includes a primer binding site or a sequencing specific site.

In some embodiments, the extending in step (e) includes the use of a reverse transcriptase.

In some embodiments, incorporating the polynucleotide sequence to the 3' end of the extension product in step (f) includes the use of a terminal deoxynucleotidyl transferase. In some embodiments, incorporating the polynucleotide sequence to the 3' end of the extension product in step (f) includes the use of a reverse transcriptase.

In some embodiments, the method further includes removing the first target nucleic acid, or any other nucleic acid hybridized to the ligation product, before the first capture sequence hybridizes to the first capture domain of the first capture probe; and/or removing the second target nucleic acid, or any other nucleic acid hybridized to the extension product, before the polynucleotide sequence hybridizes to the second capture domain of the second capture probe. In some embodiments, the method includes removing the first target nucleic acid, or any other nucleic acid hybridized to the ligation product, before the first capture sequence of the second probe hybridizes to the first capture domain of the first capture probe. In some embodiments, the method includes removing the second target nucleic acid, or any other nucleic acid hybridized to the extension product(s) (e.g., extended cDNA product) before the sequence added to the extension product (e.g., a homopolynucleotide sequence, a heteropolynucleotide sequence). In some embodiments, the removing includes the use of an RNase. In some embodiments, the RNase is RNase A. In some embodiments, the RNase is RNase P. In some embodiments, the RNase is RNase T1. In some embodiments, the RNase is RNase H. In some embodiments, the removing includes use of heat.

In some embodiments, the extension product(s) (e.g., the single-stranded extension product(s)) hybridizes to the capture domain of the second capture probe on the substrate. In some embodiments, 3' end of the second capture probe is extended using the extension product as a template. In some examples, 3' end of the extension product (e.g., single-stranded cDNA product) is extended using the second capture probe as a template, thereby generating an extended capture product. In some embodiments, both the second capture probe, and the extension capture products hybridized thereto, are extended from their 3' ends.

In some embodiments, the ligation product (e.g., the single-stranded ligation product(s)) hybridizes to the capture domain of the first capture probe on the substrate. In some embodiments, 3' end of the first capture probe is extended using the ligation product as a template. In some embodiments, 3' end of the ligation product is extended using the first capture probe as a template, thereby generating an extended ligation product. In some embodiments, both the first capture probe, and the extension products hybridized thereto, are extended from their 3' ends.

In some embodiments, step (e) is performed after step (c). In some embodiments, step (e) is performed before step (c).

Plurality of Primers

The methods described herein can also use a plurality of primers. For example, the plurality of primers can hybridize to a target nucleic acid at different locations in the target nucleic acid and subsequently be extended in combination with the RNA-templated ligation steps also described herein. Extending the plurality of primers generates one or more extension products that include a polynucleotide sequence that can be complementary to a capture domain of a capture probe.

In embodiments where a plurality of primers is used, the plurality of primers can hybridize to different sequences in the target nucleic acid. For example, the plurality of primers can hybridize to adjacent sequences (e.g., "tiling") on the target nucleic acid. Adjacent sequences can be, but are not necessarily, contiguous. In some embodiments, adjacent sequences can be within 1-10 nucleotides of each other. In some embodiments, the plurality of primers hybridize to non-adjacent sequences on the target nucleic acid. In some embodiments, two or more primers of the plurality of primers hybridize to two or more different sequences in the target nucleic acid. In some embodiments, ten or more primers of the plurality of primers hybridize to ten or more different sequences in the target nucleic acid. In some embodiments, fifty or more primers of the plurality of primers hybridize to fifty or more different sequences in the target nucleic acid. In some embodiments, one hundred or more primers of the plurality of primers hybridize to one hundred or more different sequences in the target nucleic acid. In some embodiments, a plurality of extension products can be generated by extension of the plurality of primers. The resulting extension products can have differing lengths depending on the exact location in the target nucleic acid from which they were primed. Thus, in some embodiments, extension products (e.g., cDNAs) of different lengths and/or sequences can be generated from the same target nucleic acid (e.g., mRNA). See, e.g., FIG. 6.

In some embodiments, the primer includes a sequence that is complementary to a sequence in a target nucleic acid.

The sequence complementary to the target nucleic acid can be a gene specific sequence, which, for example, may allow for selective capture of a desired target nucleic acid. In some embodiments, the primer includes a homopolymer sequence and a functional domain. In some embodiments, the homopolymer sequence is a poly(T) sequence. In some embodiments, the primer includes a random sequence and a functional domain. In some embodiments, the random sequence includes 5, 6, 7, 8, 9, 10, 11, 12, 13, 14, 15, 16, 17, 18, 19, 20, or more random nucleotides. In some embodiments, the random sequence is a random hexamer. In some embodiments, the random sequence is a random decamer. In some embodiments, the functional domain is a primer binding site. In some embodiments, the functional domain is a sequencing specific site.

In some embodiments, the method includes generating two or more extension products from the primer of the plurality of primers. For example, a single primer can facilitate reverse transcription for more than a single extension reaction resulting in 2, 3, 4, 5, 6, 7, 8, 9, 10, 20, 30, 40, 50, 100, 200, 300, 400, 500, 600, 700, 800, 900, 1000, or more extension products produced from a single primer. In some embodiments, the two or more extension products generated from the same primer include the same sequence and/or length.

In some embodiments, the plurality of primers includes multiple unique primers, where each unique primer includes a unique sequence. The plurality of primers may include multiple copies (e.g., 2, 10, 20, 50, 100, 1000, 10000 or more) of each unique primer. In some embodiments, each unique primer in the plurality of primers hybridizes to a distinct sequence within the target nucleic acid. Thus, in some embodiments, the one or more extension products include different sequences and/or lengths. For example, when a plurality of primers is hybridized to a target nucleic acid and extended, the one or more extension products can have varying sequences and/or lengths.

In embodiments where the target nucleic acid includes a sequence that encodes an immune cell receptor, the plurality of primers preferably hybridize to a region of the target nucleic acid that encodes a constant region of the immune cell receptor.

In some embodiments, the extension product(s) that hybridize to the capture domains of the plurality of capture probes can migrate (e.g., diffuse) towards the capture probes through passive migration such as gravity. In some embodiments, the extension product(s) that hybridize to the capture domains of the plurality of capture probes can migrate toward the capture probes through active migration. In some embodiments, the active migration includes electrophoresis.

In some embodiments, the array includes one or more features (e.g., any of the features described herein). In some embodiments, the one or more features includes a bead.

As described herein, a capture probe refers to any molecule capable of capturing (directly or indirectly) and/or labelling an analyte (e.g., an analyte of interest, such as a nucleic acid) in a biological sample. In some embodiments, the capture probe is a nucleic acid. In some embodiments, the capture probe is DNA. In some embodiments, the capture probe includes a barcode (e.g., a spatial barcode) and/or a unique molecular identifier (UMI)) and a capture domain. In some embodiments, a capture probe can include a cleavage domain and/or one or more functional domains (e.g., a primer-binding site or a sequencing specific site, such as for next-generation sequencing (NGS)).

Thus provided herein are methods for determining a location of a first target nucleic acid and a second target nucleic acid in a biological sample, the method including: (a) contacting the biological sample with: (i) a first probe and a second probe, where the first probe and the second probe each include sequences that are substantially complementary to sequences of the first target nucleic acid, and where the second probe includes a first capture sequence that is complementary to all or a portion of a first capture domain; and (ii) a plurality of primers, where the plurality of primers includes nucleic acid sequences that hybridize to complementary sequences in the second target nucleic acid and a functional domain; (b) hybridizing the first probe and the second probe to the first target nucleic acid; (c) generating a ligation product by ligating the first probe to the second probe; (d) hybridizing the first capture sequence of the ligation product to a first capture domain on an array, where the array includes a first plurality of capture probes, where a first capture probe of the plurality of first capture probes includes: a first spatial barcode and the first capture domain; (c) hybridizing one or more of the plurality of primers to the second target nucleic acid and extending the one or more of the plurality of primers using the second target nucleic acid as a template to generate one or more extension products; (f) incorporating a polynucleotide sequence including at least three nucleotides to the 3' end of the one or more extension products; (g) hybridizing a second primer to the polynucleotide sequence of the one or more extension products of step (f), where the second primer includes a second capture sequence; (h) extending the one or more extension products of step (g) using the second primer as a template, thereby incorporating a complement of the second capture sequence into the one or more extension products; (i) hybridizing the complement of the second capture sequence of the one or more extension products of (h) to a second capture domain on the array, where the array includes a second plurality of capture probes, where a second capture probe of the second plurality of capture probes includes: a second spatial barcode and the second capture domain; (j) determining (i) the sequence of the first spatial barcode, or a complement thereof, and (ii) all or a portion of the sequence of the ligation product hybridized to the first capture domain, or a complement thereof, and using the determined sequences of (i) and (ii) to determine the location of the first target nucleic acid in the biological sample; and for an extension product in the one or more extension products (k) determining (iii) the sequence of the second spatial barcode, or a complement thereof, and (iv) all or a portion of the sequence of one of the one or more extension products corresponding to a sequence of the second target nucleic acid, or a complement thereof, and using the determined sequences of (iii) and (iv) to determine the location of the second target nucleic acid in the biological sample.

In some embodiments, the biological sample is disposed on the array including the first plurality and the second plurality of capture probes. In some embodiments, the biological sample is disposed on a first substrate, and where the array including the first and second plurality of capture probes is disposed on a second substrate. In some embodiments, the method includes aligning the first substrate with the second substrate, such that at least a portion of the biological sample is aligned with at least a portion of the second substrate.

In some embodiments, the hybridizing in steps (d) and/or (i) include passive migration of the ligation product and/or the one or more extension products from the biological sample to the array. In some embodiments, the hybridizing in steps (d) and/or (i) include active migration of the ligation product and/or the one or more extension products from the biological sample to the array, and optionally, where the active migration includes electrophoresis.

In some embodiments, incorporating the polynucleotide sequence in step (f) includes a homopolynucleotide sequence (e.g., CCC). In some embodiments, incorporating the polynucleotide sequence in step (f) includes a heteropolynucleotide sequence (e.g., CGC).

In some embodiments, the first capture domain includes a fixed sequence. In some embodiments, the second capture domain includes a fixed sequence. In some embodiments, the first capture domain and the second capture domain have the same sequence. In some embodiments, the first capture domain and the second capture domain have a different sequence. In some embodiments, the primer includes a random sequence. In some embodiments, the random sequence includes a random hexamer. In some embodiments, the random sequence includes a random decamer. In some embodiments, the primer includes a homopolymer sequence. In some embodiments, the homopolymer sequence includes a poly(T) sequence. In some embodiments, the primer includes a sequence substantially complementary to a nucleic acid sequence encoding an antibody (e.g., a second target nucleic acid). In some embodiments, first primer includes a sequence substantially complementary to a nucleic acid sequence encoding a constant region of a B cell receptor (e.g., a second target nucleic acid). In some embodiments, the first primer includes a sequence substantially complementary to a nucleic acid sequence encoding a constant region of a T cell receptor (e.g., a second target nucleic acid).

In some embodiments, the functional domain includes a primer binding site or a sequencing specific site.

In some embodiments, incorporating the polynucleotide sequence to the 3' end of the extension product in step (f) includes the use of a terminal deoxynucleotidyl transferase. In some embodiments, incorporating the polynucleotide sequence to the 3' end of the extension product in step (f) includes the use of a reverse transcriptase.

In some embodiments, the second primer includes RNA.

In some embodiments, the method includes removing the second target nucleic acid, or any other nucleic acid hybridized, to the one or more extension products before the second capture sequence of the second primer hybridizes to the second capture domain of the second capture probe.

In some embodiments, the method includes removing the first target nucleic acid, or any other nucleic acid hybridized to the ligation product, before the first capture sequence of the second probe hybridizes to the first capture domain of the first capture probe. In some embodiments, the removing includes the use of an RNase. In some embodiments, the RNase is RNase A. In some embodiments, the RNase is RNase P. In some embodiments, the RNase is RNase T1. In some embodiments, the RNase is RNase H. In some embodiments, the removing includes heat.

In some embodiments, the method includes a step of extending 3' end of the one or more extensions product of step (g) using the second capture probe as a template, thereby generating an extended capture product; and/or extending 3' end of the ligation product using the first capture probe as a template, thereby generating an extended ligation product.

In some embodiments, the extended capture product is removed from the second capture probe; and/or the extended ligation product is removed from the first capture probe.

In some embodiments, the removing includes the use of an RNase. In some embodiments, the RNase is RNase A. In some embodiments, the RNase is RNase P. In some embodiments, the RNase is RNase T1. In some embodiments, the RNase is RNase H. In some embodiments, the removing includes heat.

In some embodiments, the extension product(s) (e.g., the single-stranded extension product(s)) hybridizes to the capture domain of the second capture probe on the substrate. In some embodiments, 3' end of the second capture probe is extended using the extension product as a template. In some examples, 3' end of the extension product (e.g., single-stranded cDNA product) is extended using the second capture probe as a template, thereby generating an extended capture product. In some embodiments, both the second capture probe, and the extension products hybridized thereto, are extended from their 3' ends.

In some embodiments, the ligation product (e.g., the single-stranded ligation product(s)) hybridizes to the capture domain of the first capture probe on the substrate. In some embodiments, 3' end of the first capture probe is extended using the ligation product as a template. In some embodiments, 3' end of the ligation product is extended using the first capture probe as a template, thereby generating an extended ligation product. In some embodiments, both the first capture probe, and the extension products hybridized thereto, are extended from their 3' ends.

In some embodiments, step (e) is performed after step (c). In some embodiments, step (e) is performed before step (c).

Also provided herein are method for determining a location of a first target nucleic acid and a second target nucleic acid in a biological sample, the method including: (a) contacting the biological sample with: (i) a first probe and a second probe, where the first probe and the second probe each include sequences that are substantially complementary to sequences of the first target nucleic acid, and where the second probe includes a first capture sequence that is complementary to all or a portion of a first capture domain; and (ii) a plurality of primers, where the plurality of primers include nucleic acid sequences that hybridize to complementary sequences in the second target nucleic acid and a functional domain; (b) hybridizing the first probe and the second probe to the first target nucleic acid; (c) generating a ligation product by ligating the first probe to the second probe; (d) hybridizing the ligation product to the first capture domain of the first capture probe; (e) hybridizing one or more of the plurality of primers to the second target nucleic acid and extending the one or more of the plurality of primers using the second target nucleic acid as a template to generate one or more extension products; (f) incorporating a polynucleotide sequence including at least three nucleotides to the 3' end of the one or more extension products; (g) hybridizing the polynucleotide sequence of the one or more extension products to the second capture domain of the second capture probe; (h) determining (i) the sequence of the first spatial barcode, or a complement thereof, and (ii) all or a portion of the sequence of the ligation product hybridized to the first capture domain, or a complement thereof, and using the determined sequences of (i) and (ii) to determine the location of the first target nucleic acid in the biological sample; and for an extension product in the one or more extension products (i) determining (iii) the sequence of the second spatial barcode, or a complement thereof, and (iv) all or a portion of the sequence of one of the one or more extension products corresponding to a sequence of the second target nucleic acid, or a complement thereof, and using the determined sequences of (iii) and (iv) to determine the location of the second target nucleic acid in the biological sample.

In some embodiments, the biological sample is disposed on the array including the first plurality and the second plurality of capture probes. In some embodiments, the biological sample is disposed on a first substrate, and where the array including the first and second plurality of capture probes is disposed on a second substrate. In some embodiments, the method includes aligning the first substrate with the second substrate, such that at least a portion of the biological sample is aligned with at least a portion of the second substrate.

In some embodiments, the hybridizing in steps (d) and/or (g) include passive migration of the ligation product and/or the one or more extension products from the biological sample to the array. In some embodiments, the hybridizing in steps (d) and/or (g) include active migration of the ligation product and/or the one or more extension products from the biological sample to the array, and optionally, where the active migration includes electrophoresis.

In some embodiments, incorporating the polynucleotide sequence in step (f) includes a homopolynucleotide sequence (e.g., CCC). In some embodiments, incorporating the polynucleotide sequence in step (f) includes a heteropolynucleotide sequence (e.g., CGC).

In some embodiments, the first capture domain includes a first fixed sequence. In some embodiments, the second capture domain includes a second fixed sequence. In some embodiments, the first capture domain and the second capture domain have the same sequence. In some embodiments, the first capture domain and the second capture domain have different sequences.

In some embodiments, the plurality of primers includes a random sequence. In some embodiments, the random sequence includes a random hexamer. In some embodiments, the random sequence includes a random decamer. In some embodiments, the plurality of primers includes a homopolymer sequence. In some embodiments, the homopolymer sequence includes a poly(T) sequence. In some embodiments, the plurality of primers includes a sequence substantially complementary to a nucleic acid sequence encoding an antibody (e.g., a second target nucleic acid). In some embodiments, the plurality of primers includes a sequence substantially complementary to a nucleic acid sequence encoding a constant region of a B cell receptor (e.g., a second target nucleic acid). In some embodiments, the plurality of primers includes a sequence substantially complementary to a nucleic acid sequence encoding a constant region of a T cell receptor (e.g., a second target nucleic acid).

In some embodiments, the functional domain includes a primer binding site or a sequencing specific site.

In some embodiments, the extending in step (e) includes the use of a reverse transcriptase. In some embodiments, incorporating the polynucleotide sequence to the 3' end of the extension product in step (f) includes the use of a terminal deoxynucleotidyl transferase. In some embodiments, incorporating the polynucleotide sequence to the 3' end of the extension product in step (f) includes the use of a reverse transcriptase.

In some embodiments, the method includes removing the first target nucleic acid, or any other nucleic acid hybridized to the ligation product, before the first capture sequence of the second probe hybridizes to the first capture domain of the first capture probe.

In some embodiments, the method includes removing the second target nucleic acid, or any other nucleic acid hybridized to the one or more extension products, before the polynucleotide sequence hybridizes to the second capture domain of the second capture probe.

In some embodiments, the removing includes the use of an RNase. In some embodiments, the RNase is RNase A. In some embodiments, the RNase is RNase P. In some embodiments, the RNase is RNase T1. In some embodiments, the RNase is RNase H. In some embodiments, the removing includes heat.

In some embodiments, the extending in step (e) includes the use of a reverse transcriptase. In some embodiments, the reverse transcriptase has strand displacement activity. In some embodiments, the strand displacement activity of the reverse transcriptase displaces one or more primers of the plurality of primers from the target nucleic acid. In some embodiments, the strand displacement activity of the reverse transcriptase displaces the one or more extension products from the target nucleic acid.

In some embodiments, the extending in step (c) includes the use of a reverse transcriptase and a helicase.

In some embodiments, step (e) is performed after step (c). In some embodiments, step (e) is performed before step (c).

In some embodiments, the extending in step (e) includes the use of a reverse transcriptase (e.g., any suitable reverse transcriptase known in the art). In some embodiments, incorporating (e.g., adding) the polynucleotide sequence to the 3' end of the extension product in step (f) includes the use of the reverse transcriptase. In some embodiments, a second a primer hybridizes to the added polynucleotide sequence and the extension product can be further extended using the second primer as an extension template where the second primer includes a second capture sequence. In such embodiments, the extension product is further extended, thereby incorporating a complement of the second capture sequence into one or more extension products. In some embodiments, incorporating the polynucleotide sequence to the 3' end of the extension product in step (f) includes the use of a terminal transferase. In some embodiments, the terminal transferase is terminal deoxynucleotidyl transferase. In some embodiments, the reverse transcriptase or the terminal transferase adds at least three nucleotides to the extension product. In some embodiments, the reverse transcriptase or the terminal transferase adds 4, 5, 6, 7, 8, 9, 10, or more nucleotides (e.g., a polynucleotide sequence) to the 3' end of the extension product(s) in step (c). In some embodiments, the polynucleotide sequence added to the 3' end of the extension product(s) is 5'-CCC-3'. In some embodiments, the polynucleotide sequence added to 3' end of the extension product(s) is 5'-CGC-3'.

In some embodiments, step (e) is performed after step (c). In some embodiments, step (e) is performed before step (c).

As defined herein, "helicases" are enzymes that catalyze the reaction of separating or unwinding the helical structure of nucleic acid complexes, e.g., double-stranded DNA, double-stranded RNA, or DNA:RNA complexes, into single stranded components. Helicases generally are known to use a nucleoside triphosphate (NTP) (e.g., ATP) hydrolysis as a source of energy. In some embodiments, the method includes one or more single-stranded DNA binding proteins. In some embodiments, the one or more single-stranded DNA binding proteins includes one or more of: Tth RecA, E. coli RecA, T4 gp32 and ET-SSB. As defined herein, "single-stranded DNA binding proteins" or "SSBs" are proteins that bind to single-stranded DNA. SSBs, or functional equivalents, are found in a variety of organisms, including eukaryotes and bacteria. Single-stranded DNA is produced, for example, during aspects of DNA metabolism, DNA replication, DNA recombination, and DNA repair. As well as stabilizing single-stranded DNA, SSB proteins bind to and modulate the function of numerous proteins involved in the aforementioned processes. In addition, SSB proteins can destabilize ends of double-stranded nucleic acid (e.g., dsDNA). In some embodiments, the helicase has strand displacement activity. For example, the helicases and single-stranded DNA binding proteins described herein can unwind DNA:RNA complexes that allow a reverse transcriptase to reverse transcribe the target nucleic acid. In some embodiments, a helicase can unwind a first target nucleic acid: extension product complex (e.g., mRNA:cDNA) that is downstream of a second target nucleic acid:extension product complex, such that the target nucleic acid from the first complex (with or without the help of the SSBs) becomes available as template for further extension of the extension product in the second complex.

In some embodiments, helicases, including superhelicases, are also used in conjunction with SSB proteins during nucleic acid amplification. In some embodiments, the extending in step (e) includes the use of a superhelicase and a reverse transcriptase. In some embodiments, the superhelicase is selected from the group consisting of: Rep, PrcA, UvrB, RecBCD, and Tte-Uvrd. As defined herein a "superhelicase" is a mutant and/or a derivative of a helicase. Superhelicases can have increased processivity compared to helicases due to one or more derivations that can include mutated gene or substituted polypeptide sequences and/or cross-linked protein domains. Additionally, superhelicases can unwind double-stranded nucleic acid complexes without single-stranded DNA binding protein(s). In some embodiments, the helicase is a superhelicase. In some embodiments, superhelicases have increased processivity relative to helicases. In some embodiments, the superhelicase has strand displacement activity. For example, superhelicases can unwind double-stranded nucleic acid complexes longer than 150 base pairs.

In some embodiments, the extending includes the use of a polymerase. Any suitable polymerase can be used (e.g., Kapa HiFi). In some examples, 3' end of the first and/or second capture probe is extended using the ligation product or extension product as a template and 3' end of the ligation product or extension product is simultaneously extended using the first capture probe or second capture probe as a template (e.g., generating an extended ligation product and an extended capture product, respectively). In some examples, the extended ligation product and/or the extended capture product is released from the first or second capture probe. In some examples, the extended ligation product and/or the extended capture product is released via heat. In some examples, the extended ligation product and/or the extended capture product is denatured from the first or second capture probe. In some examples, the extended ligation product and/or the extended capture product is denatured from the first or second capture probe with KOH.

In some embodiments, the first spatial barcode and the second spatial barcode have the same sequence. In some embodiments, the first spatial barcode and the second spatial barcode have a different sequence.

In some embodiments, the released, extended ligation products and/or the extended captured products can be prepared for downstream applications, such as generation of a sequencing library and next-generation sequencing. Generating sequencing libraries are known in the art. For example, the extended ligation products and the extended captured products can be purified and collected for downstream amplification steps. The extended amplification products (e.g., from either or both of the extended ligation products and/or the extended capture products) can be amplified using PCR, where primer binding sites flank the spatial barcode and target nucleic acid (e.g., the first target nucleic acid, the second target nucleic acid), or a complement thereof, generating a library associated with a particular spatial barcode. In some embodiments, the library preparation can be quantitated and/or quality controlled to verify the success of the library preparation steps. The library amplicons are sequenced and analyzed to decode spatial information and the target nucleic acid sequence.

In some embodiments, the method includes generating a sequencing library. In some embodiments, the determining includes sequencing. Methods and systems for sequencing are known in the art and are described herein. In some embodiments, the sequencing is high-throughput sequencing. In some embodiments, the sequencing is long read sequencing.

Alternatively, or additionally, the amplicons can then be enzymatically fragmented and/or size-selected in order to provide for desired amplicon size. In some embodiments, when utilizing an Illumina® library preparation methodology, for example, P5 and P7, sequences can be added to the amplicons thereby allowing for capture of the library preparation on a sequencing flow cell (e.g., on Illumina sequencing instruments). Additionally, i7 and i5 can index sequences be added as sample indexes if multiple libraries are to be pooled and sequenced together. Further, Read 1 and Read 2 sequences can be added to the library preparation for sequencing purposes. The aforementioned sequences can be added to a library preparation sample, for example, via End Repair, A-tailing, Adaptor Ligation, and/or PCR. The cDNA fragments can then be sequenced using, for example, paired-end sequencing using TruSeq Read 1 and TruSeq Read 2 as sequencing primer sites, although other methods are known in the art.

Templated-Ligation

Targeted nucleic acid (e.g., DNA, RNA) capture can be an alternative to traditional capture methods (e.g., poly(A) capture) in order to interrogate spatial gene expression in a biological sample. However, as described herein targeted nucleic acid capture (e.g., template-ligation capture) can be used in conjunction with traditional capture methods. Generally, targeted nucleic capture is less affected by degradation and allows for sensitive measurement of specific genes of interest that otherwise might be missed with a whole transcriptomic approach. Targeted nucleic acid capture can be used to capture a defined set of nucleic acid molecules of interest, or it can be used at a whole transcriptome level, or anything in between. When combined with the spatial methods disclosed herein, the location and abundance of the nucleic acid targets can be determined.

In some embodiments, the methods described herein include a first probe. As used herein, a "first probe" and "second probe" can refer to a probe that hybridizes to all or a portion of a target nucleic acid and can be ligated to one or more additional probes (e.g., a second probe or a spanning probe). In some embodiments, "first probe" can be used interchangeably with "first probe oligonucleotide." In some embodiments, "second probe" can be used interchangeably with "second probe oligonucleotide." In some embodiments, the first probe and/or the second probe is a DNA probe.

In some embodiments, the first probe and/or the second probe includes ribonucleotides, deoxyribonucleotides, and/or synthetic nucleotides that are capable of participating in Watson-Crick type or analogous base pair interactions. In some embodiments, the first probe and/or the second probe includes deoxyribonucleotides. In some embodiments, the first probe and/or the second probe includes deoxyribonucleotides and ribonucleotides. In some embodiments, the first probe and/or the second probe includes a deoxyribonucleic acid that hybridizes to an analyte and includes a portion of the oligonucleotide that is not a deoxyribonucleic acid. For example, in some embodiments, the portion of the first oligonucleotide and/or the second oligonucleotide that is not a deoxyribonucleic acid is a ribonucleic acid or any other non-deoxyribonucleic acid nucleic acid as described herein. In some embodiments where the first probe and/or the second probe includes deoxyribonucleotides, hybridization of the first probe and/or the second probe to the nucleic acid (e.g., RNA, mRNA, etc.) molecule results in a DNA:RNA hybrid. In some embodiments, the first probe and/or the second probe includes only deoxyribonucleotides and upon hybridization of the first probe and/or the second probe to the mRNA molecule results in a DNA:RNA hybrid.

In some embodiments, the method includes a first probe and/or a second probe that includes one or more sequences that are substantially complementary to one or more sequences of an analyte. In some embodiments, a first probe includes a sequence that is substantially complementary to a first target sequence in the first target nucleic acid. In some embodiments, the sequence of the first probe that is substantially complementary to the first target sequence in the first target nucleic acid is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to the first target sequence in the first target nucleic acid. In some embodiments, the sequence of the second probe that is substantially complementary to the second target sequence in the first target nucleic acid is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to the second target sequence in the first target nucleic acid.

In some embodiments, a first probe and/or a second probe includes a sequence that is about 10 nucleotides to about 100 nucleotides (e.g., a sequence of about 10 nucleotides to about 90 nucleotides, about 10 nucleotides to about 80 nucleotides, about 10 nucleotides to about 70 nucleotides, about 10 nucleotides to about 60 nucleotides, about 10 nucleotides to about 50 nucleotides, about 10 nucleotides to about 40 nucleotides, about 10 nucleotides to about 30 nucleotides, about 10 nucleotides to about 20 nucleotides, about 20 nucleotides to about 100 nucleotides, about 20 nucleotides to about 90 nucleotides, about 20 nucleotides to about 80 nucleotides, about 20 nucleotides to about 70 nucleotides, about 20 nucleotides to about 60 nucleotides, about 20 nucleotides to about 50 nucleotides, about 20 nucleotides to about 40 nucleotides, about 20 nucleotides to about 30 nucleotides, about 30 nucleotides to about 100 nucleotides, about 30 nucleotides to about 90 nucleotides, about 30 nucleotides to about 80 nucleotides, about 30 nucleotides to about 70 nucleotides, about 30 nucleotides to about 60 nucleotides, about 30 nucleotides to about 50 nucleotides, about 30 nucleotides to about 40 nucleotides, about 40 nucleotides to about 100 nucleotides, about 40 nucleotides to about 90 nucleotides, about 40 nucleotides to about 80 nucleotides, about 40 nucleotides to about 70 nucleotides, about 40 nucleotides to about 60 nucleotides, about 40 nucleotides to about 50 nucleotides, about 50 nucleotides to about 100 nucleotides, about 50 nucleotides to about 90 nucleotides, about 50 nucleotides to about 80 nucleotides, about 50 nucleotides to about 70 nucleotides, about 50 nucleotides to about 60 nucleotides, about 60 nucleotides to about 100 nucleotides, about 60 nucleotides to about 90 nucleotides, about 60 nucleotides to about 80 nucleotides, about 60 nucleotides to about 70 nucleotides, about 70 nucleotides to about 100 nucleotides, about 70 nucleotides to about 90 nucleotides, about 70 nucleotides to about 80 nucleotides, about 80 nucleotides to about 100 nucleotides, about 80 nucleotides to about 90 nucleotides, or about 90 nucleotides to about 100 nucleotides).

In some embodiments, a sequence of the first probe and/or the second probe that is substantially complementary to a sequence in the target nucleic acid includes a sequence that is about 5 nucleotides to about 50 nucleotides (e.g., about 5 nucleotides to about 45 nucleotides, about 5 nucleotides to about 40 nucleotides, about 5 nucleotides to about 35 nucleotides, about 5 nucleotides to about 30 nucleotides, about 5 nucleotides to about 25 nucleotides, about 5 nucleotides to about 20 nucleotides, about 5 nucleotides to about 15 nucleotides, about 5 nucleotides to about 10 nucleotides, about 10 nucleotides to about 50 nucleotides, about 10 nucleotides to about 45 nucleotides, about 10 nucleotides to about 40 nucleotides, about 10 nucleotides to about 35 nucleotides, about 10 nucleotides to about 30 nucleotides, about 10 nucleotides to about 25 nucleotides, about 10 nucleotides to about 20 nucleotides, about 10 nucleotides to about 15 nucleotides, about 15 nucleotides to about 50 nucleotides, about 15 nucleotides to about 45 nucleotides, about 15 nucleotides to about 40 nucleotides, about 15 nucleotides to about 35 nucleotides, about 15 nucleotides to about 30 nucleotides, about 15 nucleotides to about 25 nucleotides, about 15 nucleotides to about 20 nucleotides, about 20 nucleotides to about 50 nucleotides, about 20 nucleotides to about 45 nucleotides, about 20 nucleotides to about 40 nucleotides, about 20 nucleotides to about 35 nucleotides, about 20 nucleotides to about 30 nucleotides, about 20 nucleotides to about 25 nucleotides, about 25 nucleotides to about 50 nucleotides, about 25 nucleotides to about 45 nucleotides, about 25 nucleotides to about 40 nucleotides, about 25 nucleotides to about 35 nucleotides, about 25 nucleotides to about 30 nucleotides, about 30 nucleotides to about 50 nucleotides, about 30 nucleotides to about 45 nucleotides, about 30 nucleotides to about 40 nucleotides, about 30 nucleotides to about 35 nucleotides, about 35 nucleotides to about 50 nucleotides, about 35 nucleotides to about 45 nucleotides, about 35 nucleotides to about 40 nucleotides, about 40 nucleotides to about 50 nucleotides, about 40 nucleotides to about 45 nucleotides, or about 45 nucleotides to about 50 nucleotides).

In some embodiments, a first probe includes a functional sequence. In some embodiments, a functional sequence includes a primer sequence.

In some embodiments, a second probe includes a "first capture sequence." As used herein, a "first capture sequence" is a sequence, domain, or moiety that can bind specifically to a capture domain of a capture probe (e.g., the first capture domain of a first capture probe). In some embodiments, a second probe includes a sequence from 5' to 3': a sequence that is substantially complementary to a sequence in the analyte and a first capture sequence.

In some embodiments, a first capture sequence includes a poly(A) sequence. In some embodiments, the first capture sequence includes a poly-uridine sequence, a poly-thymidine sequence, or both. In some embodiments, the first capture sequence includes a random sequence (e.g., a random hexamer or octamer). In some embodiments, the first capture sequence is complementary to a capture domain in a capture probe that detects a particular target nucleic acid.

In some embodiments, a blocking moiety that interacts with the first capture domain is provided. In some embodiments, a blocking moiety includes a sequence that is complementary or substantially complementary to a first capture domain. In some embodiments, a blocking moiety prevents the first capture sequence from binding the capture probe when present. In some embodiments, a blocking moiety is removed prior to binding the first capture sequence (e.g., present in a ligated probe) to a first capture probe. In some embodiments, a blocking moiety includes a poly-uridine sequence, a poly-thymidine sequence, or both. In some embodiments, the first capture sequence includes ribonucleotides, deoxyribonucleotides, and/or synthetic nucleotides that are capable of participating in Watson-Crick type or analogous base pair interactions. In some embodiments, the capture domain sequence includes at least 10, 11, 12, 13, 14, 15, 16, 17, 18, 19, or 20 nucleotides. In some embodiments, the capture domain sequence includes at least 25, 30, or 35 nucleotides.

In some embodiments, the method includes releasing the blocking moiety from the first capture domain of the first capture probe prior to hybridizing the first capture sequence of the ligation product to the first capture domain. In some embodiments, releasing the blocking moiety from the first capture domain of the first capture probe includes contacting the biological sample with an endoribonuclease. In some embodiments, releasing the ligation product from the first target nucleic acid includes contacting the biological sample with an endoribonuclease. In some embodiments, the endoribonuclease is an RNase H enzyme.

In some embodiments, after hybridization of the probe oligonucleotides (e.g., a first probe, a second probe) to the target nucleic acid the probe (e.g., a first probe, a second probe) can be ligated together, creating a single ligation product that includes one or more sequences that are complementary to the analyte. Ligation can be performed enzymatically or chemically, as described herein.

In some instances, the ligation is an enzymatic ligation reaction, using a ligase (e.g., T4 RNA ligase (Rnl2), a SplintR ligase (also known as PBCV-1 DNA ligase or Chlorella virus DNA ligase), a single stranded DNA ligase, or a T4 DNA ligase). See, e.g., Zhang et al.; RNA Biol. 2017; 14(1): 36-44, which is incorporated by reference in its entirety, for a description of KOD ligase. Following the enzymatic ligation reaction, the probes can be considered ligated.

In some embodiments, the first probe and the second probe hybridize to sequences that are not adjacent to each other on the analyte (e.g., nucleic acid). In some embodiments, the complementary sequences to which the first probe and the second probe hybridize are 1, 2, 3, 4, 5, 6, 7, 8, 9, 10, about 15, about 20, about 25, about 30, about 35, about 40, about 45, about 50, about 55, about 60, about 65, about 70, about 75, about 80, about 85, about 90, about 95, about 100, about 125, or about 150 nucleotides away from each other. Gaps between the probes may first be filled prior to coupling (e.g., ligation), using, for example, dNTPs in combination with a polymerase such as polymerase mu, DNA polymerase, RNA polymerase, reverse transcriptase, VENT polymerase, Taq polymerase, and/or any combinations, derivatives, and variants (e.g., engineered mutants) thereof. In some embodiments, when the first and second probes are separated from each other by one or more nucleotides, deoxyribonucleotides are used to extend and couple (e.g., ligate) the first and second probe oligonucleotides. In some embodiments, the first probe and the second probe hybridize to sequences that are at least 1, 2, 3, 4, 5, 6, 7, 8, 9, 10, or more nucleotides away from one another.

In some embodiments, the first probe is extended with a DNA polymerase, thereby (i) filling in a gap between the first probe and the second probe and (ii) generating an extended first probe. In some embodiments, the second probe is extended with a DNA polymerase, thereby (i) filling in a gap between the first probe and the second probe and (ii) generating an extended second probe.

In some embodiments, about 1000, 5000, 10000, 15000, 20,000 or more probe pairs (e.g., a probe pair including a first probe and a second probe) are used in the methods described herein. For example, contacting the first probe and the second probe with the biological sample includes contacting the biological sample with 5000 or more probe pairs, where a probe pair of the 5000 or more probe pairs includes the first probe and the second probe.

Gap-Filling Method

Also provided herein are methods for determining a location of a target nucleic acid in a biological sample, the method including: (a) contacting the biological sample with a first probe and a second probe, where: (i) the first probe includes a sequence that is substantially complementary to a sequence of the target nucleic acid and a functional domain, and (ii) the second probe includes a sequence that is substantially complementary to a sequence of the target nucleic acid and a capture sequence that is complementary to all or a portion of a capture domain; (b) hybridizing the first probe and the second probe to the target nucleic acid, where the first probe and the second probe hybridize to non-adjacent sequences; (c) generating a sequence complementary to the target nucleic acid between the first probe and second probe using the target nucleic acid as a template by gap-filling, thereby by generating an extension product; (d) ligating the extension product to the first probe or the second probe, thereby generating a ligation product; (e) hybridizing the capture sequence of the ligation product to a capture domain on an array, where the array includes a plurality of capture probes, where a capture probe of the plurality of capture probes includes a spatial barcode and the capture domain; and (f) determining (i) the sequence of the spatial barcode, or a complement thereof, and (ii) all or a portion of the sequence of the ligation product hybridized to the capture domain, or a complement thereof, and using the determined sequences of (i) and (ii) to determine the location of the target nucleic acid in the biological sample.

In some embodiments, the biological sample is disposed on the array including the plurality of capture probes. In some embodiments, the biological sample is disposed on a first substrate, and where the array including the plurality of capture probes is disposed on a second substrate. In some embodiments, the method includes aligning the first substrate with the second substrate, such that at least a portion of the biological sample is aligned with at least a portion of the array on the second substrate.

In some embodiments, the hybridizing in steps (c) includes passive migration of the ligation product from the biological sample to the array. In some embodiments, the hybridizing in steps (e) includes active migration of the ligation product from the biological sample to the array, and optionally, where the active migration includes electrophoresis.

In some embodiments, the gap-filling in step (b) includes the use of a DNA polymerase or a reverse transcriptase. In some embodiments, generating the sequence complementary to the target nucleic acid in step (c) includes extending the first probe. In some embodiments, generating the sequence complementary to the target nucleic acid in step (c) includes extending the second probe.

In some embodiments, contacting the first probe and the second probe with the biological sample includes contacting the biological sample with 5000 or more probe pairs, where a probe pair of the 5000 or more probe pairs includes the first probe and the second probe.

In some embodiments, generating the ligation product includes ligating the extension product to the second probe using enzymatic ligation or chemical ligation. In some embodiments, the enzymatic ligation utilizes a ligase. In some embodiments, the ligase is one or more of a T4 RNA ligase (Rnl2), a SplintR ligase, a single stranded DNA ligase, or a T4 DNA ligase.

In some embodiments, the functional domain includes a primer binding sequence or a sequencing specific site.

In some embodiments, the method includes providing a blocking moiety that interacts with the capture domain of the capture probe. In some embodiments, the blocking moiety is a DNA probe. In some embodiments, the method includes releasing the blocking moiety from the capture domain of the first capture probe. In some embodiments, the blocking moiety includes a poly-uridine sequence, a poly-thymidine sequence, or both. In some embodiments, releasing the blocking moiety from the capture domain of the capture probe includes contacting the biological sample with an endoribonuclease. In some embodiments, releasing the ligation product from the target nucleic acid includes contacting the biological sample with an endoribonuclease. In some embodiments, the endoribonuclease is RNase H.

In some embodiments, the capture sequence includes a poly-adenylated sequence. In some embodiments, the capture sequence includes a fixed sequence. In some embodiments, the fixed sequence is a homopolynucleotide sequence. In some embodiments, the fixed sequence is a heteropolynucleotide sequence.

In some embodiments, the first probe and/or the second probe is a DNA probe. In some embodiments, the first probe and/or the second probe is an RNA probe. In some embodiments, the second probe includes one or more locked nucleic acids, one or more RNA nucleotides, or both.

In some embodiments, the first probe includes a sequence substantially complementary to a nucleic acid sequence encoding a constant region of an antibody. In some embodiments, the first probe includes a sequence substantially complementary to a nucleic acid sequence encoding a constant region of a B cell receptor. In some embodiments, the first probe includes a sequence substantially complementary to a nucleic acid sequence encoding a constant region of a T cell receptor. In some embodiments, the second probe includes a sequence substantially complementary to a nucleic acid sequence encoding a variable region of a B cell receptor. In some embodiments, the second probe includes a sequence substantially complementary to a nucleic acid sequence encoding a variable region of a T cell receptor.

In some embodiments, the DNA polymerase or the reverse transcriptase lack strand displacement activity.

In some embodiments, the target nucleic acid is RNA. In some embodiments, the RNA is mRNA. In some embodiments, the mRNA includes a sequence encoding a B cell receptor. In some embodiments, the mRNA includes a sequence encoding a T cell receptor. In some embodiments, the mRNA includes a sequence that does not encode a B cell receptor or a fragment thereof or a T cell receptor or a fragment thereof.

In some embodiments, the method includes contacting the biological sample with a third probe and a fourth probe, where: (i) the third probe includes a sequence that is substantially complementary to a sequence of a second target nucleic acid and a functional domain; (ii) the fourth probe includes a sequence that is substantially complementary to a sequence of the second target nucleic acid and a second capture sequence that is complementary to all or a portion of a second capture domain; hybridizing the third probe and the fourth probe to the second target nucleic acid; generating a second ligation product by ligating the third probe to the fourth probe; hybridizing the second capture sequence of the second ligation product to the second capture domain of a second capture probe on the array, where the second capture probe includes a second spatial barcode and the second capture domain; determining (i) the sequence of the second spatial barcode, or a complement thereof, and (ii) all or a portion of the ligation product, or a complement thereof, and using the determined sequences of (i) and (ii) to determine the location of the second target nucleic acid in the biological sample.

In some embodiments, the first capture domain and/or the second capture domain includes a fixed sequence. In some embodiments, the first capture domain and the second capture domain have the same sequence. In some embodiments, the first capture domain and the second capture domain have a different sequence.

In some embodiments, the second target nucleic acid is RNA or DNA. In some embodiments, the RNA is mRNA or the DNA is cDNA. In some embodiments, the mRNA includes a sequence encoding a B cell receptor or a fragment thereof. In some embodiments, the mRNA includes a sequence encoding a T cell receptor or a fragment thereof. In some embodiments, the mRNA includes a sequence that does not encode a B cell receptor or a fragment thereof or a T cell receptor or a fragment thereof.

In some embodiments, the method includes removing the second target nucleic acid, or any other nucleic acid hybridized to the second ligation product, before the second capture sequence hybridizes to the second capture domain of the second capture probe. In some embodiments, the removing includes the use of an RNase. In some embodiments, the RNase includes RNase H. In some embodiments, the removing includes the use of heat.

In some embodiments, the method includes a step of extending a 3' end of the second ligation product using the second capture probe as a template, thereby generating an extended ligation product; and/or extending the second capture probe using the second ligation product as a template, thereby generating a second extended capture probe.

In some embodiments, the ligation product (e.g., the single-stranded ligation product(s)) hybridizes to the capture domain of the capture probe on the substrate. In some embodiments, 3' end of the capture probe is extended using the ligation product as a template. In some embodiments, 3' end of the ligation product is extended using the capture probe as a template, thereby generating an extended ligation product. In some embodiments, both the first capture probe, and the extension products hybridized thereto, are extended from their 3' ends.

In some embodiments, the ligation product is released from the capture probe. In some embodiments, the releasing includes heat. In some embodiments, the releasing includes KOH.

In some embodiments, the released, extended ligation products can be prepared for downstream applications, such as generation of a sequencing library and next-generation sequencing. Generating sequencing libraries are known in the art. For example, the extended ligation products can be purified and collected for downstream amplification steps. The extended amplification products can be amplified using PCR, where primer binding sites flank the spatial barcode and target nucleic acid (e.g., the first target nucleic acid, the second target nucleic acid), or a complement thereof, generating a library associated with a particular spatial barcode. In some embodiments, the library preparation can be quantitated and/or quality controlled to verify the success of the library preparation steps. The library amplicons are sequenced and analyzed to decode spatial information and the target nucleic acid sequence.

In some embodiments, the method includes generating a sequencing library as described herein. In some embodiments, the determining includes sequencing. Methods and systems for sequencing are known in the art and are described herein. In some embodiments, the sequencing is high-throughput sequencing.

Further Steps

The following embodiments can be used with any of the methods described herein. In some embodiments, the biological sample is imaged. In some embodiments, the biological sample is visualized or imaged using bright field microscopy. In some embodiments, the biological sample is visualized or imaged using fluorescence microscopy. Additional methods of visualization and imaging are known in the art. Non-limiting examples of visualization and imaging include expansion microscopy, bright field microscopy, dark field microscopy, phase contrast microscopy, electron microscopy, fluorescence microscopy, reflection microscopy, interference microscopy and confocal microscopy. In some embodiments, the sample is stained and imaged prior to adding reagents for performing the methods as disclosed herein to the biological sample.

In some embodiments, the method includes staining the biological sample. In some embodiments, the staining includes the use of hematoxylin and eosin. In some embodiments, a biological sample can be stained using any number of biological stains, including but not limited to, acridine orange, Bismarck brown, carmine, coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, or safranin.

The biological sample can be stained using known staining techniques, including Can-Grunwald, Giemsa, hematoxylin and eosin (H&E), Jenner's, Leishman, Masson's trichrome, Papanicolaou, Romanowsky, silver, Sudan, Wright's, and/or Periodic Acid Schiff (PAS) staining techniques. PAS staining is typically performed after formalin or acetone fixation.

In some embodiments, the staining includes the use of a detectable label selected from the group consisting of a radioisotope, a fluorophore, a chemiluminescent compound, a bioluminescent compound, or a combination thereof.

In some embodiments, the method includes a step of permeabilizing the biological sample (e.g., a tissue section). For example, the biological sample can be permeabilized to facilitate transfer of the extension products to the capture probes on the array. In some embodiments, the permeabilizing includes the use of an organic solvent (e.g., acetone, ethanol, and methanol), a detergent (e.g., saponin, Triton X-100™, Tween-20™, or sodium dodecyl sulfate (SDS)), an enzyme (an endopeptidase, an exopeptidase, a protease), or combinations thereof. In some embodiments, the permeabilizing includes the use of an endopeptidase, a protease, SDS, polyethylene glycol tert-octylphenyl ether, polysorbate 80, and polysorbate 20, N-lauroylsarcosine sodium salt solution, saponin, Triton X-100™, Tween-20™, or combinations thereof. In some embodiments, the endopeptidase is pepsin. In some embodiments, the endopeptidase is Proteinase K. Additional methods for sample permeabilization are described, for example, in Jamur et al., *Method Mol. Biol.* 588:63-66, 2010, the entire contents of which are incorporated herein by reference.

In some embodiments, the biological sample is a tissue sample. In some embodiments, the biological sample (e.g., tissue sample) is a tissue microarray. A tissue microarray contains multiple representative tissue samples from different cases assembled on a single histologic slide, and therefore allows high throughput analysis of multiple specimens at the same time. Tissue microarrays are paraffin blocks produced by extracting cylindrical tissue cores from different paraffin donor blocks and re-embedding these into a single recipient (microarray) block at defined array coordinates.

In some embodiments, the tissue sample is a fixed tissue sample. For example, fixing the biological sample can include the use of a fixative including: ethanol, methanol, acetone, formaldehyde, paraformaldehyde-Triton, glutaraldehyde, and combinations thereof. In some embodiments, the biological sample can be fixed using PAXgene. For example, the biological sample can be fixed using PAXgene in addition, or alternatively to, a fixative disclosed herein or known in the art (e.g., an alcohol such as ethanol or methanol, acetone, acetone-alcohol, formalin, paraformaldehyde, paraformaldehyde-Triton, glutaraldehyde). PAXgene is a non-cross-linking mixture of different alcohols, acid and a soluble organic compound that preserves morphology and bio-molecules. It is a two-reagent fixative system in which tissue is firstly fixed in a solution containing methanol and acetic acid then stabilized in a solution containing ethanol. See, Ergin B. et al., J Proteome Res. 2010 Oct. 1;9(10):5188-96; Kap M. et al., PLOS One.; 6(11): e27704 (2011); and Mathieson W. et al., Am J Clin Pathol.; 146(1):25-40 (2016), each of which are hereby incorporated by reference in their entirety, for a description and evaluation of PAXgene for tissue fixation.

In some embodiments, the fixed tissue sample is a formalin-fixed paraffin embedded tissue sample, paraformaldehyde fixed tissue sample, a methanol fixed tissue sample, or an acetone fixed tissue sample. In some embodiments, the tissue sample is a fresh frozen tissue sample. In some embodiments, the biological sample is a tissue section. In some embodiments, the biological sample is a fixed tissue section (e.g., a fixed tissue section prepared by any of the methods described herein).

The tissue sample can be obtained from any suitable location in a tissue or organ of a subject, e.g., a human subject. In some embodiments, the tissue sample is a mouse sample. In some embodiments, the tissue sample is a human sample. In some embodiments, the tissue sample can be derived from skin, brain, breast, lung, liver, kidney, prostate, tonsil, thymus, testes, bone, lymph node, ovary, eye, heart, or spleen (e.g., from mouse or human). In some embodiments, the tissue sample is derived from normal or diseased tissue. In some embodiments, the sample is an embryo sample. The embryo sample can be a non-human embryo sample. In some instances, the sample is a mouse embryo sample.

EXEMPLARY APPLICATIONS

Also provided herein are uses for the disclosed methods. For example, provided herein are methods for determining the presence and/or abundance of an immune cell clonotype at a location in a biological sample. Some embodiments of any of the methods described herein include capturing transcripts to identify an immune cell clonotype. Thus, the disclosed methods of 5' capture of target nucleic acids in combination with templated ligation can be used for determining the presence and/or abundance of an immune cell clonotype at a location in a biological sample. Identifying the clonal regions, e.g., regions defined by the places where variable (V), diverse (D), and/or joining (J) segments join to from the complementarity determining regions, including CDR1, CDR2, and CDR3, which provide specificity to the TCRs and/or BCRs, and by coupling clonal information to spatial information, it is possible to understand which T-cell and B-cell clonotypes may be specifically interacting with given cell types within a biological sample.

The disclosed methods are also useful in a clinical setting (e.g., monitoring minimal residual disease (MRD)). Patients treated for many cancers often retain an MRD related to the cancer. That is, even though a patient may have by clinical measures a complete remission of the disease in response to treatment, a small fraction of the cancer cells may remain that have escaped destruction. The type and size of this residual population can be an important prognostic factor for the patient's continued treatment. Thus, the more sensitive the measurement of MRD, the more likely that a subsequent course of treatment will be successful.

In particular, a feature of certain acute lymphoblastic leukemias (ALLs) is the sequence evolution of clonotypes associated with the disease. Although treatment outcomes in ALL have improved dramatically over the past fifty years, a significant proportion of patients will ultimately relapse, usually with disease that is highly refractory to additional therapy. It is generally thought that these relapses are due to residual leukemic cells that are resistant to therapy and remain undetected during clinical remission. Clonality of B-cell populations can be assessed by analysis of gene rearrangements that occur at the immunoglobulin heavy chain (IgH) gene locus and the resulting unique VDJ rearrangements are used as clonotypic markers in precursor-B-cell ALL. Precursor-B-cell ALL is generally thought to be a clonal disease resulting from malignant transformation and expansion of a single B-cell; however, changes in clonal IgH rearrangements between initial diagnosis and relapse has been shown in a significant proportion of pre-B ALL cases. Thus, the disclosed methods can be used for diagnosing and monitoring sequence evolution of IgH clonotypes in ALL, particularly precursor B cell ALL.

In many malignant lymphoid and myeloid neoplasms, a diagnostic tissue sample, such as a peripheral blood sample or a bone marrow sample, is obtained before treatment from which a clonotype profile is generated (a diagnostic clonotype profile). One or more disease-correlated clonotypes are identified in the clonotype profile, usually as the clonotypes having the highest frequencies, e.g., greater than 5 percent. After treatment, the presence, absence, or frequency of such correlating clonotypes is assessed periodically to determine whether a remission is holding or whether the neoplasm is returning or relapsing, based on the presence of, or an increase in the frequency of, the correlating clonotypes (or related clonotypes) in a post-treatment clonotype profile. That is, after treatment, minimal residual disease of the cancer is assessed based on the presence, absence, or frequency of the correlating clonotypes and/or related clonotypes, such as clonotypes evolved therefrom by further substitution, or other mechanisms. In one aspect of the invention, a measure of MRD is taken as a frequency of the one or more clonotypes initially identified as being correlated with the cancer together with the clonotypes evolved therefrom after such initial identification.

Provided herein is a method of monitoring minimal residual disease of a B cell leukemia (e.g., acute lymphoblastic leukemia) patient by assaying one or more patient-specific immune cell clonotypes correlated with the B cell leukemia. In some embodiments, the method includes (a) obtaining from the patient a biological sample comprising B-cells; and (b) determining from the biological sample a presence, absence and/or level of one or more patient-specific immune cell clonotypes correlated with the B cell acute lymphoblastic leukemia and/or previously unrecorded clonotypes evolved therefrom. The method can include repeating step (b) one or more times on a successive sample from the patient to monitor the B cell acute lymphoblastic leukemia. In some embodiments, determining the presence, absence and/or level of one or more patient-specific immune cell clonotypes is performed in accordance with any method of determining a location of a target nucleic acid disclosed herein, including methods of 5' capture of target nucleic acids.

In some aspects, the method includes monitoring and treating a patient. For example, in some embodiments, the methods of monitoring minimal residual disease further include a step of modifying a treatment regimen of the patient based on a presence, absence and/or level of the one or more patient-specific clonotypes and clonotypes related thereto. The patient can be treated in accordance with suitable treatment regimens in the art. After treatment, the presence, absence or frequency of correlating clonotypes is assessed periodically to determine whether a remission is holding or whether the neoplasm is returning or relapsing, based on the presence of, or an increase in the frequency of, the correlating clonotypes (or related clonotypes) in a post-treatment clonotype profile. That is, after treatment, minimal residual disease of the cancer is assessed based on the presence, absence or frequency of the correlating clonotypes and/or related clonotypes. In one aspect of the invention, a measure of MRD is taken as a frequency of the one or more clonotypes initially identified as being correlated with the cancer together with the clonotypes evolved therefrom after such initial identification. If increased numbers of leukemia cells are detected (e.g., between successive MRD measurements), then a relapse has taken place and the treatment regimen is modified to regain a remissive state. The modification may include use of a different chemotherapeutic combination, use of a different administration schedule, use of different amounts of drug, or a switch to a differ kind of therapy.

Sandwich Configurations

Some steps of the methods described herein can be performed in a biological sample (e.g., in situ) prior to contacting, or bringing in proximity, the biological sample with the array including a plurality of capture probes. In some embodiments, the biological sample is disposed or placed on the array including the plurality of capture probes prior to step (a). In some embodiments, the biological sample is disposed or placed on the array including the plurality of capture probes prior to step (d). In some embodiments, the biological sample is not disposed or placed on the array. For example, the biological sample can be placed on a substrate (e.g., a glass slide) that does not include a spatial array. In some embodiments, the substrate including the biological sample can be aligned with the array (e.g., "sandwiched") such that at least a portion of the biological sample is aligned with at least a portion of the array. In embodiments where the biological sample is disposed or placed on a substrate, steps (a)-(c) can be performed prior to aligning the substrate with the array as described herein. In embodiments where the biological sample is disposed or placed on a substrate, steps (a)-(c) can be performed after aligning the substrate with the array as described herein.

In some embodiments, one or more extension products generated from the biological sample are released from the biological sample and migrate to a substrate including an array of capture probes where the extension product(s) hybridize to the capture probes of the array. In some embodiments, the release and migration of the extension product(s) to the substrate including the array of capture probes occurs in a manner that preserves the original spatial context of the extension product(s) in the biological sample. In some embodiments, the biological sample is mounted on a first substrate and the substrate including the array of capture probes is a second substrate. In some embodiments, the method is facilitated by a sandwiching process. Sandwiching processes are described in, e.g., U.S. Patent Application Pub. No. 20210189475, WO 2021/252747, and WO 2022/061152A. In some embodiments, the sandwiching process may be facilitated by a device, sample holder, sample handling apparatus, or system described in, e.g., U.S. Patent Application Pub. No. 20210189475, WO 2021/252747, or WO 2022/061152A.

In some embodiments, the sandwiching process includes: mounting the first substrate on a first member of a support device, the first member configured to retain the first substrate; mounting the second substrate on a second member of the support device, the second member configured to retain the second substrate, applying a reagent medium to the first substrate and/or the second substrate, the reagent medium comprising a permeabilization agent, operating an alignment mechanism (also referred to herein as an adjustment mechanism) of the support device to move the first member and/or the second member such that a portion of the biological sample is aligned (e.g., vertically aligned) with a portion of the array of capture probes and within a threshold distance of the array of capture probes, and such that the portion of the biological sample and the capture probe contact the reagent medium, where the permeabilization agent releases the extension product(s) from the biological sample.

The sandwiching process methods described above can be implemented using a variety of hardware components. For example, the sandwiching process methods can be implemented using a sample holder (also referred to herein as a support device, a sample handling apparatus, and an array alignment device). In some embodiments of a sample holder, the sample holder can include a first member including a first retaining mechanism configured to retain a first substrate comprising a sample. The first retaining mechanism can be configured to retain the first substrate disposed in a first plane. The sample holder can further include a second member including a second retaining mechanism configured to retain a second substrate disposed in a second plane. The sample holder can further include an alignment mechanism connected to one or both of the first member and the second member. The alignment mechanism can be configured to align the first and second members along the first plane and/or the second plane such that the sample contacts at least a portion of the reagent medium when the first and second members are aligned and within a threshold distance along an axis orthogonal to the second plane. The adjustment mechanism may be configured to move the second member along the axis orthogonal to the second plane and/or move the first member along an axis orthogonal to the first plane.

In some embodiments, the adjustment mechanism includes a linear actuator. In some embodiments, the linear actuator is configured to move the second member along an axis orthogonal to the plane or the first member and/or the second member. In some embodiments, the linear actuator is configured to move the first member along an axis orthogonal to the plane of the first member and/or the second member. In some embodiments, the linear actuator is configured to move the first member, the second member, or both the first member and the second member at a velocity of at least 0.1 mm/sec. In some embodiments, the linear actuator is configured to move the first member, the second member, or both the first member and the second member with an amount of force of at least 0.1 lbs.

Figure 8A:
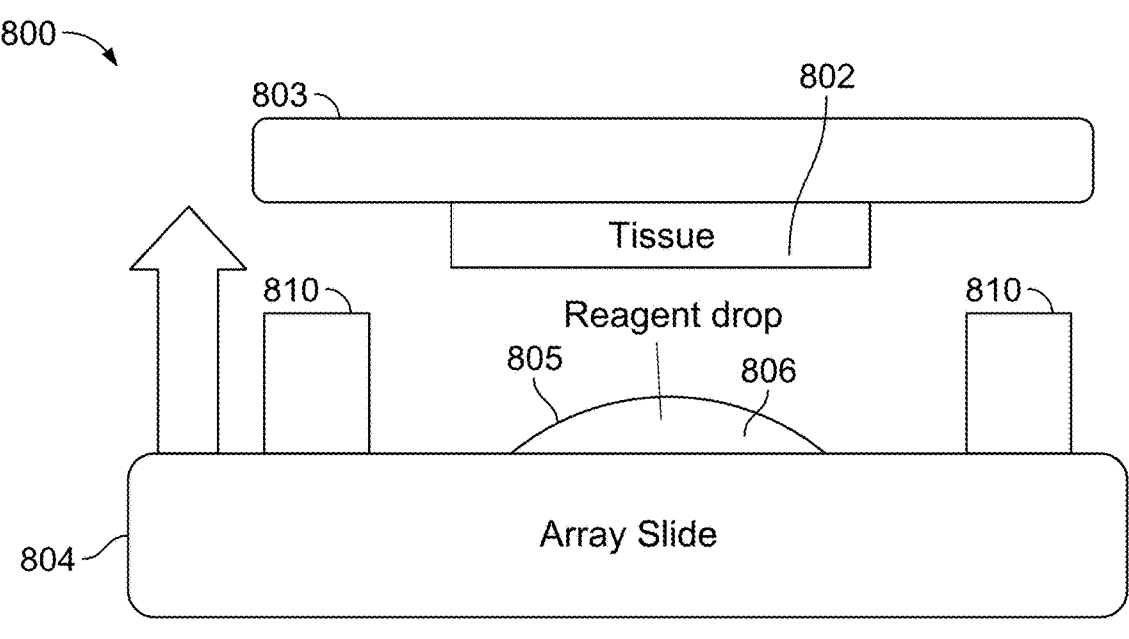
FIGS. 8A-B are schematic diagrams depicting exemplary sandwiching embodiments.

FIG. 8A shows an exemplary sandwiching process 800 where a first substrate (e.g., slide 803), including a biological sample 802 (e.g., a tissue section), and a second substrate (e.g., slide 804 including spatially barcoded capture probes 806) are brought into proximity with one another. As shown in FIG. 8A a liquid reagent drop (e.g., permeabilization solution 805) is introduced on the second substrate in proximity to the capture probes 806 and in between the biological sample 802 and the second substrate (e.g., slide 804 including spatially barcoded capture probes 806). The permeabilization solution 805 can release extension product (s) that can be captured (e.g., hybridized) by the capture probes 806 of the array. As further shown, one or more spacers 810 can be positioned between the first substrate (e.g., slide 803) and the second substrate (e.g., slide 804 including spatially barcoded capture probes 806). The one or more spacers 810 may be configured to maintain a separation distance between the first substrate and the second substrate. While the one or more spacers 810 is shown as disposed on the second substrate, the spacer may additionally or alternatively be disposed on the first substrate.

Figure 8B:
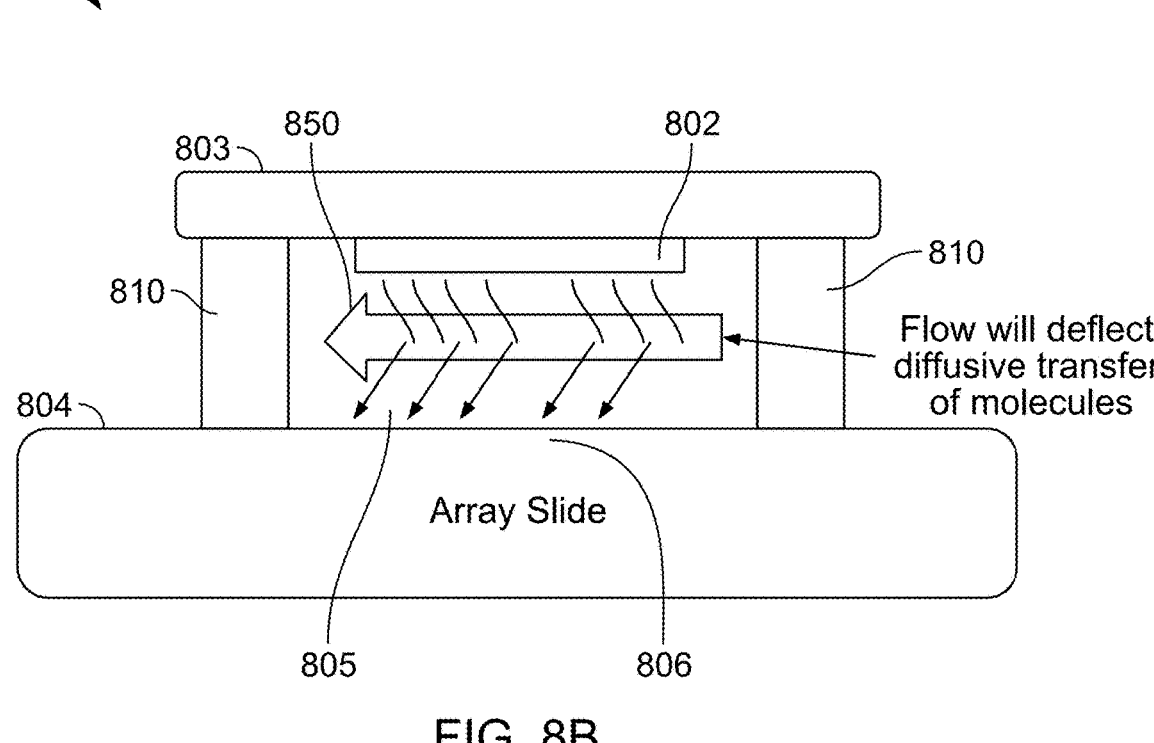

FIG. 8B shows a fully formed sandwich configuration creating a chamber 850 formed from the one or more spacers 810, the first substrate (e.g., the slide 803), and the second substrate (e.g., the slide 804 including spatially barcoded capture probes 806) in accordance with some example implementations. In FIG. 8B, the liquid reagent (e.g., the permeabilization solution 805) fills the volume of the chamber 850 and can create a permeabilization buffer that allows extension product(s) to diffuse from the biological sample 802 toward the capture probes 806 of the second substrate (e.g., slide 804). In some aspects, flow of the permeabilization buffer may deflect extension product(s) from the biological sample 802 and can affect diffusive transfer of extension product(s) for spatial analysis. A partially or fully sealed chamber 850 resulting from the one or more spacers 810, the first substrate, and the second substrate can reduce or prevent flow from undesirable convective movement of transcripts and/or molecules over the diffusive transfer from the biological sample 802 to the capture probes 806.

Compositions

Provided herein are compositions including: a) a first probe and a second probe hybridized to a first target nucleic acid and ligated together, where the first probe and the second probe each include a sequence that is substantially complementary to adjacent sequences of the first nucleic acid and where one of the first probe or the second probe includes a first capture sequence; and b) a plurality of primers hybridized to a second target nucleic acid.

Also provided herein are compositions including: a) a first probe and a second probe hybridized to a first target nucleic acid and ligated together, where the first probe and the second probe each include a sequence that is substantially complementary to adjacent sequences of the first nucleic acid and where one of the first probe or the second probe includes a first capture sequence; and b) a plurality of primers hybridized to a second target nucleic acid, where the plurality of primers are extended thereby generating one or more extension products hybridized to the second target nucleic acid.

Also provided herein are compositions including: a) an array including a first plurality of capture probes and a second plurality of capture probes, where a first capture probe of the first plurality of capture probes includes a first spatial barcode and a first capture domain and where a second capture probe of the second plurality of capture probes includes a second spatial barcode and a second capture domain; b) a ligation product hybridized to the first capture domain; and c) one or more extension products hybridized to the second capture domain.

In some embodiments, the composition includes an RNase H enzyme. In some embodiments, the composition includes a ligase. In some embodiments, the first capture probe and/or the second capture probe further include a cleavage domain, one or more functional domains, a unique molecular identifier, and combinations thereof.

In some embodiments, the first and/or the second target nucleic acid is RNA. In some embodiments, the RNA is mRNA. In some embodiments, the mRNA includes a sequence encoding an antibody or a fragment thereof. In some embodiments, the mRNA includes a sequence encoding a T cell receptor or a fragment thereof. In some embodiments, the mRNA includes a sequence encoding a B cell receptor.

In some embodiments, the functional domain includes a primer binding site. In some embodiments, the functional domain includes a sequencing specific site.

In some embodiments, the composition includes a reverse transcriptase. In some embodiments, the composition includes a helicase. In some embodiments, the composition includes one or more single-stranded DNA binding protein selected from the group consisting of: Tth RecA, *E. coli* RecA, T4 gp32 and ET-SSB. In some embodiments, the composition includes a superhelicase selected from the group consisting of: Rep, PrcA, UvrB, RecBCD, and Tte-Uvrd.

In some embodiments, the extension products further include a sequence complementary to a region of the target nucleic acid that encodes a D sequence of an immune cell receptor.

Kits

Also provided herein are kits including: (a) an array including a plurality of first capture probes, where a first capture probe of the plurality of capture probes includes: (i) a first spatial barcode; and (ii) a first capture domain that binds a first capture sequence; and a second plurality of capture probes, where a second capture probe of the second plurality of capture probes includes: a second spatial barcode; and a second capture domain; (b) a first primer including a sequence complementary to a target nucleic acid, and a functional domain, where the functional domain includes a primer binding sequence or a sequencing specific sequence; (c) a second primer including a second capture sequence; (d) a plurality of probes including a first probe and a second probe, where the first probe and the second probe are substantially complementary to adjacent sequences of a target nucleic acid, where the second probe includes a first capture sequence that hybridizes the first capture domain; (e)

a plurality of enzymes including a ribonuclease and a ligase; and (f) instructions for performing any of the methods described herein.

In some kits, the second primer includes RNA. In some kits, the kit includes a plurality of primers, where the first primer is included in the plurality of primers. In some kits, the kit includes one or more permeabilization reagents. In some kits, the kit includes a reverse transcriptase and/or a polymerase.

In some kits, the first capture probe and/or the second capture probe include one or more additional functional domains, a unique molecular identifier, a cleavage domain, and combinations thereof.

Also provided herein are kits including: (a) an array including a plurality of first capture probes, where a first capture probe of the plurality of capture probes includes: (i) a first spatial barcode; and (ii) a first capture domain that binds a first capture sequence; and a second plurality of capture probes, where a second capture probe of the second plurality of capture probes includes: a second spatial barcode; and a second capture domain; (b) a plurality of primers, where a primer of the plurality of primers includes a sequence complementary to a target nucleic acid and a functional domain, where the functional domain is a primer binding sequence or a sequencing specific site; (c) a plurality of probes including a first probe and a second probe, where the first probe and the second probe are substantially complementary to adjacent sequences of a target nucleic acid, where the second probe includes a first capture sequence that hybridizes to the first capture domain; (e) a plurality of enzymes including a ribonuclease and a ligase; and (f) instructions for performing any of the methods described herein.

In some kits, the first capture probe and/or the second capture probe include one or more additional functional domains, a unique molecular identifier, a cleavage domain, and combinations thereof.

In some kits, the kit further includes a reverse transcriptase. In some kits, the kit includes a polymerase.

In some kits, the first capture domain and/or the second capture domain includes a fixed sequence.

In some kits, the kit includes a helicase. In some kits, the kit includes one or more single-stranded binding proteins includes one or more of: Tth RecA, E. coli RecA, T4 gp32 and ET-SSB.

In some kits, the kit includes a superhelicase, where the superhelicase is selected from the group consisting of: Rep, PrcA, UvrB, RecBCD, and Tte-Uvrd.

EXAMPLES

Example 1. 5' Capture of Target Nucleic Acids

Figures 2A, 2B:
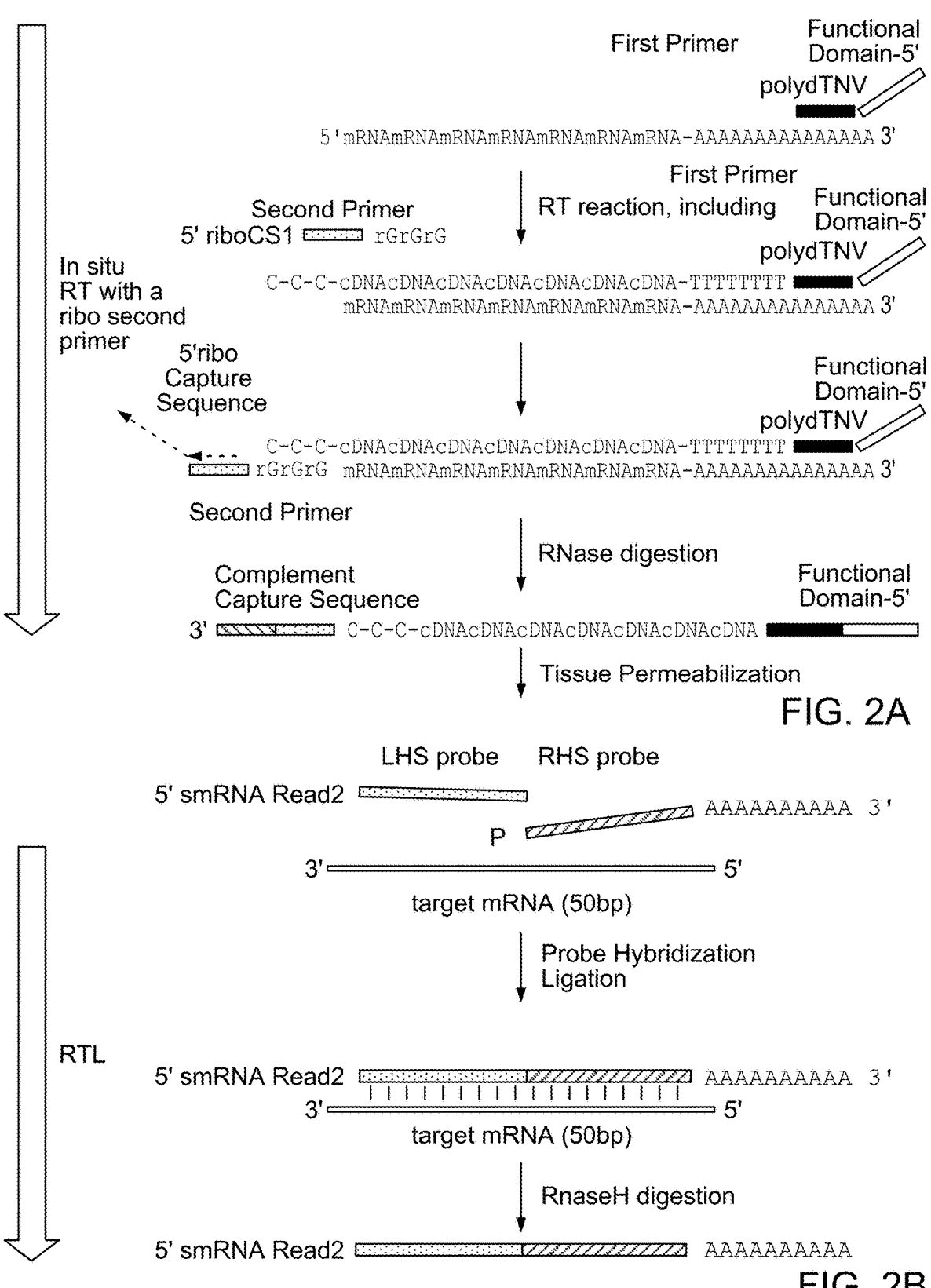
FIGS. 2A-B are schematic diagrams showing in situ reverse transcription of a target nucleic acid with a first primer to generate an extension product and the incorporation of a non-templated polynucleotide sequence and a complement of a capture sequence into the extension product which is capable of hybridizing to a capture domain of a capture probe (FIG. 2A), and a pair of templated ligation probes and a target nucleic acid where the probes hybridize to the target nucleic acid and are ligated to generate a ligation product (FIG. 2B).

FIG. 2A is a schematic showing generation of a cDNA by in situ reverse transcription of a target nucleic acid (e.g., mRNA) from a first primer including a sequence complementary to the target nucleic acid and a functional domain. The cDNA is further extended using a second primer that includes a capture sequence and a sequence complementary to a non-templated (e.g., homopolynucleotide) sequence.

More specifically, a biological sample containing a target nucleic acid is contacted with a first primer that includes a sequence complementary to the target nucleic acid (e.g., poly(dT) sequence, a poly(dTNV) sequence, a random sequence, a sequence encoding a constant region of a B cell receptor (e.g., an antibody), or a T cell receptor) and a functional domain. In some examples, the functional domain is a primer binding site. In some examples, the functional domain is a sequencing specific site (e.g., Read2 site). The target nucleic acid is reverse transcribed into cDNA and a polynucleotide sequence is added to the 3' end of the cDNA. FIG. 2A shows a homopolynucleotide sequence comprising cytosines, however, it is appreciated that other polynucleotide sequences can be added to the 3' end of the cDNA, including a heteropolynucleotide sequence, such as CGC. In some examples, the polynucleotide sequence is added by the reverse transcriptase. In some examples, the polynucleotide sequence is added by a terminal transferase (e.g., terminal deoxynuclcotidyl transferase). FIG. 2B is a schematic diagram showing generation of a ligation product in situ by hybridizing a pair of probes to a target nucleic acid. The hybridized probes can be complementary to any portion of the target nucleic acid so long as they are adjacent and can be ligated together to form a ligation product. At least one of the probes of the pair of probes has a capture sequence capable of hybridizing to a capture domain of a capture probe. A second primer is added where the second primer includes a sequence complementary to the polynucleotide (e.g., a homopolynucleotide sequence, a heteropolynucleotide sequence) sequence added to the 3' end of the cDNA and a capture sequence. In some examples, the second primer is RNA. After reverse transcription, incorporation of the polynucleotide sequence at 3' end of the cDNA, and further extension of the cDNA using the second primer as an extension template, and ligation of the templated probes, an RNase (e.g., RNase H) is contacted with the biological sample (e.g., a tissue section). The RNase degrades the RNA strand of the RNA/cDNA duplex and the RNA strand of the ligation product/RNA duplex, leaving a single-stranded cDNA product (e.g., an extension product) that includes the first primer at its 5' end and the complement of the capture sequence (e.g., a second capture sequence) capable of hybridizing a capture domain of a capture probe and a single-stranded ligation product including a capture sequence (e.g., a first capture sequence) capable of hybridizing to a sequence in a capture domain of a capture probe.

Figure 3:
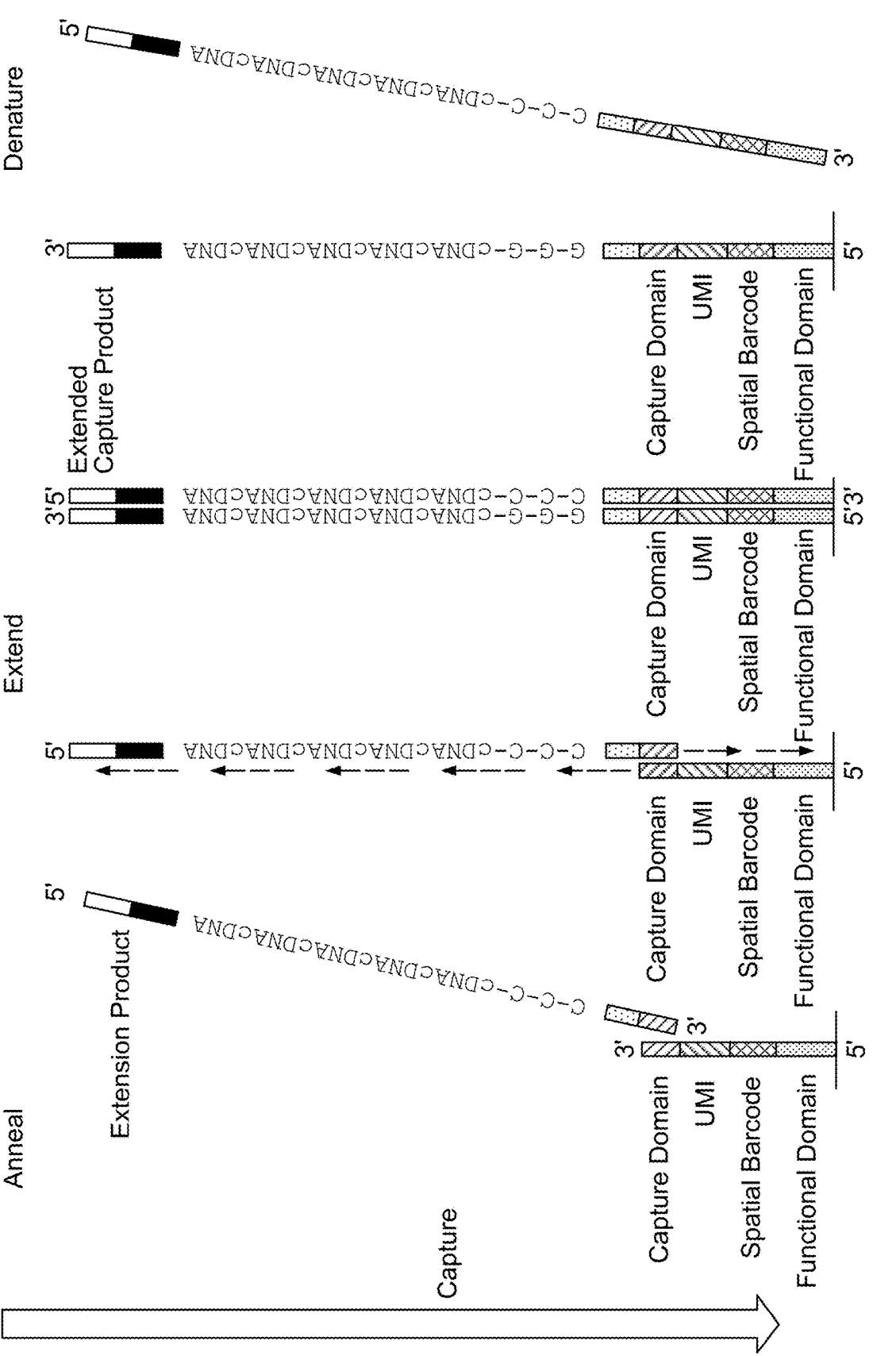
FIG. 3 is a schematic diagram showing capture and extension on an array of the extension product (e.g., cDNA product) shown in FIG. 2A and extension of the capture probe and the captured extension product (e.g., cDNA product) followed by release of the extended capture product.
Figure 7:
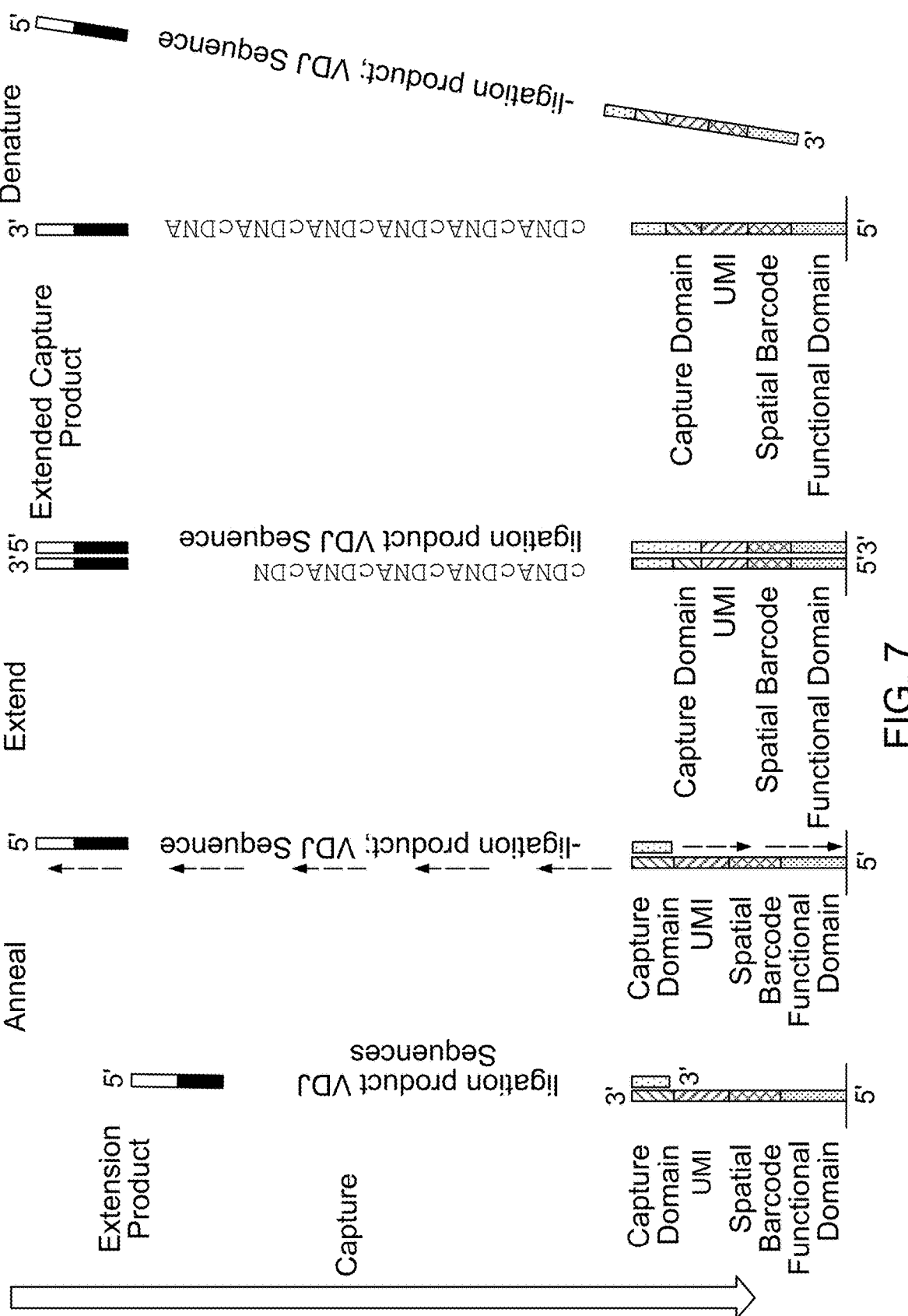
FIG. 7 is a schematic diagram showing capture and extension on an array of the ligation products shown in FIG. 2B and extension of the capture probe and the captured ligation product followed by release of the extended ligation product.

FIG. 3 is a schematic showing capture of the extension product (e.g., the single-stranded cDNA product shown in FIG. 2A) by a capture probe on the substrate. The capture probe is attached to the substrate via its 5' end and can include one or more functional domains, a spatial barcode, a unique molecular identifier, a capture domain, or a combination thereof. In some examples, the capture probe also includes a cleavage domain. The capture domain hybridizes to the complement of the capture sequence within the extension product (e.g., single-stranded cDNA product) from FIG. 2A. In some examples, 3' end of the capture probe is extended using the extension product as a template, thereby generating an extended capture probe. In some examples, 3' end of the extension product (e.g., single-stranded cDNA product) is extended using the capture probe as a template thereby generating an extended capture product. In some examples, 3' end of the capture probe is extended using the extension product as a template and 3' end of the extension product is extended using the capture probe as a template (e.g., generating an extended capture product). In some examples, the extended capture product is released from the capture probe. In some examples, the extended capture product is released via heat. In some examples, the extended capture product is denatured from the capture probe. In some examples, the extended capture product is denatured from the capture probe with KOH. FIG. 7 is a schematic diagram showing capture of the ligation product shown in FIG. 2B by a capture probe on the substrate. The capture probe is attached to the substrate via its 5' end and can include one or more functional domains, a spatial barcode, a unique molecular identifier, a capture domain, or a combination thereof. In some examples, the capture probe also includes a cleavage domain. The capture domain hybridizes to the capture sequence (e.g., the first capture sequence) within the ligation product (e.g., single-stranded ligation product). In some examples, 3' end of the capture probe is extended using the extension product as a template, thereby generating an extended capture probe. In some examples, 3' end of the ligation product is extended using the capture probe as a template, thereby generating an extended ligation product. In some examples, 3' end of the capture probe is extended using the ligation product as a template (e.g., generating an extended capture probe) and the 3' end of the ligation product is extended using the capture probe as a template (e.g., generating an extended ligation product). In some examples, the extended ligation product is released from the capture probe. In some examples, the extended ligation product is released via heat. In some examples, the extended ligation product is denatured from the capture probe. In some examples, the extended ligation product is denatured from the capture probe with KOH.

Figure 6:
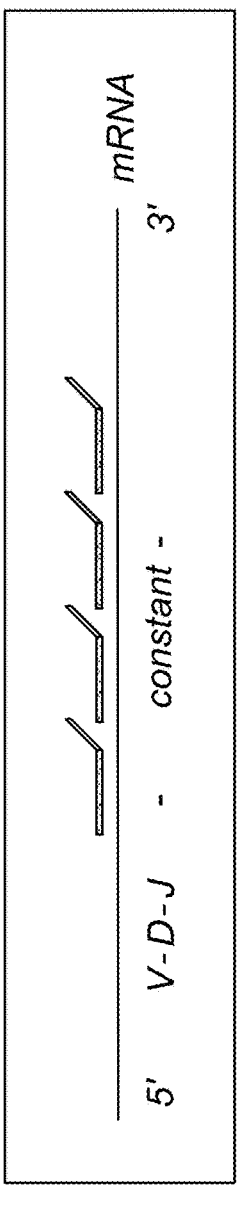
FIG. 6 is a schematic diagram showing reverse transcription of a target nucleic acid with a plurality of primers where the reverse transcription occurs with a reverse transcriptase with strand displacement activity or with a reverse transcriptase with a helicase or a superhelicase (top). In the embodiment shown, the primers hybridize to a region of the target nucleic acid that encodes for a constant region of an immune cell receptor and generate one or more extension products of varying lengths that include V(D)J sequences depending on where the primers hybridize to the target nucleic acid that encodes for a constant region of the immune cell receptor (bottom). This embodiment can be performed with the schematic as shown in FIG. 2A or FIG. 4A.
Figure 6:
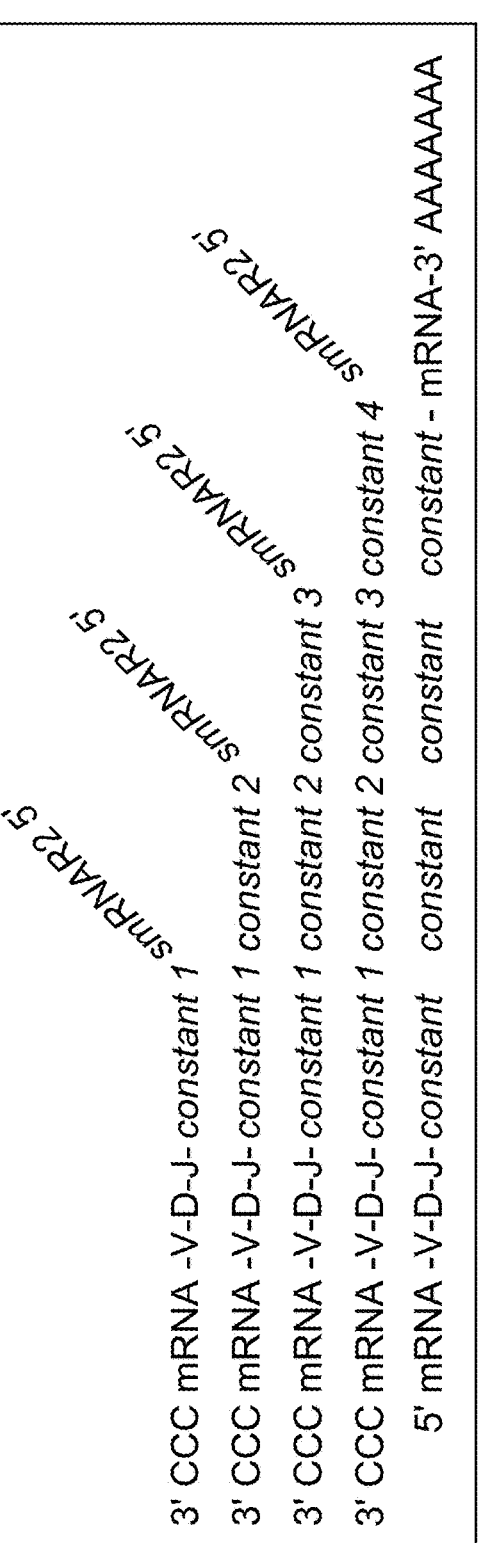

FIG. 6 is a schematic diagram showing an embodiment of FIG. 2A where reverse transcription of a target nucleic acid is performed with a plurality of primers. In some examples, reverse transcription is performed using a reverse transcriptase with strand displacement activity. In some examples, reverse transcription is performed with a reverse transcriptase and a helicase. In some examples, reverse transcription is performed with a reverse transcriptase and a superhelicase. In some examples, reverse transcription is performed with one or more single-stranded DNA binding proteins. When a plurality of primers is used to template reverse transcription as shown in FIG. 2A, the resulting extension products can be of different lengths depending on where the primer hybridized to the target nucleic acid (FIG. 6 (bottom)). In some examples, a primer of the plurality of primers can facilitate more than one reverse transcription reaction, thus resulting in two or more extension products generated from the same region of the target nucleic acid hybridized by the primer.

The released, extended captured products can be prepared for downstream applications, such as generation of a sequencing library and next-generation sequencing.

Figure 9A:
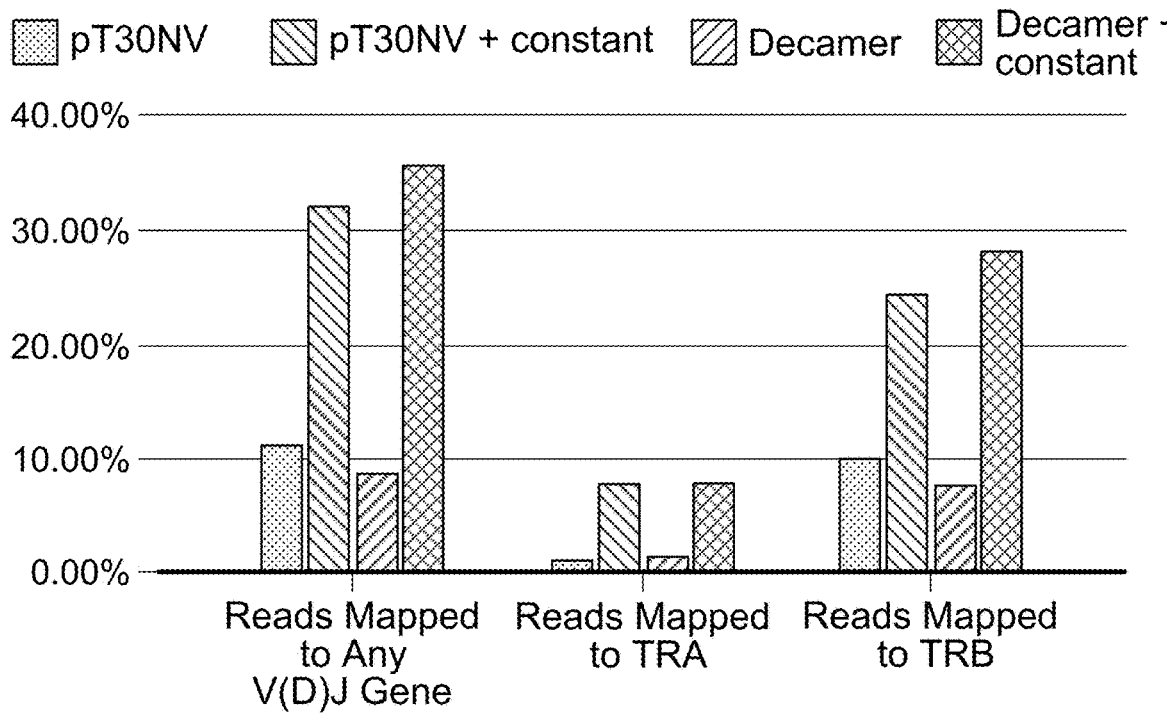
FIGS. 9A-B are graphs showing the sequencing mapping rates for T cell receptors (FIG. 9A) and B cell receptors (FIG. 9B) from a reverse transcription reaction using a plurality of primers to the constant region and poly(A) region of target nucleic acids encoding BCRs and TCRs
Figure 9B:
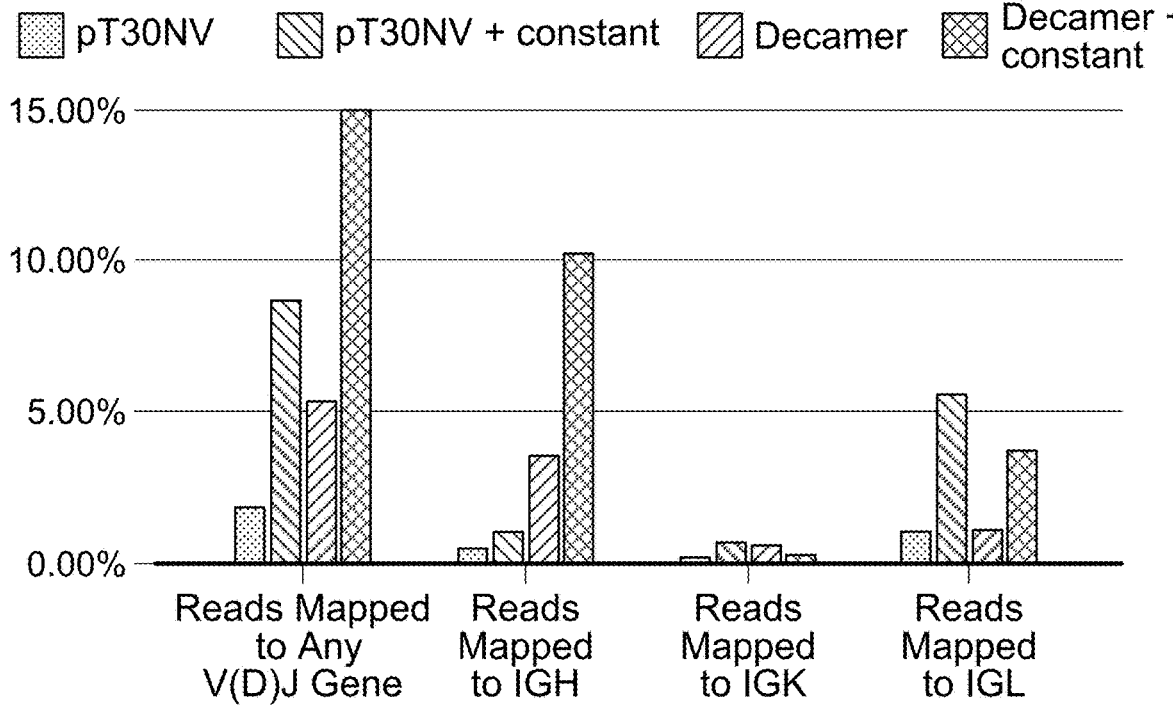

FIGS. 9A-B are graphs showing sequencing mapping rates for T cell receptors (FIG. 9A) and B cell receptors (FIG. 9B) using different primers combinations in a reverse transcription reaction. Briefly, several different primer combinations were tested for their ability to specifically target sequences and prime generation of extension products from nucleic acids encoding T cell receptors and B cell receptors. The plurality of primers used targeted the poly(A) regions of the target nucleic acid and regions encoding the constant region of the B or T cell receptor. This experiment was performed on PBMC FFPE pellets with highly degraded RNA. The data indicates that the TCR and BCR mapping rates improved when further including primers against the constant region. In the absence of RT primers against the constant region of the TCR and BCR, mapping rates were lower.

FIG. 9A shows that a plurality of primers including a poly(dT30NV) sequence only compared with a combination of primers including a plurality of poly(dT30NV) and a plurality of primers to the constant region of T cell receptors results in mapping rates about triple as compared to when only a plurality of primers including a poly(dT30NV) sequence were used. Similarly, FIG. 9A shows that a plurality of primers including a random decamer sequence only compared with a combination of primers including a plurality of random decamer primers and a plurality of primers to the constant region of T cell receptors results in mapping rates about triple as compared to when only a plurality of primers including a random decamer sequence were used. The data show that mapping rates about tripled with respect to reads mapped to any V(D)J gene, reads mapped to a T cell receptor alpha chain, and reads mapped to a T cell receptor beta chain.

FIG. 9B shows that a plurality of primers including a poly(dT30NV) sequence only compared with a combination of primers including a plurality of poly(dT30NV) and a plurality of primers to the constant region of T cell receptors results in mapping rates about triple as compared to when only a plurality of primers including a poly(dT30NV) sequence were used.

Similarly, FIG. 9B shows that a plurality of primers including a random decamer sequence only compared with a combination of primers including a plurality of random decamer primers and a plurality of primers to the constant region of T cell receptors results in mapping rates about triple as compared to when only a plurality of primers including a random decamer sequence were used. The data show that mapping rates about tripled with respect to reads mapped to any V(D)J gene, reads mapped to an immunoglobulin heavy chain, reads mapped to an immunoglobulin kappa light chain, and reads mapped to an immunoglobulin lambda light chain.

Collectively, the data show that 5' capture of target nucleic acids including V(D)J genes, TCRs, and BCRs is enhanced with a 5' capture approach as shown in FIG. 2A and a combination of primers including a plurality of p (dTNV30) primers or a plurality of random decamer primers and a plurality of primers to the constant region of nucleic acid target (e.g., TCRs, BCRs, etc.).

Example 2. 5' Capture of Target Nucleic Acids

Figure 4A:
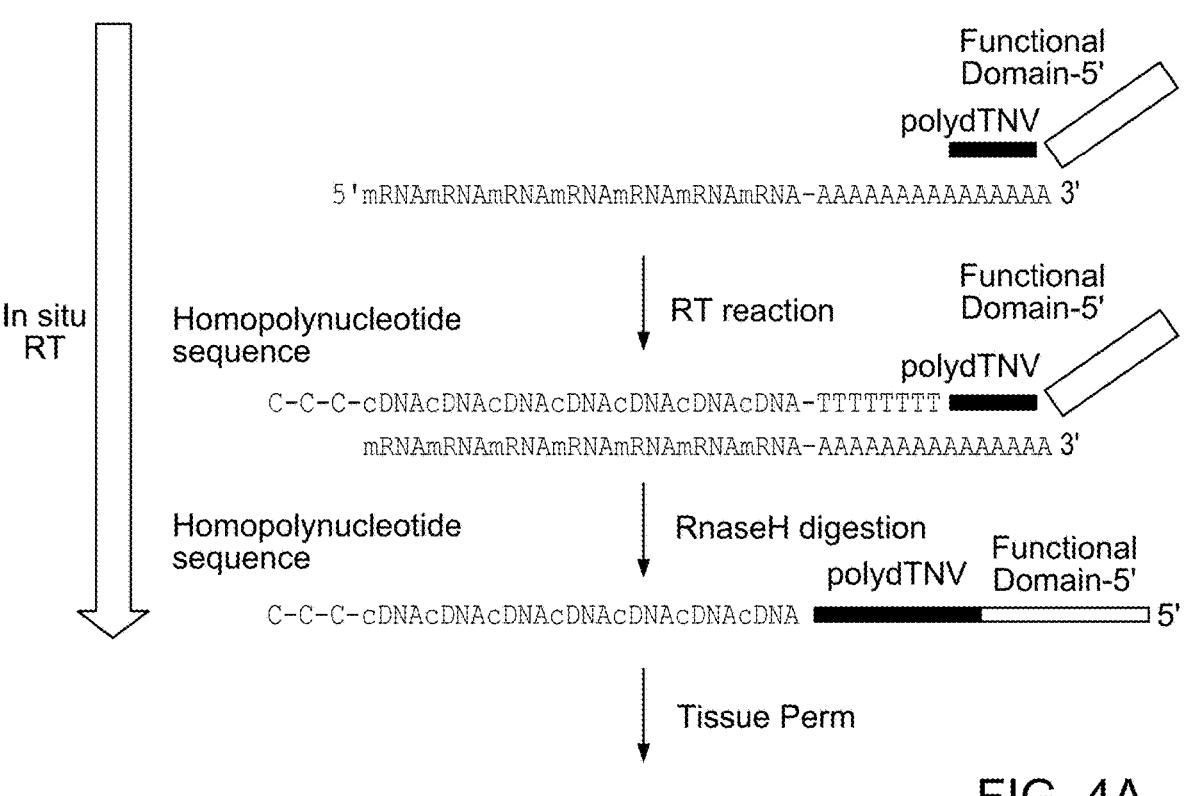
FIGS. 4A-B are schematic diagrams showing reverse transcription of a target nucleic acid with a primer to generate an extension product and the incorporation of a non-templated polynucleotide sequence into the extension product which is capable of hybridizing to a capture domain of a capture probe (FIG. 4A) and a pair of templated ligation probes and a target nucleic acid where the probes hybridize to the target nucleic acid and are ligated to generate a ligation product (FIG. 4B).

FIG. 4A is a schematic showing generation of a cDNA by in situ reverse transcription of a target nucleic acid (e.g., mRNA) from a primer including a sequence complementary to the target nucleic acid and a functional domain. More specifically, target nucleic acids are contacted with a primer that includes a sequence complementary to the target nucleic acid (e.g., poly(dT) sequence, a poly(dTNV) sequence, a random sequence, a sequence in the target nucleic acid encoding a constant region of a B cell receptor (e.g., an antibody), or a T cell receptor) and a functional domain. In some examples, the functional domain is a primer binding site. In some examples, the functional domain is a sequencing specific site (e.g., Read2 site). The target nucleic acid is reverse transcribed into cDNA and a polynucleotide sequence is added to (or incorporated at) 3' end of the cDNA. FIG. 4A shows a homopolynucleotide sequence comprising cytosines, however, it is appreciated that other polynucleotide sequences can be added to the 3' end of the cDNA, including a heteropolynucleotide sequence, e.g., 5'-CGC-'3. In some examples, the polynucleotide sequence is added by the reverse transcriptase. In some examples, the polynucleotide sequence is added by a terminal transferase (e.g., terminal deoxynucleotidyl transferase).

Figure 4B:
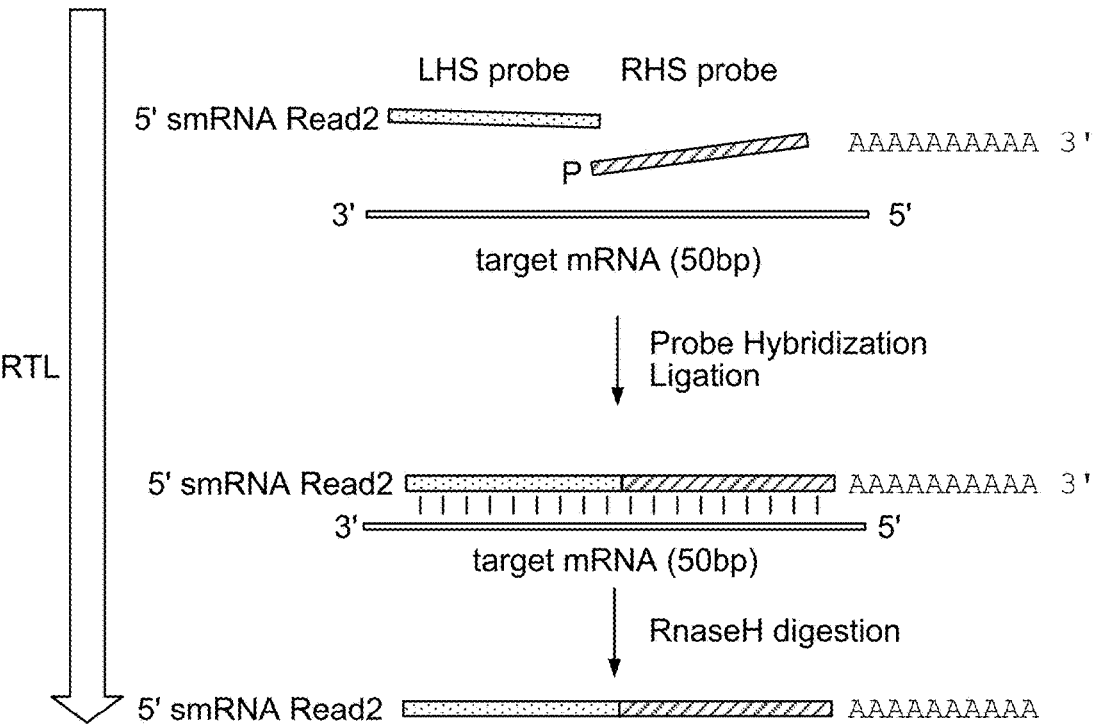

FIG. 4B is a schematic diagram showing generation of a ligation product in situ by hybridizing a pair of probes to a target nucleic acid. The hybridized probes can be complementary to any portion of the target nucleic acid so long as they are adjacent and can be ligated together to form a ligation product. At least one of the probes of the pair of probes has a capture sequence capable of hybridizing to a capture domain of a capture probe.

After reverse transcription and extension of 3' end of the cDNA and hybridization and ligation of the templated probes, an RNase (e.g., RNase H) is contacted with the biological sample (e.g., a tissue section). The RNase degrades the RNA strand of the RNA/cDNA duplex and the RNA strand of the ligation product/RNA duplex, leaving a single-stranded cDNA product (e.g., an extension product) that includes the primer at its 5' end and the added poly-nucleotide sequence which is substantially complementary to and capable of hybridizing to a capture domain of a capture probe, and a single-stranded ligation product includ-ing a capture sequence capable of hybridizing to a sequence in a capture domain of a capture probe.

Figure 5:
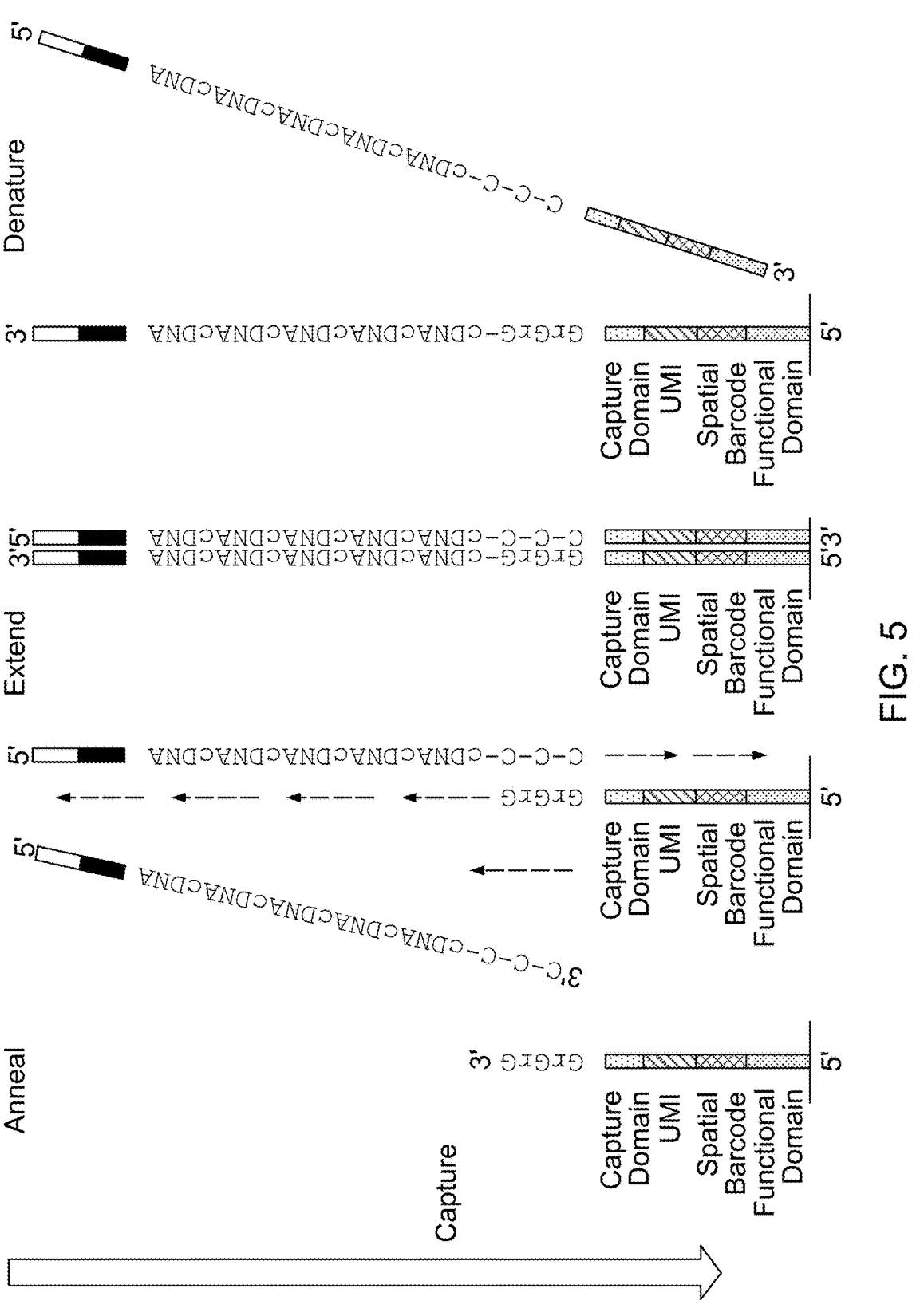
FIG. 5 is a schematic diagram showing capture and extension on an array of the extension product (e.g., cDNA product) shown in FIG. 4A and extension of the capture probe and the captured extension product (e.g., cDNA product) followed by release of the extended capture product.

FIG. 5 is a schematic showing capture of the extension product (e.g., the single-stranded cDNA product shown in FIG. 4A by a capture probe on the substrate. The capture probe is attached to the substrate via its 5' end and can include one or more functional domains, a spatial barcode, a unique molecular identifier, a capture domain, or a com-bination thereof. In some examples, the capture probe also includes a cleavage domain. The capture domain (which includes RNA in some embodiments) hybridizes to the added polynucleotide sequence which is substantially complementary to and capable of hybridizing to a capture domain of a capture probe within the extension product (e.g., single-stranded cDNA product) from FIG. 4A. In some examples, 3' end of the capture probe is extended using the extension product as a template, thereby generating an extended capture probe. In some examples, 3' end of the extension product (e.g., single-stranded cDNA product) is extended using the capture probe as a template, thereby generating an extended capture product. In some examples, 3' end of the capture probe is extended using the extension product as a template and 3' end of the extension product is extended using the capture probe as a template (e.g., gen-erating an extended capture product). In some examples, the extended capture product is released from the capture probe. In some examples, the extended capture product is released via heat. In some examples, the extended capture product is denatured from the capture probe. In some examples, the extended capture product is denatured from the capture probe with KOH. FIG. 7 is a schematic diagram showing capture of the ligation product shown in FIG. 4B by a capture probe on the substrate. The capture probe is attached to the substrate via its 5' end and can include one or more functional domains, a spatial barcode, a unique molecular identifier, a capture domain, or a combination thereof. In some examples, the capture probe also includes a cleavage domain. The capture domain hybridizes to the capture sequence (e.g., the first capture sequence) within the ligation product (e.g., single-stranded ligation product). In some examples, 3' end of the capture probe is extended using the extension product as a template. In some examples, the 3' end of the ligation product is extended using the capture probe as a template thereby generating an extended ligation product. In some examples, 3' end of the capture probe is extended using the ligation product as a template and 3' end of the ligation product is extended using the capture probe as a template (e.g., generating an extended ligation product). In some examples, the extended ligation product is released from the capture probe. In some examples, the extended ligation product is released via heat. In some examples, the extended ligation product is denatured from the capture probe. In some examples, the extended ligation product is denatured from the capture probe with KOH.

FIG. 6 is a schematic diagram showing an embodiment of FIG. 4A where reverse transcription of a target nucleic acid is performed with a plurality of primers. In some examples, reverse transcription is performed using a reverse tran-scriptase with strand displacement activity. In some examples, reverse transcription is performed with a reverse transcriptase and a helicase. In some examples, reverse transcription is performed with a reverse transcriptase and a superhelicase. In some examples, reverse transcription is performed with one or more single-stranded DNA binding proteins. When a plurality of primers is used to template reverse transcription as shown in FIG. 4A, the resulting extension products can be of different lengths depending on where the primers hybridized to the target nucleic acid (FIG. 6 (bottom)). In some examples, a primer of the plurality of primers can facilitate more than one reverse transcription reaction, thus resulting in two or more extension products generated from the same region of the target nucleic acid hybridized by the primer.

The released, extended captured products can be prepared for downstream applications, such as generation of a sequencing library and next-generation sequencing.

Figure 10A:
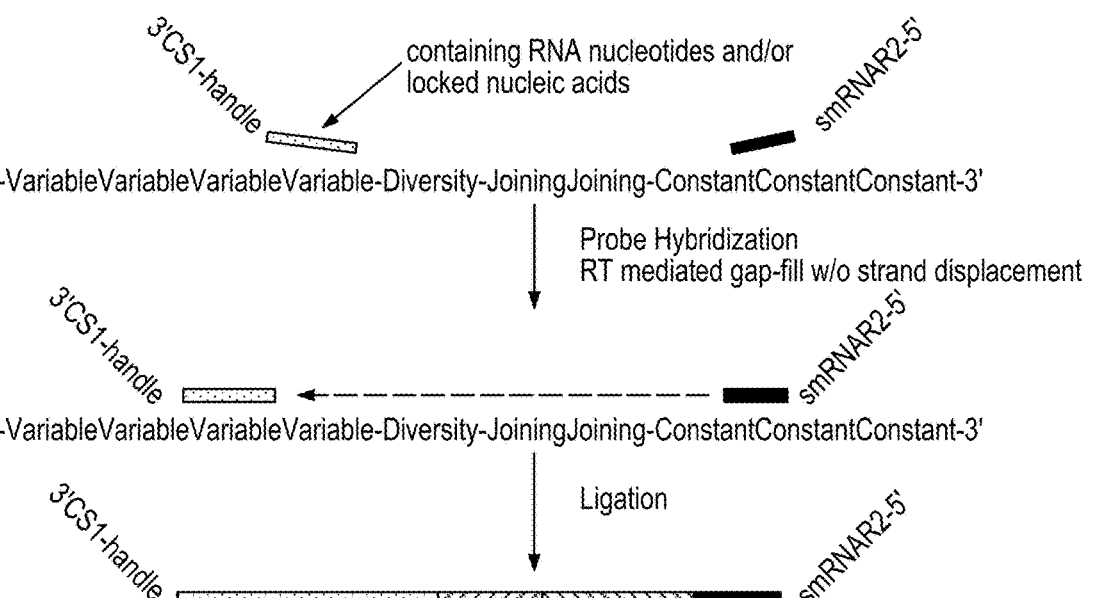
FIGS. 10A-B are schematic diagrams showing a pair of templated ligation probes and a target nucleic acid where the probes hybridize to separate portions of the target nucleic acid, filling of the gap between the probes by extension of the first probe, and ligation of the extension product to the second probe (FIG. 10A).

Example 3. Capture of Ligation Product Via Templated-Ligation and Gap-Filling FIG. 10A is a schematic diagram showing generation of a ligation product in situ by hybridizing a pair of probes to a target nucleic acid. The hybridized probes can be comple-mentary to any portion of the target nucleic acid. In some instances, there are one or more intervening nucleotides between the hybridized first probe and the second probe. In some examples, the first probe hybridizes to the constant region of a target nucleic acid. In some examples, the first probe hybridizes to a sequence encoding the constant region of a B cell receptor. In some examples, the first probe hybridizes to a sequence encoding the constant region of a T cell receptor. In some examples, the second probe hybrid-izes to the variable region of a target nucleic acid. In some examples, the second probe hybridizes to a sequence encod-ing the variable region of a B cell receptor. In some examples, the second probe hybridizes to a sequence encod-ing the variable region of a T cell receptor.

The first probe and/or the second probe can include DNA nucleotides, RNA nucleotides, locked nucleic acids, or com-binations thereof. In some examples, the first probe includes a portion substantially complementary to the target nucleic acid and a functional domain. In some examples, the func-tional domain is a primer binding site or a sequencing specific site. In some examples, the second probe includes a portion substantially complementary to the target nucleic acid and a capture sequence capable of binding (e.g., hybrid-izing) to a sequence in a capture domain of a capture probe.

After the pair of probes hybridize to the target nucleic acid (e.g., DNA, RNA) the intervening nucleic acid sequence between the probe pair functions as a template for an extension (e.g., reverse transcription) reaction. More spe-cifically, a polymerase (e.g., a reverse transcriptase) extends the first probe, thereby generating an extension product (e.g., via a gap-filling reaction). In some examples, the poly-merase (e.g., reverse transcriptase) does not possess strand displacement activity. In some examples, the extension product (e.g., the extended first probe) is ligated to the second probe, thereby generating a ligation product. In some examples, the second probe is extended to generate an extension product, which can then be ligated to the first probe to generate the ligation product. In some examples, the target nucleic acid is removed from the ligation product prior to capture of the ligation product by a capture probe on a substrate. In some examples, the target nucleic acid is RNA (e.g., mRNA). In such examples, the RNA can be removed via an endoribonuclease, such as an RNase. In some examples, the RNase is RNase H. In some examples, the target nucleic acid is DNA (e.g., cDNA).

Figure 10B:
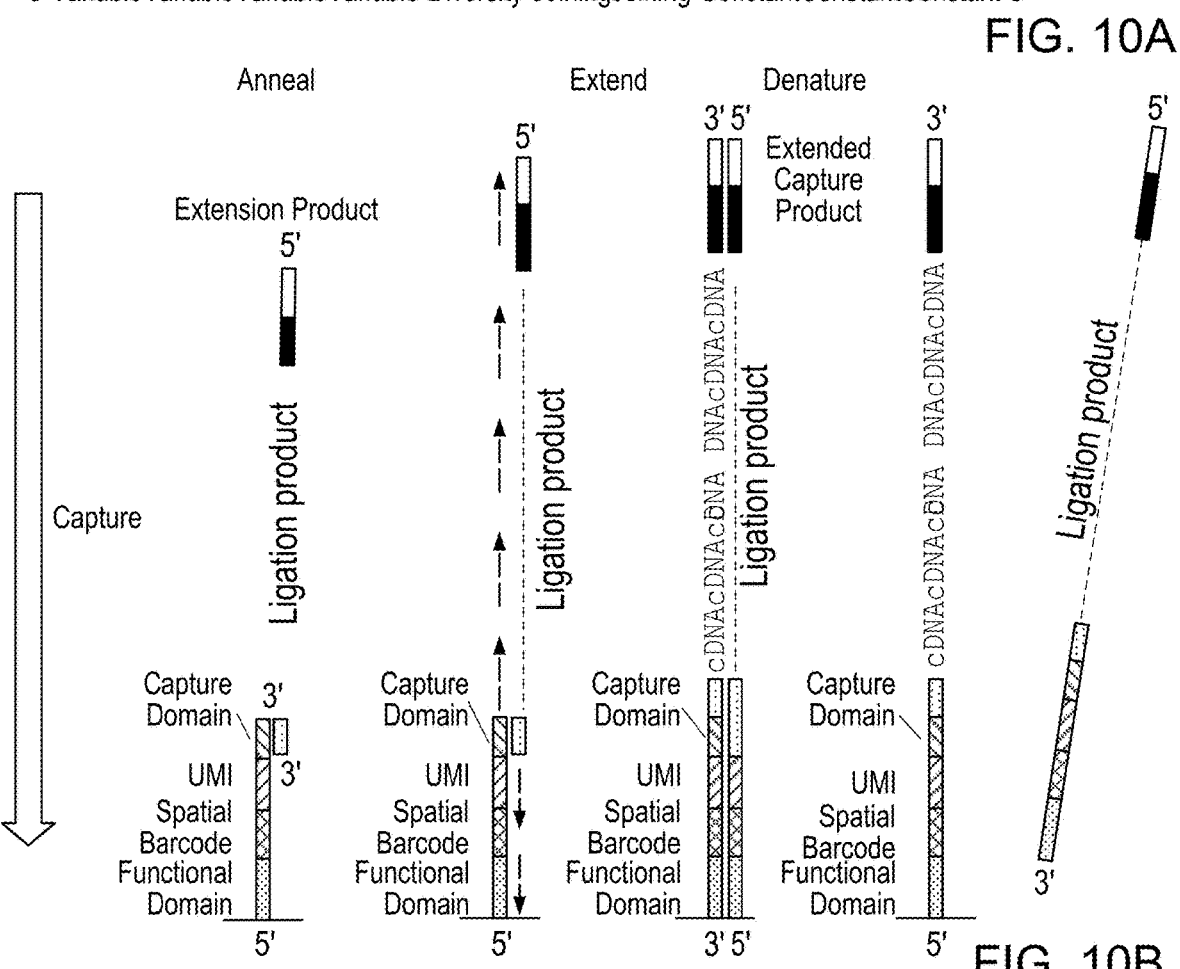

FIG. 10B is a schematic diagram showing capture and extension of the ligation product shown in FIG. 10A by a capture probe on the substrate. The capture probe is attached to the substrate via its 5' end and can include one or more functional domains, a spatial barcode, a unique molecular identifier, a capture domain, or combinations thereof. In some examples, the capture probe also includes a cleavage domain. The capture domain hybridizes to the capture sequence within the ligation product (e.g., single-stranded ligation product). In some examples, 3' end of the capture probe is extended using the ligation product as a template, thereby generating an extended capture probe. In some examples, the 3' end of the ligation product is extended using the capture probe as a template, thereby generating an extended ligation product. In some examples, 3' end of the capture probe is extended using the ligation product as a template and 3' end of the ligation product is extended using the capture probe as a template (e.g., generating an extended ligation product). In some examples, the extended ligation product is released from the capture probe. In some examples, the extended ligation product is released via heat. In some examples, the extended ligation product is denatured from the capture probe. In some examples, the extended ligation product is denatured from the capture probe with KOH.

(ii) a first primer comprising a sequence that hybridizes to a complementary sequence in the second target nucleic acid, and a functional domain;

(b) hybridizing the first probe and the second probe to the first target nucleic acid;

(c) generating a ligation product by ligating the first probe to the second probe;

(d) hybridizing the first capture sequence of the ligation product to the first capture domain on an array, wherein the array comprises a first plurality of capture probes, wherein a first capture probe of the first plurality of capture probes comprises: a first spatial barcode and the first capture domain;

(e) hybridizing the first primer to the second target nucleic acid and extending the first primer using the second target nucleic acid as a template to generate an extension product;

(f) incorporating a polynucleotide sequence comprising at least three nucleotides to 3' end of the extension product;

(g) hybridizing a second primer to the polynucleotide sequence of the extension product of step (f), wherein the second primer comprises a second capture sequence;

(h) extending the extension product of step (g) using the second primer as a template, thereby incorporating a complement of the second capture sequence into the extension product;

(i) hybridizing the complement of the second capture sequence of the extension product of (h) to a second capture domain on the array, wherein the array comprises a second plurality of capture probes, wherein a second capture probe of the second plurality of capture probes comprises: a second spatial barcode and the second capture domain;

---

---

What is claimed is:

1. A method for determining a location of a first target nucleic acid and a second target nucleic acid in a biological sample, the method comprising:

(a) contacting the biological sample with:

(i) a first probe and a second probe, wherein the first probe and the second probe each comprise sequences that are substantially complementary to sequences of the first target nucleic acid, and wherein the second probe further comprises a first capture sequence that is complementary to all or a portion of a first capture domain; and (j) determining (i) the sequence of the first spatial barcode, or a complement thereof, and (ii) all or a portion of the sequence of the ligation product hybridized to the first capture domain, or a complement thereof, and using the determined sequences of (i) and (ii) to determine the location of the first target nucleic acid in the biological sample; and (k) determining (iii) the sequence of the second spatial barcode, or a complement thereof, and (iv) all or a portion of the sequence of the extension product corresponding to a sequence of the second target nucleic acid, or a complement thereof, and using the determined sequences of (iii) and (iv) to determine the location of the second target nucleic acid in the biological sample.

2. The method of claim 1, wherein the biological sample is disposed on the array comprising the first plurality and the second plurality of capture probes.

3. The method of claim 1, wherein the biological sample is disposed on a first substrate, and wherein the array comprising the first plurality of capture probes and the second plurality of capture probes is disposed on a second substrate and wherein the method further comprises aligning the first substrate with the second substrate, such that at least a portion of the biological sample is aligned with at least a portion of the array.

4. The method of claim 1, wherein the hybridizing in steps (d) and/or (i) comprise active migration of the ligation product and/or the extension product to the array, and optionally, wherein the active migration comprises electrophoresis.

5. The method of claim 1, wherein the polynucleotide sequence in step (f) comprises a homopolynucleotide sequence, optionally 5'-CCC-3'; or wherein the polynucleotide sequence in step (f) comprises a heteropolynucleotide sequence, optionally 5'-CGC-3'.

6. The method of claim 1, wherein the first capture domain comprises a first fixed sequence, optionally poly(T), and the second capture domain comprises a second fixed sequence, optionally poly(T).

7. The method of claim 1, wherein the first primer comprises a random hexamer or a random decamer.

8. The method claim 1, wherein the first primer comprises a poly(T) sequence.

9. The method claim 1, wherein the first primer comprises a sequence substantially complementary to a sequence in the second target nucleic acid encoding a constant region of an antibody; or wherein the first primer comprises a sequence substantially complementary to a sequence in the second target nucleic acid encoding a constant region of a B cell receptor; or wherein the first primer comprises a sequence substantially complementary to a sequence in the second target nucleic acid encoding a constant region of a T cell receptor.

10. The method of claim 1, wherein the functional domain comprises a primer binding site or a sequencing specific site.

11. The method of claim 1, wherein the first target nucleic acid is mRNA.

12. The method of claim 1, wherein the second target nucleic acid is mRNA.

13. The method of claim 1, wherein the extending in step (e) comprises the use of a reverse transcriptase.

14. The method of claim 1, wherein incorporating the polynucleotide sequence to the 3' end of the extension product in step (f) comprises the use of a terminal deoxynucleotidyl transferase or the use of a reverse transcriptase.

15. The method of claim 1, wherein the second primer comprises RNA.

16. The method of claim 1, wherein the method further comprises removing the second target nucleic acid or any other nucleic acid hybridized to the extension product before the complement of the second capture sequence of the extension product hybridizes to the second capture domain of the second capture probe and/or removing the first target nucleic acid, or any other nucleic acid hybridized to the ligation product, before the first capture sequence of the ligation product hybridizes to the first capture domain of the first capture probe; and wherein the removing comprises the use of an RNase, optionally, wherein the RNase is RNase H, or heat.

17. The method of claim 1, wherein the method further comprises a step of extending the 3' end of the extension product of step (i) using the second capture probe as a template, thereby generating an extended capture product; and/or extending the second capture probe using the extension product of step (i) as a template, thereby generating an extended second capture probe; and/or a step of extending 3' end of the ligation product using the first capture probe as a template, thereby generating an extended ligation product; and/or extending the first capture probe using the ligation product as a template, thereby generating an extended first capture probe.

18. The method of claim 1, wherein the determining in step (j) and step (k) comprises sequencing.

19. The method of claim 1, wherein the biological sample is a tissue section.

20. The method of claim 19, wherein the tissue section is a fixed tissue section, optionally, wherein the fixed tissue section is a formalin-fixed paraffin embedded tissue section, a paraformaldehyde-fixed tissue section, a methanol-fixed tissue section, or an acetone-fixed tissue section.

21. The method of claim 1, wherein the first probe and the second probe are substantially complementary to adjacent sequences of the first target nucleic acid.

22. The method of claim 1, wherein the first probe and the second probe hybridize to sequences that are not adjacent to each other on the first target nucleic acid and wherein the first probe is extended with a DNA polymerase, thereby (i) filling in a gap between the first probe and the second probe and (ii) generating an extended first probe.

23. The method of claim 1, wherein the first capture probe and/or the second capture probe further comprise one or more functional domains, a unique molecular identifier, a cleavage domain, or a combination thereof.

24. The method of claim 1, wherein the method further comprises fixing, staining, and/or imaging the biological sample.

* * * * *

SEQUENCE LISTING

```
Sequence total quantity: 2
SEQ ID NO: 1            moltype = RNA   length = 15
FEATURE                 Location/Qualifiers
source                  1..15
                        mol_type = other RNA
                        organism = synthetic construct
SEQUENCE: 1
aaaaaaaaaa aaaaa                                               15

SEQ ID NO: 2            moltype = DNA   length = 10
FEATURE                 Location/Qualifiers
source                  1..10
                        mol_type = other DNA
                        organism = synthetic construct
SEQUENCE: 2
aaaaaaaaaa                                                     10
```